(12) United States Patent
Tischler et al.

(10) Patent No.: US 11,723,968 B2
(45) Date of Patent: Aug. 15, 2023

(54) STABILIZED RECOMBINANT HANTAVIRAL SPIKE PROTEINS COMPRISING MUTATIONS IN GC

(71) Applicants: FUNDACIÓN CIENCIA PARA LA VIDA, Santiago (CL); INSTITUT PASTEUR, Paris (FR)

(72) Inventors: Nicole Tischler, Santiago (CL); Eduardo Andrés Bignon Silva, Santiago (CL); Félix Augusto Rey, Paris (FR); Pablo Guardado Calvo, Paris (FR)

(73) Assignees: FUNDACION CIENCIA PARA LA VIDA, Santiago (CL); INSTITUT PASTEUR, Paris (FR)

( * ) Notice: Subject to any disclaimer, the term of this patent is extended or adjusted under 35 U.S.C. 154(b) by 0 days.

(21) Appl. No.: 16/980,535

(22) PCT Filed: Mar. 13, 2019

(86) PCT No.: PCT/US2019/022134
§ 371 (c)(1),
(2) Date: Sep. 14, 2020

(87) PCT Pub. No.: WO2019/178286
PCT Pub. Date: Sep. 19, 2019

(65) Prior Publication Data
US 2021/0000940 A1    Jan. 7, 2021

Related U.S. Application Data

(60) Provisional application No. 62/642,429, filed on Mar. 13, 2018.

(51) Int. Cl.
*A61K 39/12* (2006.01)
*C07K 14/005* (2006.01)
*A61P 37/04* (2006.01)

(52) U.S. Cl.
CPC ............ *A61K 39/12* (2013.01); *C07K 14/005* (2013.01); *A61P 37/04* (2018.01); *C12N 2760/12122* (2013.01); *C12N 2760/12134* (2013.01)

(58) Field of Classification Search
CPC .................. A61K 39/12; C07K 14/005; C12N 2760/12122; C12N 2760/12134
See application file for complete search history.

(56) References Cited

PUBLICATIONS

Hepojoki, J., et al., Jan. 2010, Interactions and oligomerization of hantavirus glycoproteins, J. Virol. 84(1):227-242.*
Liu, R., et al., Jan. 2020, Vaccines and therapeutics against hantaviruses, Front. Microbiol. 10, Article 2989, pp. 1-19.*
Kruger, D. H., et al., Jun. 2011, Human pathogenic hantaviruses and prevention of infection, Human Vaccines 7(6):685-693.*
Saavedra, F., et al., 2021, Immune responses during hantavirus diseases: implications for immunotherapies and vaccine design, Immunol. 163:262-277.*
Engdahl, T. B., and J. E. Crowe, Jul./Aug. 2020, Humoral immunity to hantavirus infection, mSphere 5:e00482-20, pp. 1-11.*
Guardado-Calvo, P., et al., Oct. 2016, Mechanistic Insight into Bunyavirus-Induced Membrane Fusion from Structure-Function Analyses of the Hantavirus Envelope Glycoprotein Gc, PLoS Pathog. 12(10):e1005813, pp. 1-32.*
Nandini Sen, et al., "Degrons at the C Terminus of the Pathogenic but Not the Nonpathogenic Hantavirus G1 Tail Direct Proteasomal Degradation", Journal of Virology, Apr. 2007, pp. 4323-4330, vol. 81, No. 8.
Pablo Guardado-Calvo, et al., "Mechanistic Insight into Bunyavirus-Induced Membrane Fusion from Structure-Function Analyses of the Hantavirus Envelope Glycoprotein Gc", PLOS Pathogens | DOI:10.1371/journal.ppat.1005813 Oct. 26, 2016, pp. 1-32.

* cited by examiner

*Primary Examiner* — Jeffrey S Parkin
(74) *Attorney, Agent, or Firm* — Ladas & Parry LLP

(57) ABSTRACT

The present invention describes specific engineering of the hantavirus spike proteins with modifications to stabilize $(Gn/Gc)_n$ heterodimer contacts and/or Gc homodimer contacts and/or Gn/Gn oligomer contacts on the spike with the purpose of using them as immunogens in next-generation vaccine design. Said spike proteins have been covalently stabilized by at least one disulphide inter-chain bond between Gn/Gc heterodimers and/or between Gc homodimers and/or between Gn homo-oligomers as they are presented at the surface of infectious virions. It also involves spike stabilization by introduction of cavity-filling amino acids with a bulky side chain at the above-mentioned contacts. Said spike proteins can be soluble Gn/Gc ectodomains in solution and/or incorporated as $(Gn/Gc)_n$ heterooligomers onto virus-like particles (VLPs) and/or used for pseudotyping virus vectors and/or form part of a stabilized recombinant virus, wherein said spike proteins can be used to select ligands and/or can be used for preventing or treating infections by one or more hantaviruses.

14 Claims, 12 Drawing Sheets
Specification includes a Sequence Listing.

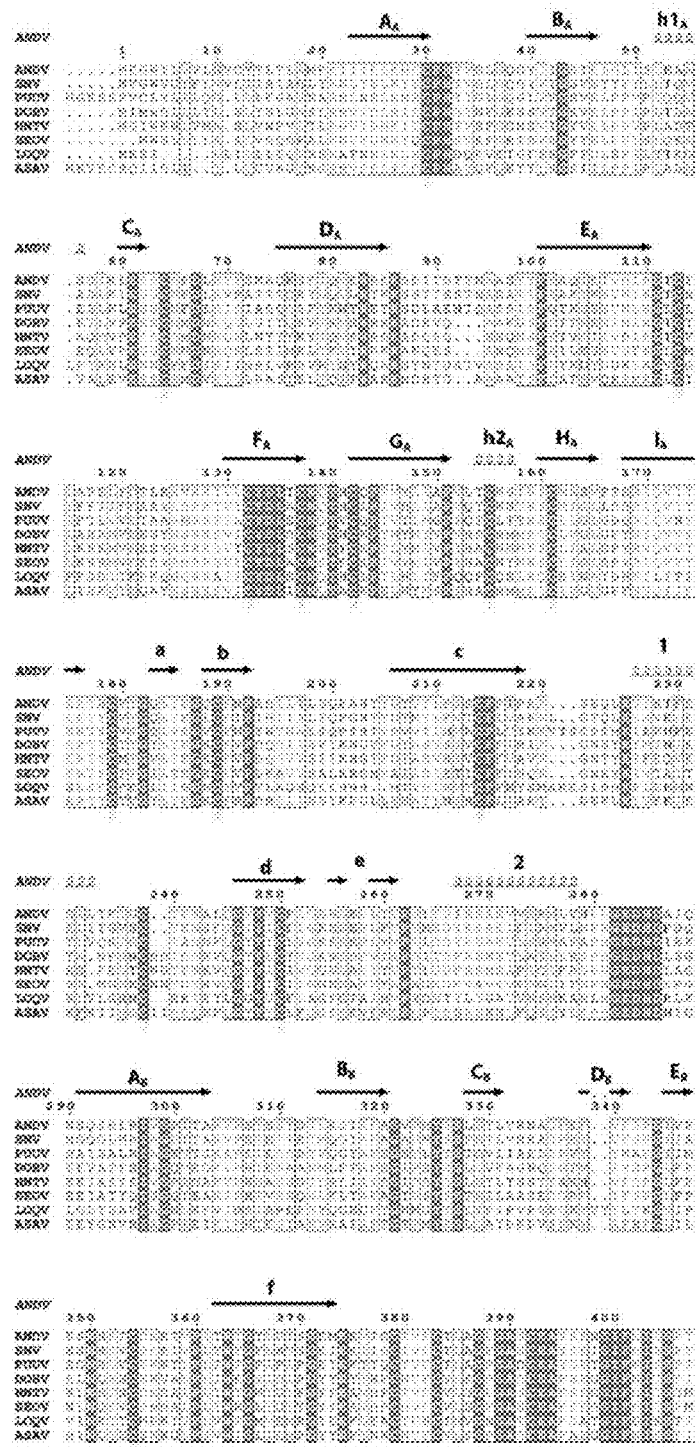
Figure 1 (partial)

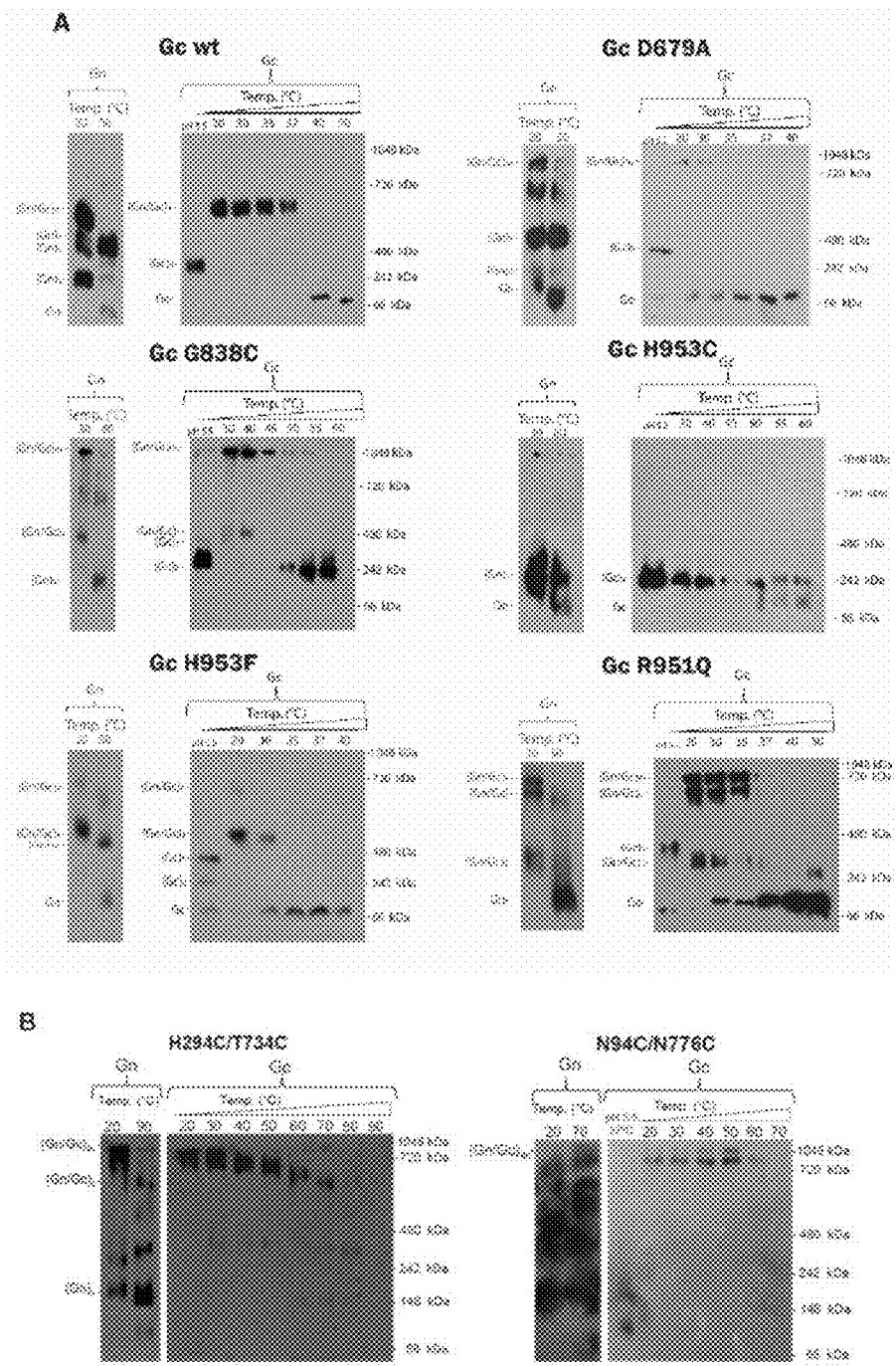
Figure 7 (part)

A

B

STABILIZED RECOMBINANT HANTAVIRAL SPIKE PROTEINS COMPRISING MUTATIONS IN GC

REFERENCE TO SEQUENCE LISTING SUBMITTED VIA EFS-WEB

This application includes an electronically submitted sequence listing in .txt format. The .txt file contains a sequence listing entitled "U 020630-5_ST25.txt" created on Nov. 23, 202 and is 188,014 bytes in size. The sequence listing contained in this .txt file is part of the specification and is hereby incorporated by reference herein in its entirety.

FIELD OF THE INVENTION

The invention relates to the field of preventing and treating hantavirus infections and related antigens and uses.

BACKGROUND OF THE INVENTION

Hantavirus Disease

Hantaviruses are worldwide spread pathogens that can cause severe disease in humans such as hantavirus pulmonary syndrome (HPS) and hemorrhagic fever with renal syndrome (HFRS). While the former disease occurs principally in America with mortality rates that can reach up to 50%, the latter produces yearly 150-200 thousand cases in Asia and in a milder version in Europe with lethality rates ranging from 1 to 15%. Among the most frequent HFRS-causing viruses, Hantaan virus is the prototype virus and is endemic in Asia, especially in China, Russia, and Korea. Several other HFRS-causing hantaviruses have been identified, among them the most frequent ones are Seoul virus that is endemic worldwide, Dobrava virus primarily in the Balkans and the Puumala virus producing weaker forms of HFRS in Scandinavia, western Europe and western Russia. The higher pathogenic Dobrava virus has been re-emerging during the last years and a permanent risk of expansion in Central Europe has been reported. In America, hantaviruses are the most lethal endemic viruses and have been emerging and re-emerging since 1993, being Sin Nombre virus the most frequent cause of HPS in North America and Andes virus in South America. In this context, the US National Institute of Allergy and Infectious Diseases (NIAID) from the National Institute of Health (NIH), has classified hantaviruses that cause hantavirus pulmonary syndrome as NIAID category A pathogens of highest priority. Such prioritized emerging pathogens represent the highest risk to the national security and public health, since they are easily transmitted from person to person, produce high mortality rates, might cause public panic and social disruption and require special action for public health preparedness in absence of effective therapeutic or prophylactic treatments against hantavirus diseases (NIH, 2016). Given that hantaviruses the hosts of are rodents and insectivores, their eradication is impossible. At the date of patent application, no therapeutic or prophylactic solutions (e.g. vaccines) approved by the NIH are available.

Hantavirus Vaccines and Antiviral Treatments

For hantaviruses that produce HFRS, there exist at least three different vaccine preparations based on formalin-inactivated virus produced suckling-mouse brains or in cell cultures that was only commercialized locally in China and South Korea (Maes et al., 2009). Besides a vaccination scheme consisting of three doses, the neutralizing antibody response has been reported to be short lived and the efficacy of the vaccine must be re-evaluated. These vaccines are not approved in the USA and other countries of America where the highest mortality rates through hantavirus disease exist due to the high risk that is involved in the production of such a vaccine in higher quantities.

Another vaccine approach that has reached a clinical trial study corresponds to a DNA vaccine based on plasmids that encode the hantavirus Gn/Gc spike proteins of the hantaviruses Andes, Puumala, Hantaan and Seoul under the cytomegalovirus promotor. When in a phase I clinical trial these plasmids were administrated into the dermis of humans, neutralizing antibodies were induced in 30 to 56% of the volunteers (Boudreau et al. 2012). However, given that currently only one product has been approved to perform gene therapy in humans, and not a single DNA vaccine has yet been approved, it seems difficult that such an approach will reach acceptance to be used in healthy humans due to the risk of spontaneous integration of DNA into the human genome.

In terms of antiviral treatments, broad spectrum antivirals such as Ribavirin have proven to be inefficient. However, another approach using plasma from surviving patients has been used in an open clinical trial in HPS patients in Chile from 2008 to 2012. In this trial, 29 out of 32 patients were treated and reached a mortality rate of 14%, compared to a 32% rate for non-treated patients during the same period and 28% for non-treated patients in the same geographic zone (Vial et al., 2015). While this treatment seemed safe, it is difficult to standardize given that 1) the titer of neutralizing antibodies in humans varies over time and 2) access to surviving patients' plasmas is generally scarce hence being a variable that is difficult to control. The scarceness of immune sera is the reason why it is currently only used in patients with severe symptoms.

Overall, each here described preventive or therapeutic approach shows that there is an urgent need to develop improved solutions that can be established in the market.

Hantavirus Structure

Hantaviruses (Bunyavirales order) have a genome composed of three single strand RNA segments of negative polarity that encodes at least four structural proteins; the nucleocapsid (N) protein, the viral RNA-dependent RNA polymerase (RdRp) and the two envelope glycoproteins, Gn and Gc, that project from the virion as surface spikes. The virions are pleomorphic and heterogenic in size ranging from 120-160 nm and also elongated particles up to 350 nm in length have been reported. They contain helical capsids in the interior of the virion composed of N covering the three genomic segments associated to RdRp that are enveloped by a lipid membrane displaying the spikes composed of Gn and Gc. The spike proteins resemble hence the outer most proteins of hantavirus virions, and are therefore crucial to direct hantavirus entry into the cell and are at the same time key for virus recognition by the immune system for viral neutralization. In this context, the Gn/Gc are important antigens for the design of vaccines and effective antiviral treatments.

Previous work by Husikonen et al. 2011 using cryo-electron tomography (Cryo-ET) of hantavirus virions demonstrated that the Gn/Gc spikes form a local four-fold quasi symmetry; however, the orientation of Gn and Gc within these spikes remained to be determined. The later structural characterization of Gn monomers and the improvement of the Cryo-ET map allowed Shi et al., 2016 the fitting of Gn monomers into the most distal volumes of the spike density map; however, the exact orientation and molecular contacts of Gn and Gc still awaited to be solved to obtain a molecular understanding of their assembly.

An additional difficulty for the development of preventive and therapeutic strategies represents the high metastability and of the hantaviral spikes. Such metastability has been previously reported for Dengue virus and human immunodeficiency virus spike proteins and seems to apply in general to all enveloped viruses since it is crucial for enveloped virus that their spikes can dissociate once the virus enters into a cell. More specifically, the metastability is associated with the pre-fusion conformation of the viral protein on infectious virions, in the case of hantaviruses this protein corresponds to the Gc glycoprotein. Once the virus bound to cellular receptors, it is uptaken into endosomes where under acidic pH the Gc fusion protein is activated, leading to consecutive conformational changes that expose the Gc fusion loops inserting into the endosomal membrane and lead irreversibly to a stable post-fusion conformation (Guardado-Calvo et al., 2016). Such irreversible pre-fusion to post-fusion transitions have been well described for viral fusion proteins with class I or class II folds, whereby the energy that is released to reach the ground state of these proteins is believed to drive the merger of the virus-cell membranes that allows the ingress of the viral nucleocapsids into the cell cytoplasm, resulting ultimately into the infection of the cell (Harrison, S C. 2015). In this line, for hantaviruses it has been well described that mildly low pH decreases their titer over 100 fold (Hepojoki et al., 2010).

In a wider context, from what is known from other viruses, the viral surfaces have a highly dynamic behavior that leads to the exposure of internal epitopes that are otherwise cryptic. For easy of description the inventors call the conformations opened and closed, in which the closed conformation represents the infectious conformation while the open conformation corresponds to non-infectious conformations (Rey & Lok, 2018). For hantaviruses, there is evidence that the cell culture adapted viruses present mostly open conformations since they are highly labile, losing their infectivity within little hours outside a host cell (Hardestam et al., 2007).

For the design of therapeutic or prophylactic strategies that block efficiently hantavirus infections, it is therefore of crucial importance to arrest the hantaviral spike arrangement in a conformation that resembles that of infectious virus particles (a closed conformation including Gc in its pre-fusion state). To solve this technical problem, it is imperative to know the molecular contacts that establish the infectious conformation of the hantaviral spikes. These contacts involve those of the Gn/Gc heterodimer, those of the Gc/Gc homodimer and those of the Gn/Gn homotetramer. In this context, the present invention discloses the molecular structure of the hantaviral spike lattices, the key amino acids involved in the molecular contacts, and amino acid residue modifications (e.g. substitutions) that significantly improve the hantaviral spike stability in their infectious conformation. Thus, the present invention provides new solutions for the design of improved therapeutic and preventive strategies against hantavirus infections.

SUMMARY OF THE INVENTION

The invention relates to an improved and stabilized recombinant hantaviral spike composed of at least one homodimer of mutants Gc, at least one heterodimer of a mutant Gc and a mutant Gn or at least one oligomer of mutants Gn, or a combination thereof.

The invention relates to the stabilized recombinant hantaviral spike of the present invention comprising at least one homodimer of mutants Gc having each at least one amino acid mutation (substitution) at a position selected from the group consisting of: 676, 677, 678, 679, 680, 681, 682, 683, 832, 833, 834, 835, 836, 837, 838, 839, 840, 841, 842, 843, 844, 845, 846, 847, 951, 952, 953, 954, 955, 956, 957 and 958, the indicated positions being determined by alignment with SEQ ID NO: 1 (using standard alignment online tool BLAST).

The invention relates to the stabilized recombinant hantaviral spike of the present invention wherein the at least one homodimer of mutants Gc is selected from the group consisting of: a homodimer of mutants Gc having each the substitution G838C, a homodimer of mutants Gc having each the substitution T839C, a homodimer of mutants Gc having each the substitution H953C, and a homodimer of mutants Gc having each the substitution H954C, and wherein the amino acid residues 838C, 839C, 953C and 954C are linked respectively to the amino acid residues 838C, 839C, 953C and 954C through disulphide inter-chain bonds.

The invention relates to the stabilized recombinant hantaviral spike of the present invention which comprises at least one homodimer of mutants Gc selected from the group consisting of: a homodimer of mutants Gc having each the double substitution H953C and Q844C, a homodimer of mutants Gc having each the double substitution H954C and Q844C, a homodimer of mutants Gc having each the double substitution S841C and R951C, a homodimer of mutants Gc having each the double substitution E677C and R951C, a homodimer of mutants Gc having each the double substitution D679C and H953C, and a homodimer of mutants Gc having each the double substitution D679C and H954C, and wherein the amino acid residues 677C, 679C, 841C, 844C, 951C, 953C and 954C are linked respectively to the amino acid residues 677C, 679C, 841C, 844C, 951C, 953C and 954C through disulphide inter-chain bonds between the two mutants Gc.

The invention relates to the stabilized recombinant hantaviral spike of the present invention which comprises at least one heterodimer of mutants Gn/Gc, wherein the mutant Gn monomer comprises at least one amino acid mutation (substitution) at a position selected from the group consisting of: 281, 290, 291, 292, 293, 294, 295, 296 and 297, and wherein the mutant Gc monomer comprises at least one amino acid mutation (substitution) at a position selected from the group consisting of: 729, 730, 731, 732, 733, 734, 735, 736, 737 and 748, the indicated positions being determined by alignment with SEQ ID NO: 1.

The invention relates to the stabilized recombinant hantaviral spike of the present invention which comprises at least one heterodimer of a mutant Gn having the substitution H294C and a mutant Gc having the substitution T734C, wherein the amino acid residues 294C and 734C are linked together through a disulphide inter-chain bond.

The invention relates to the stabilized recombinant hantaviral spike of the present invention which comprises at least one heterodimer of a mutant Gn having the substitution N290C and a mutant Gc having the substitution T729C, wherein the residues 290C and 729C are linked together through a disulphide inter-chain bond.

The invention relates to the stabilized recombinant hantaviral spike of the present invention, which comprises at least one amino acid mutation (substitution) at a position selected from the group consisting of: 85, 86, 87, 88, 89, 90, 91, 92, 93, 94, 95, 96, 97, 98 and 99, the indicated positions being determined by alignment with SEQ ID NO: XXX, and wherein the mutant Gc monomer comprises at least one amino acid mutation (substitution) at a position selected from the group consisting of: 738, 739, 740, 741, 742, 743, 744, 745, 746, 747, 774, 775, 776, 777 and 778, the indicated positions being determined by alignment with SEQ ID NO: XXX.

The invention relates to the stabilized recombinant hantaviral spike of the present invention which comprises at least one heterodimer of a mutant Gn having the substitution K85C and a mutant Gc having the substitution P774C, wherein the residues 85C and 774C are linked together through a disulphide inter-chain bond.

The invention relates to the stabilized recombinant hantaviral spike of the present invention which comprises at least one heterodimer of a mutant Gn having the substitution N94C and a mutant Gc having the substitution V776C, wherein the residues 94C and 776C are linked together through a disulphide inter-chain bond.

The invention relates to the stabilized recombinant hantaviral spike of the present invention which comprises at least one heterodimer of a mutant Gn having the substitution A95C and a mutant Gc having the substitution Y739C, wherein the residues 95C and 739C are linked together through a disulphide inter-chain bond.

The invention relates to the stabilized recombinant hantaviral spike of the present invention which comprises at least one heterodimer of a mutant Gn having the substitution T99C and a mutant Gc having the substitution P774C, wherein the residues 99C and 774C are linked together through a disulphide inter-chain bond.

The invention relates to the stabilized recombinant hantaviral spike of the present invention which comprises at least one heterodimer of a mutant Gn having the substitution R281C and a mutant Gc having the substitution P748C, wherein the residues 281C and 748C are linked together through a disulphide inter-chain bond.

The invention relates to the stabilized recombinant hantaviral spike of the present invention which comprises at least one Gn/Gc heterodimer, wherein mutant Gn comprises at least one amino acid mutation (substitution) at a position selected from the group consisting of: 203, 204, 205 and 206, and wherein Gc comprises at least one amino acid mutation (substitution) at a position selected from the group consisting of: 853, 854 and 855, the indicated positions being determined by alignment with SEQ ID NO: 1.

The invention relates to the stabilized recombinant hantaviral spike of the present invention which comprises at least one heterodimer of a mutant Gn having the substitution H203C and a mutant Gc having the substitution L855C, wherein the residues 203C and 855C are linked together through a disulphide inter-chain bond.

The invention relates to the stabilized recombinant hantaviral spike of the present invention which comprises at least one heterodimer of a mutant Gn having the substitution D206C and a mutant Gc having the substitution P854C, wherein the residues 206C and 854C are linked together through a disulphide inter-chain bond.

The invention relates to the stabilized recombinant hantaviral spike of the present invention which comprises at least one homooligomer of a mutant Gn having at least one mutation (substitution) at a position selected from the group consisting of: 332, 333, 334, 335, 336, 337 and 338, and a mutant Gn having at least one mutation (substitution) at a position selected from the group consisting of: 177, 178, 179, 180, 181 and 182, the indicated positions being determined by alignment with SEQ ID NO: 1.

The invention relates to the stabilized recombinant hantaviral spike of the present invention which comprises at least one homooligomer of a mutant Gn having at least one mutation (substitution) at a position selected from the group consisting of: 332, 333, 334, 335, 336, 337 and 338, and a mutant Gn having at least one mutation (substitution) at a position selected from the group consisting of: 374, 375, 376, 377, 378, 379 and 380, the indicated positions being determined by alignment with SEQ ID NO: 1.

The invention relates to the stabilized recombinant hantaviral spike of the present invention which is in solution.

The invention relates to the stabilized recombinant hantaviral spike of the present invention incorporated onto virus-like particles.

The invention relates to the stabilized recombinant hantaviral spike of the present invention incorporated into the envelope of recombinant viruses, onto pseudotype virus vectors or any non-viral system.

The invention relates to a pharmacological composition comprising the stabilized hantaviral spike of the present invention.

The invention relates to a pharmacological composition comprising the stabilized recombinant hantaviral spike of the present invention incorporated onto virus-like particles.

The invention relates to the stabilized recombinant hantaviral spike or the pharmacological composition of the present invention for use in the preparation of a medicament effective in preventing or treating hantavirus infection.

The invention relates to a method for preventing and/or treating a hantaviral infection, comprising administering to a subject in need thereof the stabilized recombinant hantaviral spike or a pharmacological composition of the present, in an amount effective to inhibit hantaviral infection of susceptible cells so as to thereby prevent or treat the infection.

The invention relates to a diagnostic agent comprising or consisting of a stabilized recombinant hantaviral spike of the present invention and an appropriate diagnostic reagent.

The invention also relates to a kit for diagnosing or monitoring, in a subject, a hantaviral infection, comprising the stabilized recombinant spike of the present invention and an appropriate diagnostic reagent.

The invention also relates to a kit for treating and/or preventing hantavirus infections, comprising the stabilized spikes or the pharmacological composition that comprise the stabilized hantaviral spikes.

The invention also relates to the use of the stabilized spikes in the generation or selection of ligands useful to treat and/or prevent hantavirus infections.

The invention also relates to the use of the stabilized spikes for the identification of epitopes recognized by ligands useful to treat and/or prevent hantavirus infection.

The invention also relates to the use of the stabilized spikes for prepare monoclonal antibodies (in the case of mice) or immunoglobulin heavy and light chains from animals immunized with the selected Gn/Gc spike mutants. The invention also relates to the use of these antibodies to measure their virus neutralizing efficacy against the infectious virus and to determine their epitopes by X-ray crystallography or by Cryo-ET.

The invention also relates to the use of the stabilized spikes for assess the survival rate of animals that are vaccinated with the wt or mutant hantaviral spikes and subsequently challenged with Andes virus. Then, by following this methodological strategy, those Gn/Gc mutants can be selected that confer highest survival rates of the animals (Hooper et al., 2001).

The invention also relates to the use of the stabilized spikes for assess the efficiency of stabilized hantaviral spikes to deplete neutralizing antibodies from patient sera. For this, patient sera with high neutralizing titer are preincubated with wt or stabilized hantaviral spikes and then mixed with infectious hantaviruses on the surface of cells. After the virus-patient sera-spike mixture is removed and virus infectivity titrated as described in Barriga et al., 2016. Alternatively, we perform virus plaque reduction assays. Using this approach, we can select those stabilized spikes that reach highest infection rates.

DETAILED DESCRIPTION OF THE INVENTION

In the present invention, the inventors were seeking to prepare improved antigens resembling the hantavirus spikes in their infectious conformation, given the high lability of the native hantaviral spikes. Therefore, a novel hantavirus Gn/Gc structure, a Gc prefusion structure and their fitting into a Cryo-EM map was used to identify inter-chain contacts in order to design the improvement of the stability of inter-chain contacts, thereby arresting them into a determined conformation, avoiding conformational changes that dynamically occur on the surface of viruses outside host cells or during the infection of cells and decreasing the lability of the virus particle. Such increased stability is crucial for vaccine design because the antigen must present epitopes that occur on infectious viruses to allow B cell stimulation and as a consequence, the production of virus neutralizing antibodies.

Therefore, the present invention comprises engineered hantaviral spikes in which the stability of spike proteins has been improved by either introducing at least one disulphide inter-chain bond and/or by at least one cavity-filling amino acids with bulky residues such as for example phenylalanine. The introduction of site-specific residue substitutions into the hantaviral spikes has been designed at inter-chain contacts of the $(Gn/Gc)_4$ heterodimer and between the $(Gn/Gc)_4$ heterodimers, consisting specifically of contacts between the Gn/Gc heterodimer, the Gc/Gc homodimer and the Gn/Gn oligomer. The advantage of stabilized spike proteins for the design of vaccines and therapeutics is given by arresting them in a conformation that resembles that of infectious hantavirus virions, thereby avoiding other conformations that are inefficient or ineffective in generating protective immune responses.

The invention refers to the stabilization of the hantaviral spike through at least one residue substitution or several substitutions at a single contact interphase or different inter-chain contact interphases, which are treated for clarity in separate embodiments, and can be used separately as well as in any combination. Based on the conserved structure of the hantavirus spike proteins said substitution characterized in the Andes virus species, can be easily transferred to analogous positions in any other species of the hantavirus family, including among others, Dobrava virus, Puumala virus, Sin Nombre virus, Hantaan virus and Seoul virus (see FIG. 1 for analogous positions).

For the design of the inter-chain contact-stabilizing residue substitutions, the present invention describes novel structures of the hantaviral spike, and novel contact interphases that allowed for the design of contact-stabilizing modifications. The secondary structure elements of these structures are summarized in FIG. 1, while the individual structures and contacts are shown in FIGS. 2-4.

The present invention relates to a stabilized improved recombinant hantaviral spike composed of at least one homodimer of mutants Gc, at least one heterodimer of a mutant Gc and a mutant Gn or at least one oligomer of mutants Gn, or a combination thereof.

Gc/Gc Homodimer

In a first aspect of the stabilized recombinant hantaviral spike of the invention, the amino acid modifications suitable to improve the hantaviral spike stability correspond to any residue at the two-fold molecular axis of the Gc/Gc homodimer, that comprise different regions of the Gc protein (see nomenclature FIG. 1). Specifically, the invention refers to amino acids comprised of the Gc strands $B_0$ (amino acids L676-P683), $H_0$ (amino acids V832-V837), $I_0$ (amino acids R951-L958) and the linker strand $H_0$ of Gc domain I and the f strand of Gc domain II comprising amino acids G838-D847 (FIG. 1; FIG. 2A,B). Preferably, any of the amino acids contained in these regions can be substituted by C (Cys, Cysteine) or any other modification such as A (Ala, Alanine), L (Leu, Leucine), V (Val, Valine), I (Ile, Isoleucine), W (Trp, Tryptophane), Y (Tyr, Tyrosine), F (Phe, Phenylalanine), P (Pro, Proline), M (Met, Methionine), S (Ser, Serine), G (Gly, Glycine), N (Asn, Asparagine), Q (Gln, Glutamine), T (Thr, Threonine), E (Glu, Glutamic acid), D (Asp, Aspartic acid), H (His, Histidine), K (Lys, Lysine) and/or R (Arg, Arginine).

The present invention relates to a stabilized recombinant hantaviral spike comprising at least one homodimer of mutants Gc having each at least one amino acid mutation (substitution) at a position selected from the group consisting of: 676, 677, 678, 679, 680, 681, 682, 683, 832, 833, 834, 835, 836, 837, 838, 839, 840, 841, 842, 843, 844, 845, 846, 847, 951, 952, 953, 954, 955, 956, 957 and 958, the indicated positions being determined by alignment with SEQ ID NO: 1.

In some preferred embodiments, at least one amino acid residue at positions 676, 677, 678, 679, 680, 681, 682, 683, 832, 833, 834, 835, 836, 837, 838, 839, 840, 841, 842, 843, 844, 845, 846, 847, 951, 952, 953, 954, 955, 956, 957 and/or 958 is substituted by an amino acid residue selected from the group consisting of: C, A, L, V, I, W, Y, F, P, M, S, G, N, Q, T, E, D, H, K and R.

According to an additional embodiment, preferred amino acids for introducing site-directed modifications correspond to E677, D679, G838, T839, S841, R951, H953 and H954. The present invention relates to a stabilized hantaviral spike comprising at least one homodimer of mutants Gc having each at least one amino acid mutation (substitution) at a position selected from the group consisting of: E677, D679, G838, T839, S841, R951, H953 and H954, the indicated positions being determined by alignment with SEQ ID NO: 1.

In a preferred embodiment, the amino acid modifications corresponds to one or more substitutions by C (Cys, Cysteine) and/or any other bulky side chain amino acid residue such as T (Tyr, Tyrosine), W (Trp, Tryptophan), M (Met, Methionine), L (Leu, Leucine) or F (Phe, Phenylalanine) and combinations thereof. In the case of C (Cys, Cysteine) substitutions, one or several disulfide bonds can covalently join the Gc monomers at their two-fold axis into Gc dimers. Said preferred stabilized Gc dimers correspond to the single substitutions G838C and/or T839C and/or H953C, and/or H953F, and/or H954C, and/or H954F, and/or the Gc double substitution Gc H953C/Q844C, H954C/Q844C, S841C/R951C, E677C/R951C, D679C/H953C and/or D679C/H954C.

In some embodiments, the stabilized recombinant hantaviral spike comprises at least one homodimer of mutants Gc selected from the group consisting of: a homodimer of mutants Gc having each the substitution G838C, a homodimer of mutants Gc having each the substitution T839C, a homodimer of mutants Gc having each the substitution H953C, a homodimer of mutants Gc having each the substitution H954C, and wherein the amino acid residues 838C, 839C, 953C and 954C are linked respectively to the amino acid residues 838C, 839C, 953C and 954C through disulphide inter-chain bonds.

In a preferred embodiment, the stabilized recombinant hantaviral spike comprises at least one homodimer of mutants Gc having each the substitution G838C, wherein the amino acid residues 838C are linked together through a disulphide inter-chain bond.

In a preferred embodiment, the stabilized recombinant hantaviral spike comprises at least one homodimer of mutants Gc having each the substitution T839C, wherein the amino acid residues 839C are linked together through a disulphide inter-chain bond.

In a preferred embodiment, the stabilized recombinant hantaviral spike comprises at least one homodimer of mutants Gc having each the substitution H953C, wherein the amino acid residues 953C are linked together through a disulphide inter-chain bond.

In a preferred embodiment, the stabilized recombinant hantaviral spike comprises at least one homodimer of mutants Gc having each the substitution H954C, wherein the amino acid residues 954C are linked together through a disulphide inter-chain bond.

In some embodiments, the stabilized hantaviral spike comprises at least one homodimer of mutants Gc selected from the group consisting of: a homodimer of mutants Gc having each the double substitution Q844C and H953C, a homodimer of mutants Gc having each the double substitution Q844C and H954C, a homodimer of mutants Gc having each the double substitution S841C and R951C, a homodimer of mutants Gc having each the double substitution E677C and R951C, a homodimer of mutants Gc having each the double substitution D679C and H953C, and a homodimer of mutants Gc having each the double substitution D679C and H954C, and wherein the each double substitution is linked respectively through disulphide inter-chain bonds between the two mutants Gc.

In some embodiments, the stabilized hantaviral spike is a homodimer of mutants Gc selected from the group consisting of: a homodimer of mutants Gc having each the substitution G838C, a homodimer of mutants Gc having each the substitution T839C, a homodimer of mutants Gc having each the substitution H953C, a homodimer of mutants Gc having each the substitution H954C, a homodimer of mutants Gc having each the double substitution H953C and Q844C, a homodimer of mutants Gc having each the double substitution H954C and Q844C, a homodimer of mutants Gc having each the double substitution S841C and R951C, a homodimer of mutants Gc having each the double substitution E677C and R951C, a homodimer of mutants Gc having each the double substitution D679C and H953C, and a homodimer of mutants Gc having each the double substitution D679C and H954C, and wherein each double substitution is linked respectively together across the dimer interface through disulphide bonds between the double substitutions in Gc.

In some embodiments, the stabilized hantaviral spike comprises at least one homodimer of mutants Gc having each the substitution H953F.

In some embodiments, the stabilized hantaviral spike is a homodimer of mutants Gc having each the substitution H953F.

In some embodiments, the stabilized hantaviral spike comprises at least one homodimer of mutants Gc having each the substitution H954F.

In some embodiments, the stabilized hantaviral spike is a homodimer of mutants Gc having each the substitution H954F.

Gn/Gc Heterodimer

In a second aspect, the invention refers to the stabilization of hantaviral spike by modifications that comprise the Gn/Gc heterodimer contacts (see nomenclature FIG. 1) and can correspond to amino acid modifications through substitution by C (Cys, Cysteine), A (Ala, Alanine), L (Leu, Leucine), V (Val, Valine), I (Ile, Isoleucine), W (Trp, Tryptophane), Y (Tyr, Tyrosine), F (Phe, Phenylalanine), P (Pro, Proline), M (Met, Methionine), S (Ser, Serine), G (Gly, Glycine), N (Asn, Asparagine), Q (Gln, Glutamine), T (Thr, Threonine), E (Glu, Glutamic acid), D (Asp, aspartic acid), H (His, Histidine), K (Lys, Lysine) and/or R (Arg, Arginine). The preferred regions of the Gn/Gc contact stabilization comprise three different contact areas which are all preferred and are here mentioned in separate embodiments.

One of the preferred embodiments refers to modifications of any amino acid residue of Gn N290-I297 comprised in Gn by: 1) the Gn linker located between helix 2 and the $A_B$ beta strand, and 2) the region spanned by the Gn $A_B$ beta strand in combination with any amino acid residue from the Gc a/b strand, comprising T729-H737. In a preferred embodiment, the amino acid modifications correspond to any C (Cys, cysteine) substitutions including Gn H294C/Gc T734C and/or Gn N290C/Gc T729C.

In some embodiment, the invention relates to a stabilized recombinant hantaviral spike comprising at least one heterodimer of mutants Gn/Gc, wherein the mutant Gn monomer comprises at least one amino acid mutation (substitution) at a position selected from the group consisting of: 281, 290, 291, 292, 293, 294, 295, 296 and 297, the indicated positions being determined by alignment with SEQ ID NO: 1, and wherein the mutant Gc monomer comprises at least one amino acid mutation (substitution) at a position selected from the group consisting of: 729, 730, 731, 732, 733, 734, 735, 736, 737 and 748, the indicated positions being determined by alignment with SEQ ID NO: 1.

In some embodiment, the stabilized recombinant hantaviral spike comprises at least one heterodimer of a mutant Gn having the substitution H294C and a mutant Gc having the substitution T734C, wherein the amino acid residues 294C and 734C are linked together through a disulphide inter-chain bond.

In some embodiment, the stabilized recombinant hantaviral spike is a heterodimer of a mutant Gn having the substitution H294C and a mutant Gc having the substitution T734C, wherein the residues 294C and 734C are linked together through a disulphide inter-chain bond.

In some embodiment, the stabilized hantaviral spike comprises at least one heterodimer of a mutant Gn having the substitution N290C and a mutant Gc having the substitution T729C, wherein the residues 290C and 729C are linked together through a disulphide inter-chain bond.

In some embodiment, the stabilized hantaviral spike is a heterodimer of a mutant Gn having the substitution N290C and a mutant Gc having the substitution T729C, wherein the residues 290C and 729C are linked together through a disulphide inter-chain bond.

In another embodiment, the modifications include any amino acid residue contained in the Gn loop between strands $D_A$ and $E_A$ that comprises Gn K85-T99 with any Gc amino acid residue either from the Gc cd loop comprising P774-T778, and/or from Gc be loop comprising C738-Y747. Preferably, the modifications correspond to C (Cys, cysteine) substitutions comprising Gn K85C/Gc P774C and/or Gn N94C/Gc V776C and/or Gn A95C/Gc Y739C and/or and/or T99C/Gc P774C.

In some embodiment, the invention relates to a stabilized recombinant hantaviral spike comprising at least one Gn/Gc heterodimer, wherein the mutant Gn monomer comprises at least one amino acid mutation (substitution) at a position selected from the group consisting of: 85, 86, 87, 88, 89, 90, 91, 92, 93, 94, 95, 96, 97, 98 and 99, and wherein the mutant Gc monomer comprises at least one amino acid mutation (substitution) at a position selected from the group consisting of: 738, 739, 740, 741, 742, 743, 744, 745, 746, 747, 774, 775, 776, 777 and 778, the indicated positions being determined by alignment with SEQ ID NO: 1.

In some embodiment, the stabilized recombinant hantaviral spike comprises at least one heterodimer of a mutant Gn having the substitution K85C and a mutant Gc having the substitution P774C, wherein the residues 85C and 774C are linked together through a disulphide inter-chain bond.

In some embodiment, the stabilized recombinant hantaviral spike comprises at least one heterodimer of a mutant Gn having the substitution N94C and a mutant Gc having the substitution V776C, wherein the residues 94C and 776C are linked together through a disulphide inter-chain bond.

In some embodiment, the stabilized recombinant hantaviral spike comprises at least one heterodimer of a mutant Gn having the substitution A95C and a mutant Gc having the substitution Y739C, wherein the residues 95C and 739C are linked together through a disulphide inter-chain bond.

In some embodiment, the stabilized hantaviral spike comprises at least one heterodimer of a mutant Gn having the substitution T99C and a mutant Gc having the substitution P774C, wherein the residues 99C and 774C are linked together through a disulphide inter-chain bond.

In some embodiment, the stabilized hantaviral spike comprises at least one heterodimer of a mutant Gn having the substitution T99C and a mutant Gc having the substitution P744C, wherein the residues 99C and 744C are linked together through a disulphide inter-chain bond.

In some embodiment, the stabilized hantaviral spike comprises at least one heterodimer of a mutant Gn having the substitution R281C and a mutant Gc having the substitution P748C, wherein the residues 281C and 748C are linked together through a disulphide inter-chain bond.

In another embodiment, the modifications include any amino acid residue comprised by Gn H203-D206 comprised in the Gn be loop in combination with any amino acid residue comprised between Gc G853-L855 located in the Gc fg loop. In a preferred embodiment, the modification corresponds to C (Cys, cysteine) substitutions comprising Gn H203C/Gc L855C and/or Gn D206C/Gc P854C.

In some embodiment, the invention relates to a stabilized recombinant hantaviral spike comprising at least one Gn/Gc heterodimer, wherein the mutant Gn monomer comprises at least one amino acid mutation (substitution) at a position selected from the group consisting of: 203, 204, 205 and 206, and wherein the Gc monomer comprises at least one amino acid mutation (substitution) at a position selected from the group consisting of: 853, 854 and 855, the indicated positions being determined by alignment with SEQ ID NO: 1.

In some embodiment, the stabilized hantaviral spike comprises at least one heterodimer of a mutant Gn having the substitution H203C and a mutant Gc having the substitution L855C, wherein the residues 203C and 855C are linked together through a disulphide inter-chain bond.

In some embodiment, the stabilized hantaviral spike comprises at least one heterodimer of a mutant Gn having the substitution D206C and a mutant Gc having the substitution P854C, wherein the residues 206C and 854C are linked together through a disulphide inter-chain bond.

Gn/Gn Homooligomer

In a further embodiment, the invention refers also to the hantaviral spike stabilization by improving Gn/Gn homooligomeric contacts (see nomenclature FIG. 1) by amino acid modifications that comprise:

The Gn be loop P192-D206 comprised between beta strands b and c of one Gn protomer in combination with the region K59-Q75 in the other Gn protomer containing the CA strand and a region comprised between the $C_A$ strand and the $D_A$ strand.

In some embodiment, the stabilized recombinant hantaviral spike comprises at least one homooligomer of a mutant Gn having at least one mutation (substitution) at a position selected from the group consisting of: 192, 192, 193, 294, 195, 196, 197, 198, 199, 200, 201, 202, 203, 203, 204, 204, 206, and a mutant Gn having at least one mutation (substitution) at a position selected from the group consisting of: 59, 60, 61, 62, 63, 64, 65, 66, 67, 68, 79, 70, 71, 72, 73, 74 and 75, the indicated positions being determined by alignment with SEQ ID NO: 1.

More preferable, the modifications correspond to single or multiple modifications in any combination, comprising residues E61-Q200. In a more preferable embodiment, modifications include residues E61 and Q200 by simple or multiple modifications such as through substitution by C (Cys, Cysteine), A (Ala, Alanine), L (Leu, Leucine), V (Val, Valine), I (Ile, Isoleucine), W (Trp, Tryptophan), Y (Tyr, Tyrosine), F (Phe, Phenylalanine), P (Pro, Proline), M (Met, Methionine), S (Ser, Serine), G (Gly, Glycine), N (Asn, Asparagine), Q (Gln, Glutamine), T (Thr, Threonine), E (Glu, Glutamic acid), D (Asp, aspartic acid), H (His, Histidine), K (Lys, Lysine) and/or R (Arg, Arginine). In a still more preferred embodiment, the modifications correspond to double residues substitutions by C (Cys, cysteine), resulting in Gn E61C/Q200C In certain embodiment, the invention refers to stabilized spike proteins that can correspond to soluble Gn and/or Gc ectodomains in solution. Such an ectodomain of Gn and/or Gc typically does not include the well-defined transmembrane anchors nor the Gn and/or Gc endodomains.

In another embodiment, the stabilized spike proteins are incorporated onto virus-like particles (VLPs).

In a further embodiment, the stabilized hantaviral spike proteins are used to pseudotype virus vectors. Said virus vector can correspond to any virus vector, such as those of the family Retroviridae, and Vesiculoviridae or any other virus family.

In another embodiment, the stabilized spike proteins are incorporated into the envelope of recombinant viruses. Said recombinant viruses can correspond to viruses from the family Hantaviridae, Vesiculoviridae, Togaviridae or any family of the Bunyavirales order, or any other family.

In another embodiment, the stabilized hantavirus spikes of the invention can include additional amino acids at their N- and C-terminals, such as those used for protein purification and/or protein sorting and/or specific enzymatic digestions and/or as part of a fusion protein. Also, the stabilized hantaviral spike proteins can include amino acid deletions at their extreme N- and C-terminals.

In another preferred embodiment, the invention refers to stabilized spike proteins codified by nucleotide sequences alone and/or a sequence incorporated into a vector (e.g. viral vectors, plasmids) where said vector is used to be introduced into a cell.

In another preferred embodiment, the invention refers to stabilized spike proteins that can be used for preventing or treating infections by one or more hantaviruses. Said spike proteins can be used for in vivo administration to induce protective immune responses. Such immune responses can include neutralizing antibodies that can be used to prevent or treat hantavirus infections.

In a further embodiment, the stabilized hantaviral spikes can be used to select ligands that block hantavirus infection.

In a preferred embodiment, said stabilized hantaviral spikes can be immobilized on any resin and/or any surface and/or any substrate and/or any other known technique for this purpose, in order to identify new ligands from libraries such as those obtained from immunoglobulin heavy and light chain libraries from B cells and/or from aptamer (oligonucleotide) libraries and/or any other libraries and/or other random ligands, including any molecule that can be selected by binding to the stabilized recombinant hantavirus spikes In another embodiment, said stabilized hantaviral spikes can be immobilized on any resin and/or any surface and/or any substrate and/or any other known technique for this purpose, in order to characterize the mode of binding of ligands such as monoclonal antibodies.

In another embodiment, the invention refers to a pharmacological composition that includes said stabilized recombinant hantaviral spike.

The terms "pharmacological composition", "vaccine composition", "immunogenic composition" and "pharmaceutical formula" are used interchangeably herein.

Advantageous said pharmacological composition further comprises a pharmaceutically acceptable excipient, diluent, adjuvant, or carrier.

As used herein, a "pharmaceutically acceptable excipient, diluent, adjuvant or carrier" includes any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, glycerol, ethanol, Ringer's solutions, dextrose solution, and 5% human serum albumin. Liposomes, cationic lipids and non-aqueous carrier such as fixed oils may also be used. Additionally auxiliary substances, such as wetting or emulsifying agents, pH buffering substances, and the like, may be present in such carrier. The use of such media and compounds for pharmaceutically active substances is well known in the art. Except insofar as any such conventional media or compound is incompatible with a therapeutic agent of the present invention, use thereof in a composition of the present invention is contemplated. The pharmaceutically acceptable carrier can be a non-naturally occurring pharmaceutically acceptable carrier.

Due to the high structural and functional conservation of the hantaviral spike proteins Gn and Gc, it is expected that the pharmaceutical composition is useful in preventing and treating the infection by viruses from the Hantaviridae family. These include classified hantaviruses such as the Andes virus, the Araraquara virus, the Bayou virus, the Bermejo virus, the Black Creek Canal virus, the Caño Delgadito virus, the Choclo virus, the Dobrava-Belgrade virus, the El Moro Canyon virus, the Hantaan virus, the Khabarovsk virus, the Laguna Negra virus, the Lechiguanas virus, the Maciel virus, the Maporal virus, the Muju virus, the New York virus, the Oran virus, the Pergamino virus, the Prospect Hill virus, the Puumala virus, the Rio Mamore virus, the Sangassou virus, the Seoul virus, the Sin Nombre virus, the Topografov virus, and the Tula virus. This genus also includes unclassified hantaviruses, such as the Asama virus, the Catacamas virus, the Cao virus, the Castelo dos Sonhos virus, the Gou virus, the Hokkaido virus, the Fusong-Mf-682 virus, the Limestone Canyon virus, the human/hrp/02-72/bra/2002 hantavirus, hantavirus CGRn8316, hantavirus CGRn9415, hantavirus Jurong, hantavirus AH09, hantavirus Z10, hantavirus Liu, the Montano virus, the Monongahela-2 virus, the Necocli virus, the Oxbow virus, the Rockport virus, the Soochong virus, and the Yuanjiang virus. This classification is in line to the established classification by the International Committee on Taxonomy of Viruses, at the moment of the priority date invoked for this invention.

In preferred embodiments, the stabilized hantaviral spike proteins and/or a pharmaceutical formula and/or pharmaceutical composition can be used in vitro (e.g. cell culture) or in vivo, preferably administering them to a living eukaryotic organism. Preferably, the eukaryotic organism is a mammal, and still more preferably, the organism corresponds to a human. The stabilized recombinant hantaviral spike of the present invention and/or the pharmacological composition, which induces neutralizing antibodies against hantaviral infection, is administered to a mammal subject, preferably a human, in an amount sufficient to prevent, treat or attenuate the severity, extent of duration of the infection by hantavirus.

The therapeutically effective amount varies depending on the subject being treated, the age and general condition of the subject being treated, the capacity of the subject's immune response to synthesize antibodies, the degree of protection desired, the severity of the condition to be treated, the particular stabilized recombinant hantaviral spike selected ant its mode of administration, among other factors. An appropriate effective amount can be readily determined by one of skill in the art. A therapeutically effective amount will fall in a relatively broad range that can be determined through routine trials.

Typically, the pharmacological composition is prepared as an injectable form (either a liquid solution or suspension) or as a solid form suitable for solution or suspension in a liquid carrier prior to injection. The preparation may be emulsified or encapsulated in liposomes for enhanced adjuvant effect.

Once formulated, the pharmacological composition may be administered parenterally, by injection, such as intravenous, intraperitoneal, intramuscular, intradermal or subcutaneous injection.

Alternative formulations suitable for other mode of administration include oral and intranasal formulations.

In a preferred embodiment, the invention uses any of the stabilized recombinant hantaviral spike proteins described above because they enable the preparation of a medicament effective in preventing or treating hantavirus infections.

The present invention also provides a method for preventing and/or treating a hantavirus infection, comprising administering to a subject in need thereof a stabilized recombinant hantaviral spike or a pharmacological composition as defined above, in an amount effective to inhibit hantavirus infection of susceptible cells so as to thereby prevent or treat the infection.

The term "treating" includes the administration of a stabilized recombinant hantaviral spike or a pharmacological composition of the present invention to a patient who has a hantavirus infection or a symptom of hantavirus infection, with the purpose to cure, heal, alleviate, relieve, alter, remedy, ameliorate, improve, or affect the hantavirus infection and/or the symptoms of the hantavirus infection.

The term "preventing" means that the progression of a hantavirus infection is reduced and/or eliminated, or that the onset of a hantavirus infection is delayed or eliminated. The invention also includes an embodiment in which the above described hantaviral spike proteins can be used for diagnostic purposes to detect hantavirus infections.

The present invention provides a diagnostic agent comprising or consisting of a stabilized recombinant hantaviral spike according to the present invention.

The present invention also provides a kit for diagnosing or monitoring, in a subject, a hantaviral infection, comprising a stabilized recombinant spike according to the present invention and an appropriate diagnostic reagent.

The appropriate diagnostic reagent is necessary for performing an assay for diagnosing or monitoring, in a subject, a hantavirus infection. The appropriate diagnostic reagent can be a solvent, a buffer, a dye, an anticoagulant.

DEFINITIONS

In the description, the residues are designated by the standard one letter amino acid code and the indicated positions are determined by alignment with SEQ ID NO: 1 corresponding to the glycoprotein precursor in which amino acids 1-650 comprise the Gn sequence while amino acids 651-1138 comprise the Gc sequence. For example, G838C is the G (Gly, Glycine) residue at position 838 of SEQ ID NO: 1. Substitutions are designated herein by the one letter amino acid code followed by the substituting residue in one letter amino acid code; G838C is a substitution of the glycine (G) residue at position 838 of SEQ ID NO: 1 with a Cysteine acid (C) residue.

By "comprises at least one substitution", it is meant that the hantaviral recombinant spike of the present invention has one or more amino acid substitutions as indicated with respect to the amino acid sequence SEQ ID NO: 1 for mutant Gc and/or mutant Gn, but may have other modifications, including with no limitation substitutions, deletions or additions of amino acid residues. The mutant Gc and/or the mutant Gn can comprise 1, 2, 3, 4, 5, 6, 7, 8, 9, 10 or all of the substitutions listed above. All of these possible combinations are specifically contemplated.

As used herein, the terms "a", "an" and "the" include plural referents, unless the context clearly indicates otherwise. As such, the term "a" (or "an"), "one or more" or "at least one" can be used interchangeably herein.

As used herein, the term "recombinant" refers to the use of genetic engineering methods (cloning, amplification) to produce the mutant hantaviral Gc and Gn.

By "stabilized hantaviral spike" or "stabilized hantaviral spike protein" it is meant a that the viral spikes have been improved concerning their thermal resistance and/or acid resistance and/or exposure of otherwise cryptic region, such as the viral Gc fusion loops.

By "Gc/Gc homodimer", it is meant a dimer of two identical recombinant hantaviral mutants Gc ectodomains proteins.

By mutant "Gn/Gc heterodimer", it is meant a dimer of a mutant Gn ectodomain having at least one amino acid substitution as defined above and a mutant Gc ectodomain having at least one amino acid substitution as defined above.

By "Gn/Gn homooligomer", it is meant a dimer of two identical mutants Gn ectodomain having each at least one amino acid substitution as listed above.

By "inter-chain bonds" it is meant a bond that is formed across an interface formed by two proteins chains, that can be identical or different.

VLP: The term VLP is an abbreviation for virus-like particle. Hantavirus VLPs are viral particles that resemble those of the native hantaviruses in both, structural and antigenic terms. This type of particle consists of a lipid bilayer membrane in which Gn/Gc glycoproteins are anchored. The VLPs used here lack other viral proteins and viral RNA, and were prepared as described in Chilean patent application CL01085-2011: by expressing viral Gn/Gc glycoproteins in 293FT cells and purifying them from the supernatant of transfected cells by ultracentrifugation.

Gc fusion loops: The Gc membrane fusion protein contains at the tip of its structure a region that inserts after Gc activation into target lipid membranes. This region is composed of three loop regions of which each exposes at least one aromatic residue (Guardado-Calvo et al., 2016).

Cryo-ET map: The term cryo-ET map is an abbreviation for cryo-electron tomography map. It refers to a three-dimensional electron density map that has been obtained by imaging technique to produce high-resolution three-dimensional views of a specimen obtained by reconstruction of series of 2D images during tilting of a grid examined by cryo-electron microscopy.

The present invention comprise among others technical features:
A stabilized hantaviral spike comprising at least one homodimer of mutants Gc, or at least one heterodimer of a mutant Gn and a mutant Gc, or at least one oligomer of mutants Gn, or a combination thereof.
A stabilized hantaviral spike according one embodiment comprises at least one homodimer of mutants Gc having each at least one amino acid mutation (substitution) at a position selected from the group consisting of: 676, 677, 678, 679, 680, 681, 682, 683, 832, 833, 834, 835, 836, 837, 838, 839, 840, 841, 842, 843, 844, 845, 846, 847,951, 952, 953, 954, 955, 956, 957 and 958, the indicated positions being determined by alignment with SEQ ID NO: 1.
The stabilized hantaviral spike according to one embodiment comprises at least one homodimer of mutants Gc is selected from the group consisting of: a homodimer of mutants Gc having each the substitution G838C (SEQ ID NO: 2), a homodimer of mutants Gc having each the substitution T839C (SEQ ID NO: 3), a homodimer of mutants Gc having each the substitution H953C (SEQ ID NO: 4), and a homodimer of mutants Gc having each the substitution H953F (SEQ ID NO: 5), wherein the amino acid residues 838C, 839C and 953C are linked respectively to the amino acid residues 838C, 839C and 953C through disulphide inter-chain bonds.
The stabilized hantaviral spike according to one embodiment, wherein each mutant Gc of the at least one homodimer of mutants Gc has the substitution G838C (SEQ ID NO: 2), wherein the amino acid residues 838C are linked together through a disulphide inter-chain bond.
The stabilized hantaviral spike according to one embodiment, wherein each mutant Gc of the at least one homodimer of mutants Gc has the substitution T839C (SEQ ID NO: 3), wherein the amino acid residues 839C are linked together through a disulphide inter-chain bond.

The stabilized hantaviral spike according to one embodiment, wherein each mutant Gc of the at least one homodimer of mutants Gc has the substitution H953C (SEQ ID NO: 4), wherein the amino acid residues 953C are linked together through a disulphide inter-chain bond.

The stabilized hantaviral spike according to one embodiment, wherein each mutant Gc of the at least one homodimer of mutants Gc has the substitution H953F (SEQ ID NO: 5).

The stabilized hantaviral spike according to one embodiment, wherein each mutant Gc of the at least one homodimer of mutants Gc has the double substitution Q844C/H953C (SEQ ID NO: 6), wherein the amino acid residues 844C and 953C are linked respectively to the amino acid residues 844C and 953C through a disulphide inter-chain bond.

The stabilized hantaviral spike according to one embodiment comprises at least one heterodimer of mutants Gn/Gc, wherein the mutant Gn monomer comprises at least one amino acid mutation (substitution) at a position selected from the group consisting of: 281, 290, 291, 292, 293, 294, 295, 296 and 297, the indicated positions being determined by alignment with SEQ ID NO: 1; and wherein the mutant Gc monomer comprises at least one amino acid mutation (substitution) at a position selected from the group consisting of: 729, 730, 731, 732, 733, 734, 735, 736, 737 and 748, the indicated positions being determined by alignment with SEQ ID NO: 1.

The stabilized hantaviral spike according to one embodiment comprises at least one heterodimer of a mutant Gn having the substitution H294C and a mutant Gc having the substitution T734C (SEQ ID NO: 7), wherein the amino acid residues 294C and 734C are linked together through a disulphide inter-chain bond.

The stabilized hantaviral spike according to one embodiment comprises at least one heterodimer of a mutant Gn having the substitution R281C and a mutant Gc having the substitution P748C (SEQ ID NO: 8), wherein the residues 281C and 748C are linked together through a disulphide inter-chain bond.

The stabilized hantaviral spike according to one embodiment at least one heterodimer of mutants Gn/Gc, wherein the mutant Gn monomer which comprises at least one amino acid mutation (substitution) at a position selected from the group consisting of: 61, 85, 86, 87, 88, 89, 90, 91, 92, 93, 94, 95, 96, 97, 98 and 99, the indicated positions being determined by alignment with SEQ ID NO: 1; and wherein the mutant Gc monomer comprises at least one amino acid mutation (substitution) at a position selected from the group consisting of: 738, 739, 740, 741, 742, 743, 744, 745, 746, 747, 748, 774, 775, 776, 777 and 778, the indicated positions being determined by alignment with SEQ ID NO: 1.

The stabilized hantaviral spike according to one embodiment comprises at least one heterodimer of a mutant Gn having the substitution T99C and a mutant Gc having the substitution P774C (SEQ ID NO: 9), wherein the residues 99C and 774C are linked together through a disulphide inter-chain bond.

The stabilized hantaviral spike according to one embodiment comprises at least one heterodimer of a mutant Gn having the substitution K85C and a mutant Gc having the substitution P774C (SEQ ID NO: 10), wherein the residues 85C and 774C are linked together through a disulphide inter-chain bond.

The stabilized hantaviral spike according to one embodiment comprises at least one heterodimer of a mutant Gn having the substitution N94C and a mutant Gc having the substitution V776C (SEQ ID NO: 11), wherein the residues 85C and 774C are linked together through a disulphide inter-chain bond.

The stabilized hantaviral spike according to one embodiment comprises at least one Gn/Gc heterodimer, wherein the mutant Gn monomer comprises at least one amino acid mutation (substitution) at a position selected from the group consisting of: 203, 204, 205 and 206, the indicated positions being determined by alignment with SEQ ID NO: 1; and wherein the Gc monomer comprises at least one amino acid mutation (substitution) at a position selected from the group consisting of: 853, 854 and 855, the indicated positions being determined by alignment with SEQ ID NO: 1.

The stabilized hantaviral spike according to one embodiment comprises at least one homooligomer of a mutant Gn having at least one mutation (substitution) at a position selected from the group consisting of: 59, 60, 61, 62, 63, 64, 65, 66, 67, 68, 69, 70, 71, 72, 73, 74 and 75; and a mutant Gn having at least one mutation (substitution) at a position selected from the group consisting of: 192, 193, 194, 195, 196, 197, 198, 199, 200, 201, 202, 203, 204, 205 and 206, the indicated positions being determined by alignment with SEQ ID NO: 1.

The stabilized hantaviral spike according to one embodiment comprises at least one homooligomer of mutants Gn having each the double substitution E61C/Q200C (SEQ ID NO: 12), wherein the amino acid residues 61C and 200C are linked respectively to the amino acid residues 61C and 200C through disulphide inter-chain bonds between the two mutants Gn.

The stabilized hantaviral spike according to one embodiment, wherein the spike is in solution.

The stabilized hantaviral spike according to one embodiment, wherein the spike is incorporated into the envelope of recombinant viruses, pseudotype virus vectors, virus-like particles or any non-viral system.

The stabilized hantaviral spike according to one embodiment, wherein the spike is incorporated onto virus-like particles.

A pharmacological composition comprising the stabilized hantaviral spike according to one embodiment.

The stabilized hantaviral spike according to one embodiment, or the pharmacological composition according to another embodiment, for use in the preparation of a medicament effective in preventing and/or treating hantavirus infection.

A method for preventing and/or treating a hantavirus infection, comprising administering to a subject in need thereof the stabilized hantaviral spike according to one embodiment or a pharmacological composition according to another embodiment, in an amount effective to inhibit hantavirus infection of susceptible cells so as to thereby prevent or treat the infection.

A diagnostic agent comprising or consisting of a stabilized hantaviral spike according to one embodiment and an appropriate diagnostic reagent.

A kit for diagnosing or monitoring, in a subject, a hantaviral infection, comprising the stabilized spike according to one embodiment and an appropriate diagnostic reagent.

A kit for treating and/or preventing hantavirus infections, comprising the stabilized spikes according to one embodiment or the pharmacological composition according to another embodiment.

Use of the stabilized spikes according to one embodiment, in the generation or selection of ligands useful to treat and/or prevent hantavirus infections.

Use of the stabilized spikes according to one embodiment, for the identification of epitopes recognized by ligands useful to treat or prevent hantavirus infections.

BRIEF DESCRIPTION OF THE SEQUENCES

SEQ ID NO: 1: Sequence corresponding to the wild type glycoprotein precursor of Orthohantavirus Andes GenBank accession number AA086638.1. This precursor sequence comprises glycoprotein Gn within amino acids 1-651 and glycoprotein Gc within amino acids 652-1138.

SEQ ID NO: 2. Sequence corresponding to the single amino acid substitution Gc G838C in SEQ ID NO: 1.

SEQ ID NO 3: Sequence corresponding to the single amino acid substitution Gc T839C in SEQ ID NO: 1.

SEQ ID NO 4: Sequence corresponding to the single amino acid substitution Gc H953C in SEQ ID NO: 1.

SEQ ID NO 5: Sequence corresponding to the single amino acid substitution Gc H953F in SEQ ID NO: 1.

SEQ ID NO 6: Sequence corresponding to the double amino acid substitution Gc Q844C/H953C in SEQ ID NO: 1.

SEQ ID NO 7: Sequence corresponding to the double amino acid substitution Gn/Gc H294C/T734C in SEQ ID NO: 1.

SEQ ID NO 8: Sequence corresponding to the double amino acid substitution Gn/Gc R281C/P748C in SEQ ID NO: 1.

SEQ ID NO 9: Sequence corresponding to the double amino acid substitution Gn/Gc T99C/P744C in SEQ ID NO: 1.

SEQ ID NO 10: Sequence corresponding to the double amino acid substitution Gn/Gc K85C/P774C in SEQ ID NO: 1.

SEQ ID NO 11: Sequence corresponding to the double amino acid substitution Gn/Gc N94C/V776C in SEQ ID NO: 1.

SEQ ID NO 12: Sequence corresponding to the double amino acid substitution Gn/Gn E61C/Q200C in SEQ ID NO: 1.

BRIEF DESCRIPTION OF FIGURES

FIG. 1. Secondary structure elements of the hantaviral spike structure.

Multiple sequence alignment of the Gn/Gc proteins of pathogenic hantaviruses compared to hantaviruses harbored in insectivores. FIG. 1 shows the amino acid sequences for hantavirus isolates ANDV (SEQ ID NO:1); SNV (SEQ ID NO: 13); PUUV (SEQ ID NO:14); DOBV (SEQ ID NO:15); HNTV (SEQ ID NO: 16); SEOV (SEQ ID NO: 17); LOQV (SEQ ID NO: 18) and ASAV (SEQ ID NO: 19). The Gn/Gc glycoproteins are synthesized as glycoproteins precursor that is cleaved by a host protease into the N-terminal Gn and the C-terminal Gc glycoproteins, at the signal sequence "WAASA". Strictly conserved and highly similar residues are highlighted in grey. The secondary structure elements obtained from the Gn/Gc crystal structure of Andes virus are displayed above the sequences. For regions missing structural information (to be included). Disulfide bonds are indicated with light grey numbers below the sequence alignment.

A) Top view of the Hantaan virus Gc homodimer structure. To improve visibility, the human single-chain variable domain (scFv) antibody was removed from the Gc/scFv A5 structure complex. One Gc protomer is highlighted in black, while the other is indicated in grey. B) Side view of the Gc homodimer structure. C) Insert showing the Gc/Gc homodimer contacts where the different regions forming the contacts are highlighted. D) Multi-angle light scattering (MALS) of the soluble Gc ectodomain of Hantaan virus used to obtain the Gc crystal structure.

Figure 3:
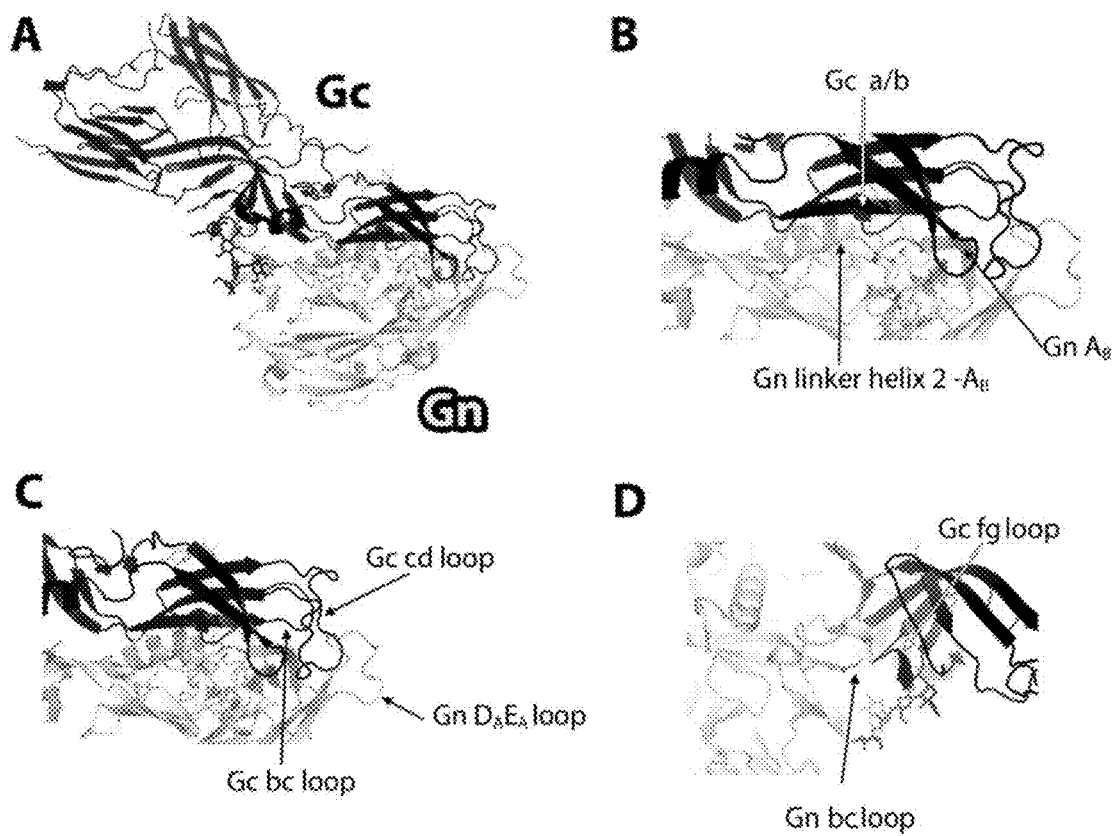

FIG. 3. The structure of hantavirus Gn/Gc heterodimer and identification of Gn/Gc heterodimer contacts.

A) Side view of the Andes virus Gn/Gc heterodimer structure. The Gn protomer is indicated in white, the Gc protomer in black. B-D) Inserts showing the different Gn/Gc contacts in which the different regions forming the contacts are highlighted.

Figure 4:
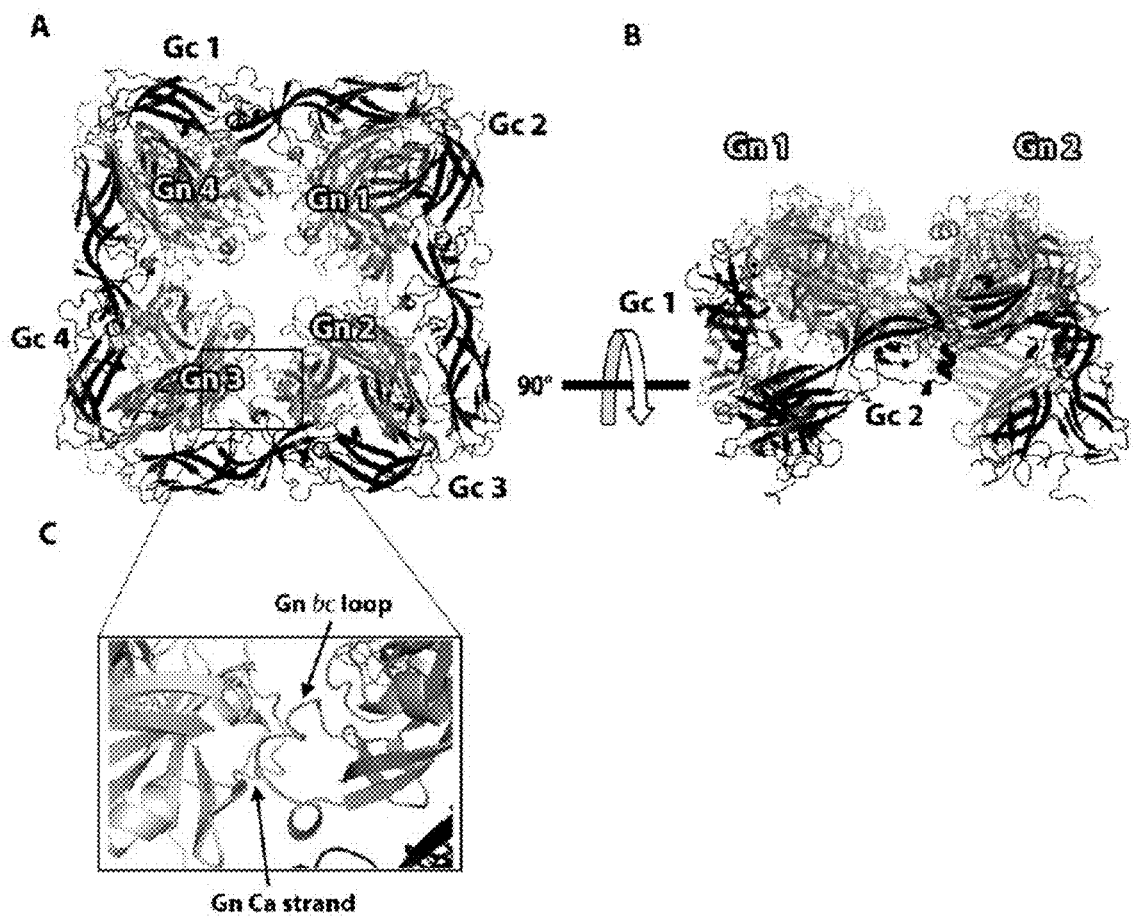

FIG. 4. Fitting of the Gn/Gc structure into the Tula hantavirus Cyro-ET map and identification of Gn/Gn contacts.

A) Top view of four Gn/Gc heterodimer structures fitted into the available Cryo-ET map for the Tula hantavirus spike (Shi et al., 2016). Gn is indicated in white, Gc is indicated in black. B) Side view of two Gn/Gc heterodimers fitted into the spike density of the Tula hantavirus Cryo-ET map. C) Insert showing different Gn/Gn contacts in which the different regions forming the contacts are highlighted.

Figure 5:
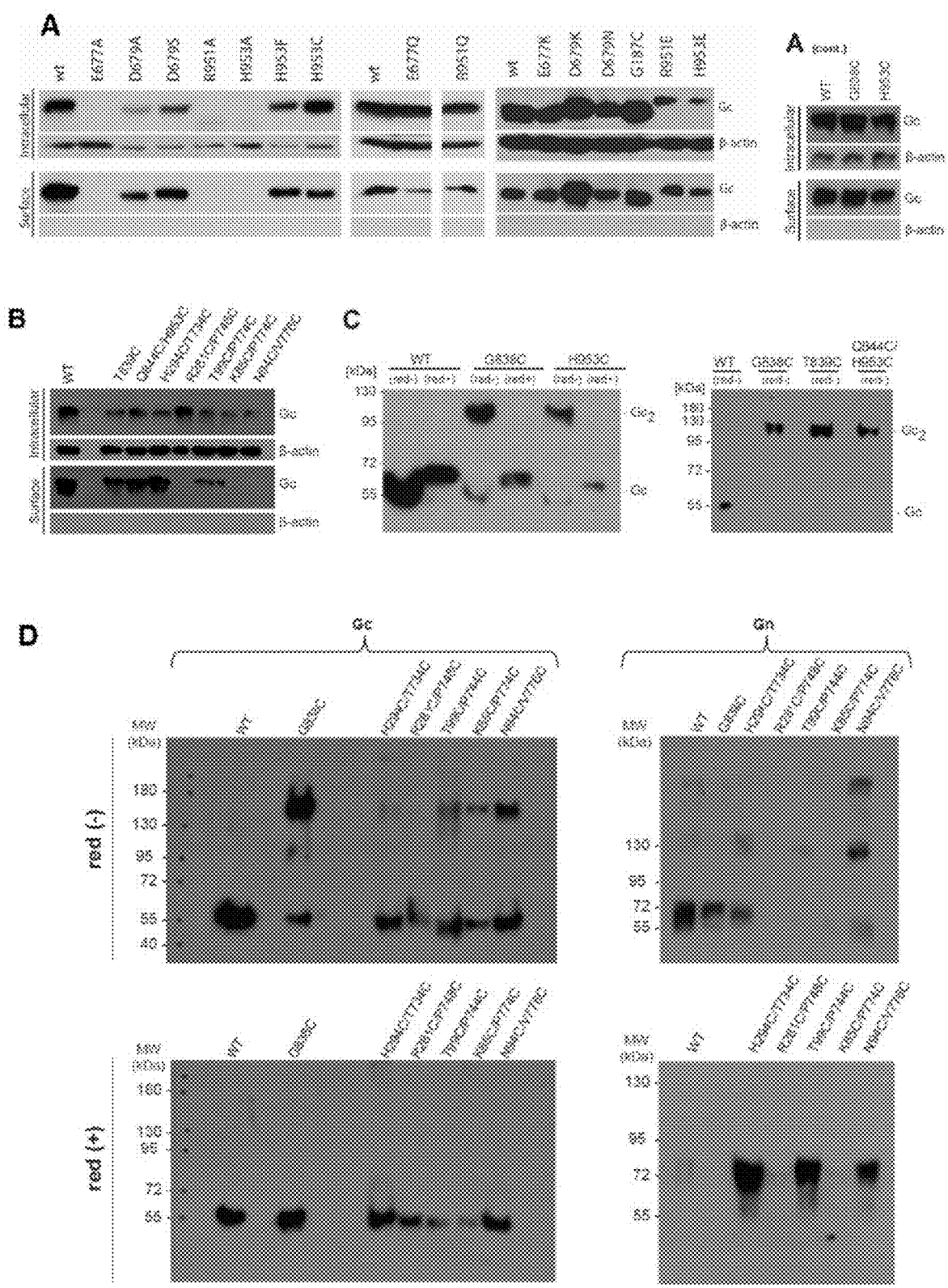

FIG. 5. Characterization of Gn/Gc mutants expression and of their assembly into VLPs bearing the engineered disulfide bonds.

(A-B) Characterization of the expression yields and cellular localization of ANDV Gn and Gc proteins that comprise either single mutation at the Gc homodimer interface (A), or double mutations at the Gc homodimer interface, or double mutations at the Gn/Gc interface of the Gn/Gc spikes (B). Western blot analysis using anti-Gc or anti-β-actin MAbs of different cellular fractions obtained from 293FT cells expressing wild type (wt) or mutant Gn/Gc after cell surface biotinylation. The fractions correspond to the non-biotinylated fraction (intracellular proteins) or the biotinylated fraction (surface proteins). C) SDS Page and western blot under reducing and non-reducing conditions of VLPs bearing wt or mutant Gn/Gc spikes comprising single or double cysteine substitutions at the Gc homodimer interphase. using anti-Gc antibody. D) SDS Page and western blot under reducing and non-reducing conditions of VLPs bearing wt or mutant Gn/Gc spikes comprising double cysteine mutations at the Gn/Gc heterodimer interface: H294C/T734C, R281C/P748C, T99C/P744C, K85C/P774C or N94C/V776C using either anti-Gc (left panel) or anti-Gn specific antibodies (right panels). VLPs bearing wt Gn/Gc spikes were used as a negative control for disulfide bond formation, while VLPs bearing Gn/Gc spikes comprising the single mutant G838C at the Gc homodimer interface was used as a positive control for disulfide bond formation of Gc homodimers.

Figure 6:
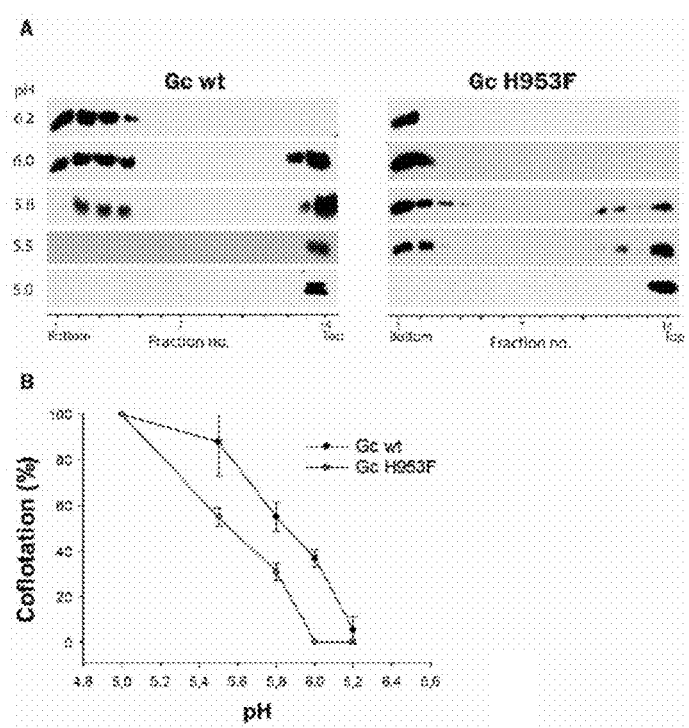

FIG. 6. Acid stability of wt and mutant hantaviral spikes.

A) Liposome co-flotation assay to visualize acid-induced activation and membrane insertion of VLPs bearing wt Gn/Gc spikes or Gn/Gc spikes comprising the single mutation H953F at the Gc homodimer interface. VLPs were incubated with liposomes at different pHs at 37° C. and the mixture was floated on a step gradient. Fractions taken consecutively from the bottom of the step gradient were examined for the presence of VLPs western blot using anti-Gc MAb. B) Quantification of the presence of wt and mutant VLPs in the fractions of the co-flotation assay. Results from at least n=3 independent experiments were averaged.

Figure 7:
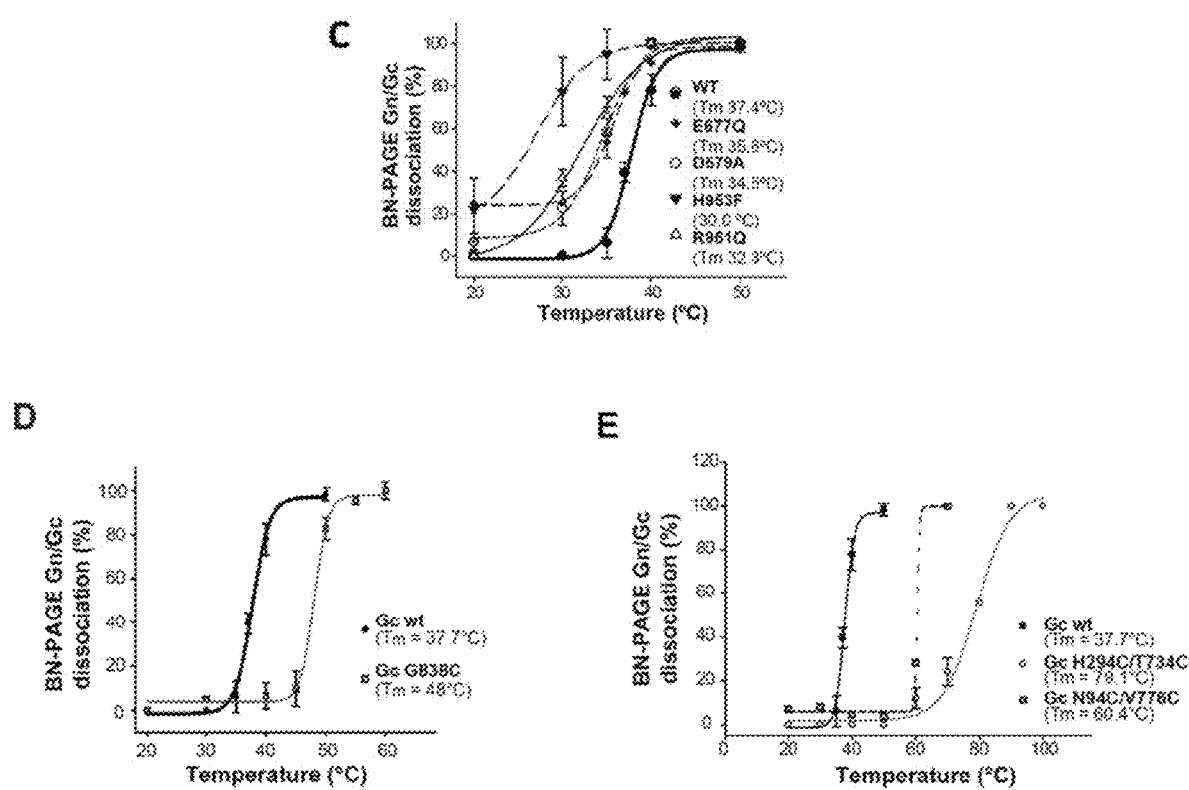

FIG. 7. Thermal stability of wt and mutant detergent-solubilized hantaviral spikes.

A-B) The Oligomeric state of the detergent-solubilized hantaviral spikes at different temperatures. Blue native-PAGE and western blot analysis of detergent solubilized VLPs displaying wt or mutant spikes including single Gc mutants at the Gc:Gc interface (A) or double mutations at the Gn/Gc interface (B). The spikes were extracted from VLPs by Triton X-100 and treated at the indicated temperatures of 20-60° C. at neutral pH. The presence of Gn or Gc in each lane was detected by western blot analysis by splitting the transferred gel in two parts and revealing with anti-Gn (left panel) and anti-Gc (right panel) antibodies. As internal control for Gc species migration, Gc wt homotrimers were examined in each gel by treatment of VLPs at pH 5.5. To further estimate the oligomerization species of Gn and Gc (indicated on the left side of the blot), the migration of their monomeric and multimeric forms was compared with a native protein standard (indicated on the right side of the blot). (C-E) Graph of the temperature-induced Gn/Gc dissociation of detergent solubilized spikes quantified by densitometry from wt, or (C) mutants at the Gc homodimer interface that do not improve the spike stability, (D) the Gc mutant G838C at the Gc homodimer interface and (E) Gn/Gc mutants at the Gn/Gc interface. Averages±s.d. are shown. The curves were fitted using a sigmoidal equation. The melting temperature (Tm) of the detergent-solubilized spikes is indicated for each mutant.

Figure 8:
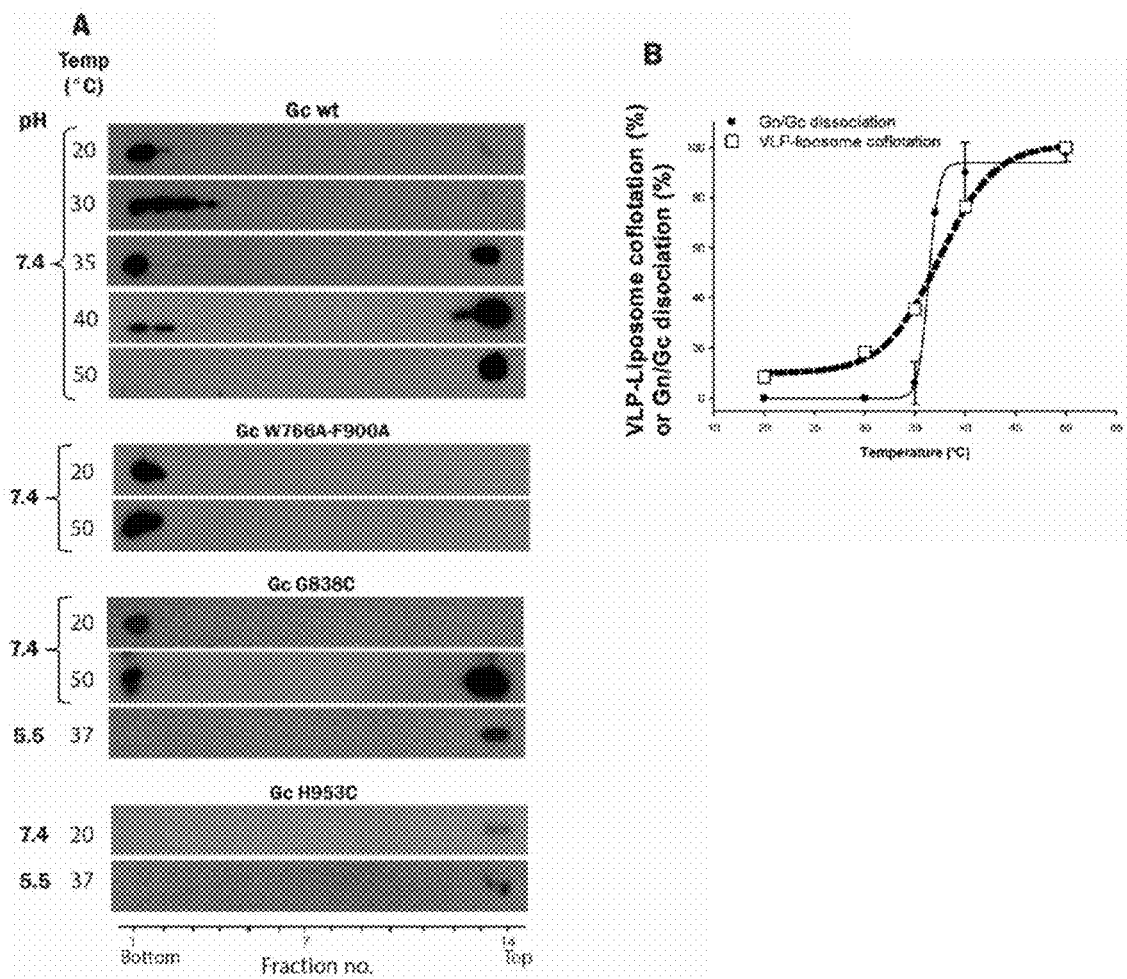

FIG. 8. Exposure of the Gc fusion loop of wt and mutant hantaviral spikes.

(A) Liposome co-flotation assay to determine the exposure of the Gc fusion loops and their insertion into membranes. VLPs were incubated with liposomes at different temperatures and pHs and the mixture floated on a step gradient and the presence of VLPs examined in each fraction by western blot using anti-Gc MAb. The double Gc fusion loop mutant W766A/F901A, that does not insert into target membranes was used as negative control. (B) Fusion loop exposure temperature compared to the melting temperature of wt Gn/Gc spikes versus mutant spikes assembled onto VLPs. The quantification of the fraction of Gc interacting with liposomes at different temperatures, superimposed to the fraction of dissociated Gc at the same temperatures. Results from at least n=3 independent experiments were averaged.

Figure 9:
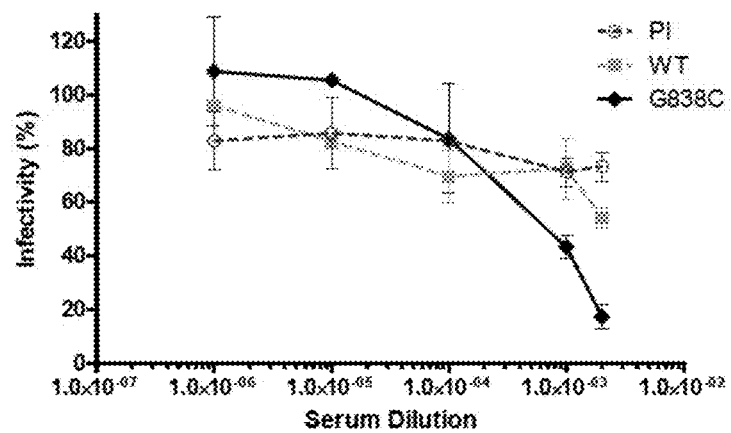
Figure 9:
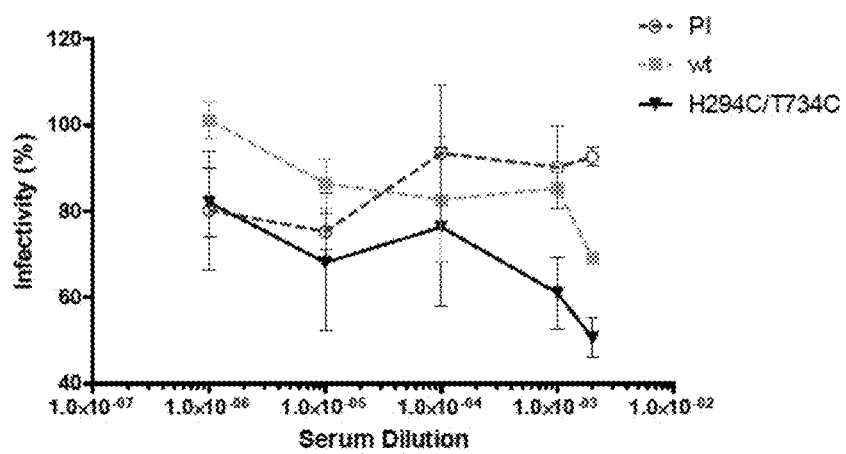

FIG. 9. Neutralizing antibody responses against VLPs bearing wild type or mutant hantaviral spikes in mice.

(A-B) Neutralizing activity of sera from Balb/c mice after the immunizations with VLPs bearing wt or mutant hantaviral spikes comprising either the single mutant G838C at the Gc homodimer interface (A) or comprising the double mutation H294C/T734C at the Gn/Gc heterodimer interface. Neutralization of Andes virus was assessed through incubation of ANDV with sera from mice for 1 hr and subsequent adsorption to Vero E6 cells that were immunized with VLPs bearing wt or mutant hantaviral spikes. As a control, sera of mice immunized with VLPs bearing wt Gn/Gc were used as well as sera from mice before immunization. Infection was quantified by flow cytometry 16 h post-infection using anti-ANDV nucleoprotein antibody.

EXAMPLES

Example 1. The Selection and Design of Amino Acid Modifications for Improved Stability of the Hantaviral Spike In order to face the technical challenge to improve the spike stability, for the generation of improved immunogens, we used structural information to identify and select key positions and regions in the hantaviral spikes that allow the design of sequence modifications for their stabilization.

The molecular structures of the ectodomains of the hantavirus Gn and Gc proteins have been described in their monomeric conformations; however information was still missing concerning their orientation in the hantaviral spike and their molecular contacts for a molecular perspective on their assembly and the design of preventive or therapeutic strategies.

In the present example, the inventors have obtained novel molecular structures that describe the contacts of the Gn/Gc assembly. Among these structures, two particular structures have been obtained from two different expression constructs stably transfected into *Drosophila* S2 cells:
 a) expression plasmid pMT-rGc-W115H coding the recombinant Gc ectodomain (rGc) (residues 652-1107) including the W115H mutation and two C-terminal strep-tag sequences separated by a (GGGS)3 linker preceded by an enterokinase cleave site as previously described (Guardado-Calvo et al., 2016).
 b) expression plasmid pMT-rGn-Gc coding for the recombinant Gn (rGn) (residues 21-374) and rGc (residues 652-1107) ectodomains connected by a 42 amino acids flexible linker region and two C-terminal strep-tag sequences separated by a (GGGS)3 linker preceded by an enterokinase cleave site as previously described (Guardado-Calvo et al., 2016).

The expression products were purified and crystallized for subsequent X-ray diffraction by standard methods. In the case of rGc, we crystallized this protein by previous incubation with human single-chain variable domain (scFv) antibody fragment A5 as previously described (Guardado-Calvo et al., 2016).

Figure 2:
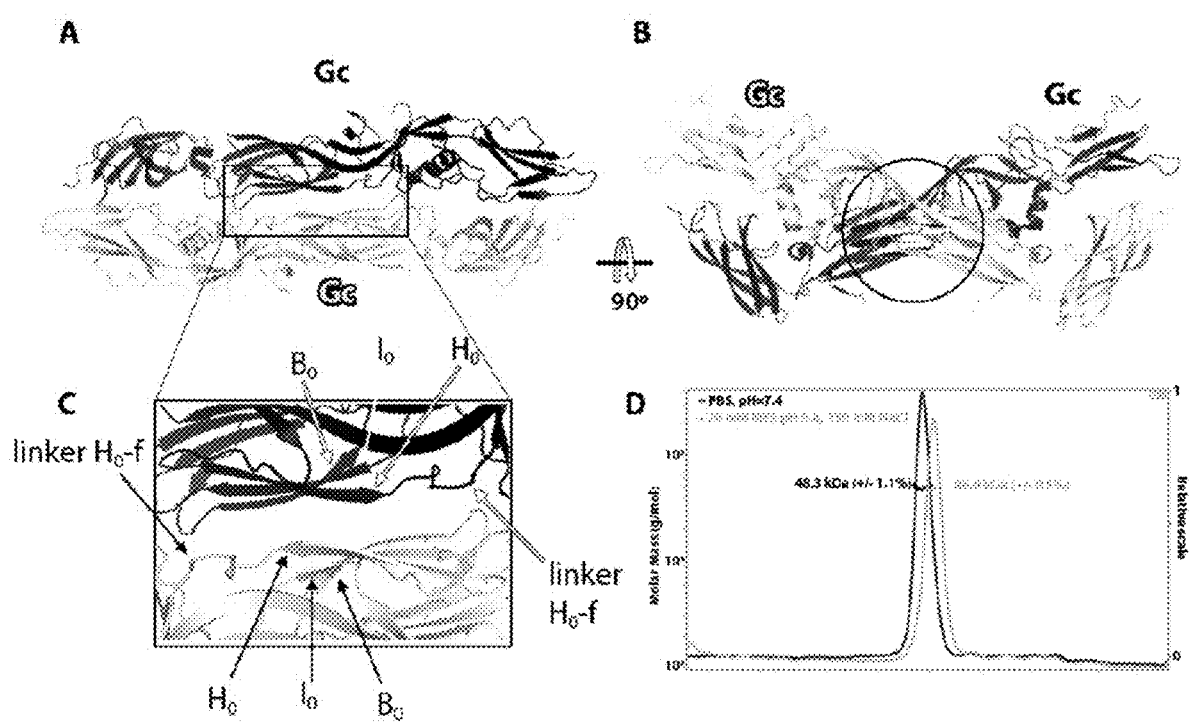
FIG. 2. The structure of hantavirus Gc and identification of Gc/Gc homodimer contacts.

We determined the Gc crystal structure at 3.0 Å resulting in a Gc homodimer (FIG. 2) while we were able to reveal the Gn/Gc crystal structure at 2.7 Å (FIG. 3). The structures allowed us to identify the molecular contacts between the Gc/Gc homodimer and the Gn/Gc heterodimer. When we further fitted the Gn/Gc crystal structure into the available 16 Å resolution electron cryo-tomography reconstruction of Tula hantavirus (Shi et al., 2016), we could also define contacts of the Gn/Gn homooligomers (FIG. 4).

In this context, we selected preferred amino acids for modifications by the following criteria:
 a) forming the contact interphase between the Gc/Gc homodimer, Gn/Gc heterodimer and Gn/Gn homooligomer.
 b) cavity filling mutants.

Among these amino acids, we selected those for modifications that fulfilled at least one of the following criteria:
 a) The impact of the mutation in the structure to avoid protein missfolding.
 b) The conservation of the residue.
 c) The certainty of the residue position in the model based on the observed electron density.
 d) For the design of inter-chain bonds, the distances between the $C_{alpha}$-$C_{alpha}$ atoms should be less than 6.5 Å and for $C_{beta}$-$C_{beta}$ atoms less than 4.5 Å.
 e) For inter-chain disulfide bonds, the quality of the modeled disulphide bond is evaluated using the dihedral angles $C_i^{beta}$-$S_i$-$S_j$-$C_j^{beta}$, $C_i^{alpha}$-$C_i^{beta}$-$S_i$-$S_j$, and $C_j^{alpha}$-$C_j^{beta}$-$S_j$-$S_i$.
 f) For the design of cavity filling mutants, residues were selected with improved affinity score (improved ΔG) by Rosetta.

Figure 1:
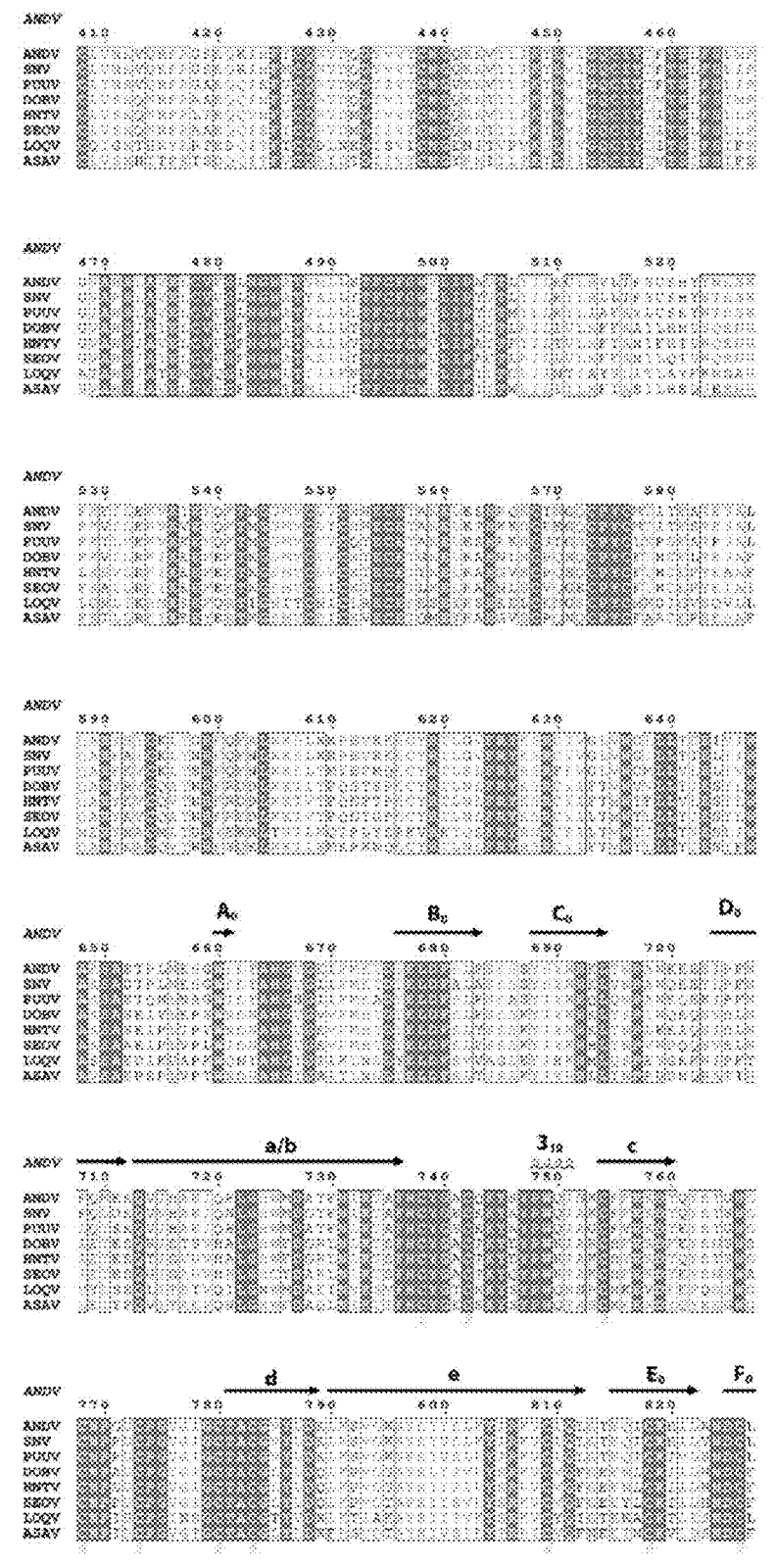
Figure 1:
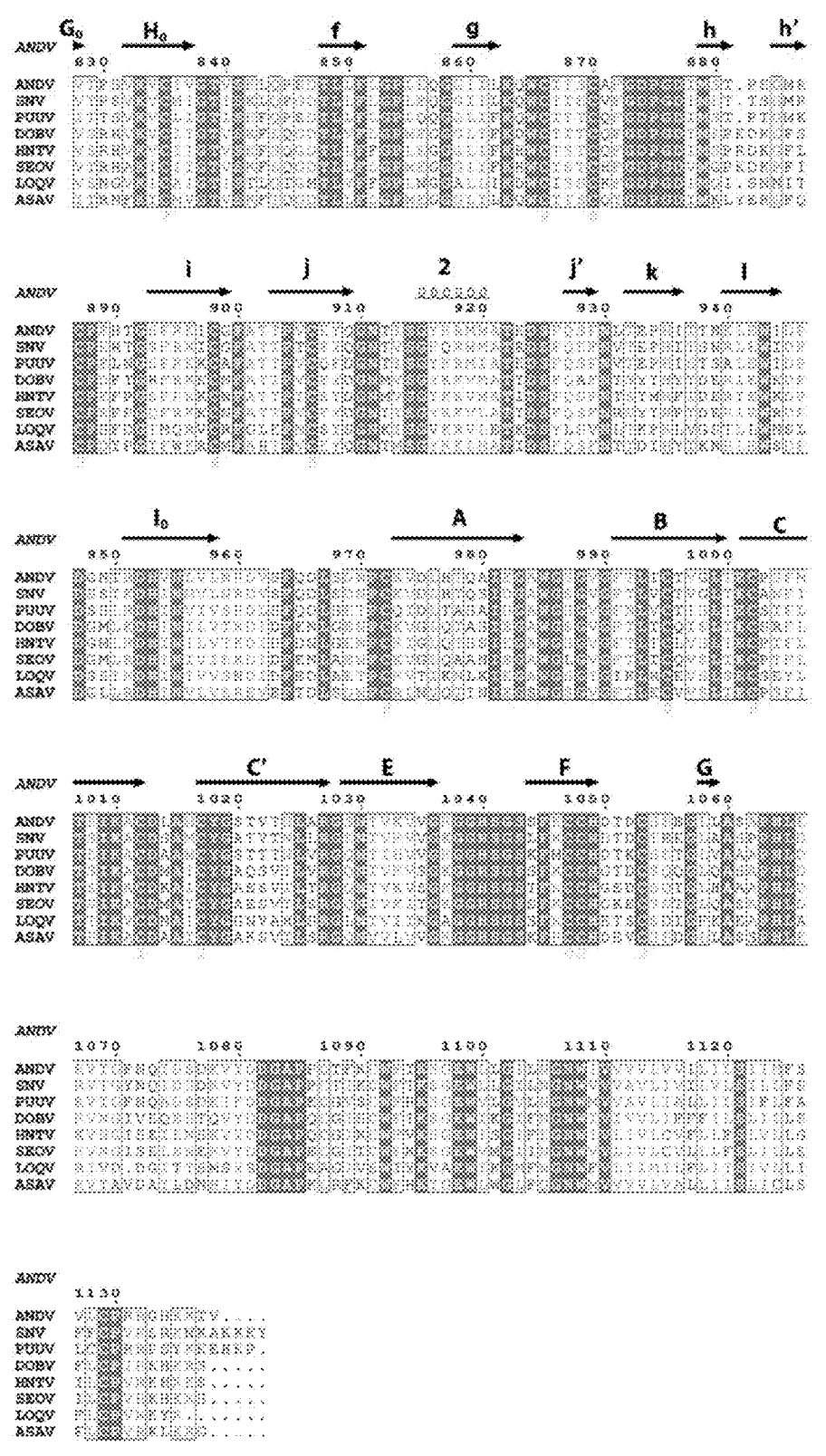

To highlight the different selected amino acids, we refer to the Andes virus sequence nomenclature as identified in FIG. 1. However, since the structure and sequences of the glycoproteins is highly conserved between hantaviruses (Guardado-Calvo et al., 2016; Wilensky et al., 2016; Shi et al., 2016), the contacts that we observe in the Andes virus and Hantaan virus Gn/Gc structures, can be extended to any Gn/Gc protein of the Hantaviridae family.

For the ease of understanding, we called each region as we could derive it from the secondary elements in the structure. If hence a region is contained in a beta strand, we termed this region following the strand nomenclature; e.g. "b strand". When a region is contained between two beta strands, for example between beta strand b and c, we termed this region "bc linker" or "bc loop" according to its structural features.

From these overall criteria, we selected the following possible amino acids for modifications. Among them, the amino acid modification can correspond to any amino acid substitution, including Ala, Leu, Val, Ile, Trp, Tyr, Phe, Pro, Met, Ser, Cys, Sec, Gly, Asn, Gln, Thr, Glu, Asp, His, Lys and/or Arg:

(1) The Gc/Gc Homodimer

The Gc/Gc homodimer contacts spanning amino acids comprised of the Gc strands $B_0$ (residues 1676-P683), $H_0$ (residues V832-V837), $I_0$ (residues R951-L958) and the Hof linker region between strand $H_0$ of Gc domain I and the f strand of Gc domain II comprising amino acids G838-D847. For clarity, please see FIG. 1 and FIG. 2.

This list of amino acid regions resulted in the preferred amino acids: Gc E677, D679, G838, T839, S841, R951 and/or H953 and the contact pairs Gc E677/R951, D679/H953 and/or H953C/Q844C.

In our preferred realization, the modifications correspond to Cys substitutions to form inter-chain disulfide bonds through the following amino acid substitutions: G838C, T839C, S841C/R951C, E677C/R951C, D679C/H953C and/or Q844C/H953C. A preferred cavity filling mutant includes H953F.

(2) The Gn/Gc Heterodimer

The Gn/Gc heterodimer contacts comprising (FIG. 1, FIG. 3):
A) Any Gn amino acid from the helix 2-$A_B$ linker region and $A_B$ strand comprising residues N290-I297 in combination with any residue from the Gc a/b strand, comprising residues T729-H737.
B) Any amino acid from the Gn $D_A E_A$ loop comprising residues K85-T99 with any Gc amino acid either from the Gc cd loop comprising P774-T778, and/or from Gc bc loop comprising C738-Y747.
C) Any amino acid from the Gn bc loop comprising H203-D206 in combination with any amino acid comprised by the Gc fg loop spanning residues G853-L855.

This list of amino acid regions resulted in the preferred amino acids:
Gn K85, N94, A95, T99, H203, D206, N290 and/or H294 and/or Gc T734, T729, P774, V776 Y739, P774, Gc L855 and/or P854. From those, we established the following contact pairs: Gn H294/Gc T734, Gn N290/Gc T729, Gn K85/Gc P774, Gn N94/Gc V776C, Gn A95/Gc Y739, T99/Gc P774, Gn H203/Gc L855 and/or Gn D206/Gc P854.

In our preferred realization, the amino acid modifications correspond to Cys substitutions to form inter-chain disulfide bonds through the following amino acid substitutions: Gn H294C/Gc T734C, Gn N290C/Gc T729C, Gn K85C/Gc P774C, Gn N94C/Gc V776C, Gn A95C/Gc Y739C, T99C/Gc P774C, Gn H203C/Gc L855C and/or Gn D206C/Gc P854C.

(3) The Gn/Gn Homooligomer

The Gn/Gn homooligomer contacts, comprising (FIG. 1, FIG. 4):
A) Any amino acid of the Gn be loop comprising residues P192-D206 of one Gn protomer in combination with any amino acid modification in the Gn region K59-Q75 comprising the CA strand and the region comprised between the CA strand and the DA strand in the other Gn protomer.

This list of amino acid regions resulted in the preferred amino acids: Gn E61, Q200 From which we established the following contact pair: Gn E61/Q200.

In our preferred realization, the amino acid modifications correspond to Cys substitutions to form inter-chain disulfide bonds through the following amino acids substitutions: E61C/Q200C.

Based on the results shown in this example, we identified several key positions and regions that allowed the proposal of specific sequence modifications in such key positions and regions for the design of recombinant hantaviral spikes in order to improve their stability.

Example 2. Expression and Folding of Hantaviral Spike Mutants

The present example of the invention provides information on how the inventors experimentally assess whether the design of recombinant hantaviral spikes are expressed and properly folded in cells.

In this example we used the plasmid pl.18/GPC coding for the Gn/Gc glycoproteins of Andes orthohantavirus CHI-7913 isolate GenBank accession number AAO86638.1 (Cifuentes-Muñoz et al., 2010) as a model for all hantaviral Gn/Gc coding plasmids and introduced nucleotide mutations using standard oligonucleotide-based PCR amplification technique.

The expression and folding of each mutant construct was assessed by transient transfection of 293FT cells (Invitrogen) and subsequent biotinylation of cell surface proteins as previously described (Guardado-Calvo et al., 2016). The presence of the Gn/Gc proteins in the biotinylated (cell surface proteins) and non-biotinylated fractions (intracellular proteins) was tested by western blot using the MAb anti-Gc 2H4/F6. The empty pl.18 plasmid was used as negative control. In FIG. 5A the inventors show an example of Gn/Gc single mutants in which the Gc/Gc contacts were modified to stabilize or to weaken the hantaviral spikes. For these mutants the inventors found different expression levels, ranging from high expression levels (H953C, E677Q, R951Q, E677K, D679K, D679N, G838C) to low (D679A, D679S, H953D, R951E, H953E) and non-detectable (E677A, R951A, H953A) (FIG. 5A). The Gc mutants that we detected in the intracellular fraction trafficked all to the plasma membrane, confirming that they could exit the ER and enter the secretary pathway of the cell, a measure for proper protein folding (FIG. 5A, surface fraction). As example of the expression yields and cellular localization of double mutations in the hantavirus spike at the Gc/Gc or Gn/Gc heterodimer interfaces, the inventors used the same approach. Although expression yields were found to be lower in all cases compared to wt (FIG. 5B, intracellular fraction), most mutants were independently detected at the plasma membrane (Q844C/H953C, H294C/T734C, T99C/P774C, N294C/V776C) (FIG. 5B, surface fraction), confirming their proper folding and cell trafficking. Hence, these mutants can be used for further analysis of the hantaviral spike characterization and are candidate antigens for vaccine design or for the selection of antiviral compounds.

With the above techniques, the inventors also introduced other amino acid modifications at additional residue positions. For the following residue substitutions the inventors obtained high expression levels and proper trafficking:
Gc homodimer single mutant GcT839C and Gc double mutant Gc Q844C/Gc H953C.
Gn/Gc heterodimer double mutants: Gn H294C/Gc T734C; Gn R281C/Gc P748C; Gn T99C/Gc P774C and Gn N94C/Gc V776C.
Gn/Gn homodimer double mutants: Gn E61C/Q200C.
To detect Gn mutant proteins, the by us well-established anti-Gn MAb 6B9/F5 was used.

In this example, the Gn/Gc wt and mutant proteins were expressed in their full length and can be harvested from the cell supernatant in form of virus-like particles. Alternatively, those of skill in the art can also express the Gn/Gc proteins as soluble ectodomains in which the transmembrane anchors and stem regions have been removed as described in Example 1. Also, Gn/Gc proteins can be used to pseudotype virus vectors or to produce recombinant viruses as it has been well described in the field (Ray et al. 2009; Cifuentes-Muñoz et al., 2010; Kleinfelter et al., 2015).

With the expressed Gn/Gc proteins, the inventors obtained well expressed recombinant hantavirus Gn/Gc proteins, that were incorporated onto virus-like particles.

Example 3. Assessment of Inter-Chain Disulfide Bonds in Hantaviral Spikes

In this examples, the inventors provide evidence, that the Gn/Gc proteins that contain amino acid substitutions by Cys, are close enough on the viral particles to allow the formation of disulfide bonds across the different Gc/Gc and Gn/Gc interfaces.

To improve the hantaviral Gc spike stability, we have designed several inter-chain disulfide bonds between Gc/Gc homodimers, Gn/Gc heterodimers and Gn/Gn homooligomers (see Example 1) based on the Gn/Gc and Gc/Gc crystal structures and Gn/Gc structure fitting into the Cryo-EM density map (Shi et al., 2016). Some inter-chain disulfide bonds may involve the substitution of single residues in each monomer (for example the substitutions Gc G838C) since in such case these residues are facing each other at the center of the 2-fold axes of the Gc homodimer. In other cases, we have designed a pair of Cys substitutions of residues that are opposing each other at any of the homodimer and/or heterodimer contact interphases to establish disulfide inter-chain bonds.

By way of example, the following hantaviral Gc/Gc spike mutants have been used to functionally assay the formation of such inter-chain disulfide bonds; Gc single mutants G838C, T893C, and Gc H953C and Gc double mutant Q844C/H953C (FIG. 5C). Therefore, we concentrated the wt and mutant VLPs from 293FT cells expressing these mutants (FIG. 5A) and subjected them to SDS PAGE and western blot analysis under reduced and non-reduced conditions. In the case of the addition of p-Mercaptoethanol (reducing condition), we found that all mutants migrated as the wt Gc protein (~50 kDa). However, in absence of a reducing agent, all Gc mutants migrated with a molecular weight that corresponds to the predicted weight of Gc dimers (~100 kDa) (FIG. 5C).

In the same way of example, the same approach was performed with double mutations of the Gn/Gc heterodimer interface; H294C/T734C; R281C/P748C; T99C/P774C; K85C/P774C and N94C/V776C. Under reducing conditions, the Gc mutants migrated at the wt Gc protein (~50 kDa) while the Gn mutants migrated as the wt Gn protein (~70 kDa) (FIG. 5D, lower panels). However, under non-reducing conditions, additional migration species were recognized by both, anti-Gn and anti-Gc antibodies, with a molecular weight of (~130 kDa) that corresponds to the Gn/Gc heterodimer (FIG. 5D, upper panels).

Together, in this example the inventors have shown that the cysteine substitution mutants at the Gc/Gc and Gn/Gc interface can be disulfide linked in a biological context, thereby forming Gc/Gc or Gn/Gc dimer linkage at the surface of viral particles. Hence, the residues forming the Gc dimer contacts in the X-ray structure of a pre-fusion form of Gc and the Gn/Gc contacts in the X-ray structure of the Gn/Gc heterodimer are proximal enough to each other on viral particles to allow for disulfide formation while still forming VLPs. This data also supports the biological relevance of the crystallographic structures proposed in Example 1 of this invention.

Example 4. Improved Acid Stability of the Hantaviral Spikes

In this example, the inventors provide evidence, that bulky residue substitution at the Gc/Gc dimer interface can increase the resistance to different environmental factors, such as mild acidification. This is an import aspect since the administration of antigens to individual involves their suspension into immunologic adjuvants to improve immune responses. Yet, the most frequently used antigens, alum adjuvant in humans and Freund adjuvant in animals, have acidic pH that can perturb the antigen structure. This is of particular importance for the hantaviral spike, since already a mildly acidic pH activates the hantavirus Gc fusion protein inducing its non-infectious post-fusion conformation. Thus, in a preferred embodiment, it is desirable to improve the hantaviral spike stability not only in terms of their inter-chain contacts, but also in terms of their resistance to acidic pH.

In this invention His residues were substituted since they are molecular sensors of mildly acidic pH, having an acid dissociation constant (plc) of ~6.0, coinciding with the pH range of Gc activation. In this context, the inventors have designed and characterized one Gc mutant in which they have substituted His953, located at the Gc homodimer interphase, to Phe (H953F) (FIG. 5A). To functionally assess its activation pH compared to wt Gn/Gc, we performed a liposome coflotation assay as a measure for activation by fusion loop exposure and membrane insertion established previously (Guardado-Calvo et al., 2016). Therefore we incubated VLPs bearing the wt or mutant spike H953F with fluorescently labeled liposomes at each pH and loaded the mixture to the bottom of a sucrose step gradient. After centrifugation, we monitored each fraction for the presence of liposomes (by fluorescence) and VLPs (by western blot against Gc). At pH 6.2, the liposomes migrated to the top of the gradient while the wild type VLPs remained in the bottom fractions (FIG. 4c and figure supplement 1a), but increasing amounts of the VLPs were observed in the top fractions at more acidic pHs. The inventors found that VLPs bearing the H953F spike mutant for pH-induced liposome coflotation was more resistant to activation, in a way that 50% activation occurred at pH 5.5 while the wt spike activation occurred already at pH 5.9 (FIG. 6). With the above techniques, those of skill in the art can routinely design other His substitutions or substitution of other protonable residues such as Asp and Glu at additional positions, and expect hantaviral spike resistance to mild acidification. Combinations of several His substitutions can lead to a still higher resistance to low pH and thus decrease perturbation of the hantaviral spikes when introduced into a pharmaceutical preparation.

The inventors have shown in this example that it is possible to design residue substitutions that confer the hantaviral spikes a higher resistance to irreversible acid-induced activation that they can face in various environments.

Example 5. Improved Thermal Stability of the Hantaviral Spikes

In order to favor conformations of the hantaviral spikes that correspond to their infectious arrangement, and in order to decrease the exposure of otherwise cryptic regions that may serve as a decoy for the immune system, the inventors subjected the diverse hantaviral spike mutants to temperature gradients in order to assess the melting temperature of each mutant.

The inventors used blue-native polyacrylamide gel electrophoresis (BN PAGE) combined with its western blotting (native western blot) to compare the stability at increasing temperatures of the detergent-solubilized hantavirus wild type and mutant spike complexes. Previous to the characterization of specific hantaviral spike mutants, the properties of the wt spike had to be established. When we thus incubated VLPs bearing wt Gn/Gc spikes at neutral pH and 20° C., the detergent-solubilized spike was identified as a single band recognized by both, anti-Gn and anti-Gc MAbs (FIG. 7A, Gc WT 20° C.). This band migrated roughly as expected in BN-PAGE, given the migration of the individual Gn and Gc monomers (see migration at 50° C.), of the Gc postfusion homotrimer (see migration at acidic pH), and of the standard reference bands. When the wild type spike complex were treated at temperatures up to 50° C., the dissociation of the Gn/Gc spikes could be visualized on the gel by the gradual disappearance of the corresponding band and the concomitant appearance of faster migrating bands, which corresponded to several oligomeric Gn forms and to a monomeric Gc species (FIG. 7A, WT 40-50° C.). Quantification of the temperature-induced dissociation of the detergent solubilized wild type ANDV Gn/Gc spike revealed a melting temperature (Tm) of 37.7±0.4° C.

By using this technique, the inventors characterized different hantaviral spike mutants, particularly those modifying the Gc/Gc homodimer contacts. Among those, we assessed the stability properties of the mutant G838C, in which we engineered a disulfide bond at the Gc dimer 2-fold axes, which thus revealed a strongly increased Tm of 48° C. (FIG. 7A, D). In this mutant spike, the Gc dissociation resulted in Gc migration species that did not dissociate at any tested condition, and the Gn/Gc complex dissociation resulted into $(Gn/Gc)_2$ heterodimers, Gn homooligomers and Gc homodimers. Thus, the higher Tm that we observed for G838C indicates that the Gc homodimer stabilizes not only the Gc homodimer interphase, instead it stabilizes the entire Gn/Gc spike. Hence, as for the wt spike, the dissociation of the Gc G838C homodimers leads to the disruption of the hantaviral spike. As a whole, our data indicates that the improvement of the Gc homodimer contacts at its 2-fold axis, strengthens the hantaviral spike structure as a whole.

Another hantaviral spike mutant that the inventors characterized includes an inter-chain disulfide bond at the position H953 located at the interphase of the Gc homodimer by introducing the substitution H953C. Although this mutant forms disulfide linked Gc dimers (FIG. 5C), the inventors found that this Gc dimer mutant completely abrogated its simultaneous interaction with Gn since not Gn/Gc migration species of higher weight could be detected Thus, from this result it can be concluded that not any inter-chain disulfide bond at the Gc homodimer interphase leads to a concomitant improvement of the overall hantaviral spike stability and underlines the importance of this assay for the spike characterization.

As negative controls, and to further include additional standards into this assay, we have also tested mutants from which we expected to weaken the Gc dimer contacts at its 2-fold axes. As expected, we could observe an opposite effect on the Gn/Gc spike stability, since the Tm decreased in all cases: Gc E677Q (Tm=35° C.), Gc D679S (Tm=34.5° C.) and Gc R951Q (Tm=32.3° C.). The decreased Tm of the mutants was accompanied by a concomitant decrease in their interactions energies, corroborating the role of the Gc homodimer in the stability of the Gn/Gc heterooligomers and confirming the role of these residues in the homodimeric Gc/Gc interactions.

The inventors also assessed hantaviral spike complexes bearing the following double residue substitutions at the Gn/Gc interface; H294C/T734C and N94C/N776C. These mutants showed high molecular weight Gn/Gc migration species that did not dissociated up to high temperatures revealing highly increased Tm's of 79.1° C. and 60.4° C., respectively (FIG. 7B and FIG. 7E).

As a whole, from this example it can be concluded that the introduction of the specific inter-chain disulfide bonds across the Gc/Gc interface located at the Gc homodimer 2-fold axes, (Gc G838) or at the Gn/Gc interface strongly increases the stability of the entire hantaviral spike. Those of skill in the art can perform similar analysis for other mutants and can expect to further improve the hantaviral spike stability by the introduction of residue modification that improve the contacts between Gn/Gc and Gn/Gn as described in Example 1. Combinations of different residue substitutions at different interphases of the hantaviral spike is likely to provide optimal spike stability.

In a still wider context, hantaviral mutants bearing multiple residue substitutions, including those that increase the dissociation energy, for example by an inter-chain disulfide bond such as G838C, H294C/T734C or N94C/N776C combined with residue substitutions that improve the hantaviral spike resistance to low pH, such as H953F, can confer optimal spike stability.

Example 6. Restriction of Molecular Fluctuations in Hantaviral Spikes

After having established how to assess and select stabilized Gc homodimers through disulfide bonds or by other residue substitutions (Examples 3-5), we also tested whether the hantaviral spike mutants induced a Gn/Gc conformation of lower flexibility concerning its molecular fluctuations. Therefore, we assessed whether the Gn/Gc heterooligomers expose transitorily the Gc fusion loops at physiological temperature (20 to 37° C., inside or outside a host cell, respectively). We further applied higher temperatures to measure whether the Gn/Gc dissociation into Gc monomers (FIG. 7) is related with the exposure of the Gc fusion loops. We measured the fusion loop exposure through their insertion into target membranes by the well-established liposome coflotation assay (Guardado-Calvo et al., 2016).

When we thus incubated the wt hantaviral spikes assembled onto VLPs at neutral pH at low temperatures (20-30° C.), we observed the VLPs in the bottom fractions of the gradient (FIG. 8A), requiring as expected at these temperatures low pH for the conformational change that leads to target membrane insertion as described previously (Acuña et al., 2015; Guardado-Calvo et al., 2016). When we further increased the temperature to 37° C. and above, VLPs floated gradually with liposomes to the upper fractions, as temperature increased. To next determine whether membrane insertion at temperatures at 37° C. and above are specifically conducted by the Gc fusion loops or rather by unspecific interactions, we tested liposome coflotation of VLPs bearing the Gc mutant W766A/F900A. This Gc mutant includes two substitutions of the aromatic residues at the tip of the cd and be fusion loops to alanine, previously proven to be required for insertion into target membranes at low pH (Guardado et al., 2016). Thus, the heating to 50° C. at neutral pH of VLPs bearing this double fusion loop mutant, showed absence of liposome insertion (FIG. 8A), thereby proofing that exclusively the fusion loops are directly involved in membrane insertion at neutral pH. When we further compared the profiles of the VLP-liposome interaction with that of (Gn/Gc)$_4$ dissociation, we found that they coincide extremely well (FIG. 8B; $T_{50\%}$interaction=37.3° C.; Tm=36.3° C.), confirming that the temperature-induced dissociation of the Gn/Gc heterooligomers into Gc monomers is responsible for the exposure of the Gc fusion loops.

After establishing the molecular fluctuations of the hantaviral spike in terms of its fusion loop exposure, we analyzed whether stabilized Gn/Gc mutants are more restricted in such fluctuations, providing additional information on the molecular structures that the antigen will adapt upon in vivo administration. By way of example, the inventors have characterized two Gc mutants to assess this. In the case of the stabilized hantaviral spike carrying the Gc G838C substitution including a disulfide bond at the Gc homodimer interphase, this mutant showed reduced fusion loop exposure at 50° C. compared to wt Gn/Gc (FIG. 8A), confirming thus a tighter association of the Gn/Gc complex.

As a control, we also analyzed the inter-chain Gc disulfide bond mutant H953C that prevents the association of the Gc homodimers into Gn/Gc heterooligomers (FIG. 7A). Consisting with the previous results showing that heat-induced liposome insertion is dependent on the dissociation of the Gn/Gc spike complex, this mutant inserts readily into liposomes at any temperature, proofing the specificity of the assay (FIG. 8A).

By using the technical approach of this example, those of skill in the art can perform similar analysis for other spike stabilizing mutants and can observe a decrease in the fluctuation of the spike.

From these results it can be concluded the hantaviral spike complex exposes a high dynamic behavior at 37° C. and above, exposing internal regions that are not functionally involved in entry and act as a decoy to elicit antibodies that are not neutralizing. The design of stabilized Gn/Gc mutants will result in an increase the Gn/Gc dissociation energy in a way that conformational dynamics will be reduced. Thereby, the increase of the spike stability has a direct impact on the antigen presentation to the immune system of a host since it increases structures that are involved in a protective immune response through neutralizing antibodies and represses structures that are involved in the generation of non-neutralizing antibodies.

Example 7. Immune Responses the Hantaviral Spikes with Improved Stability and Antigenicity In this examples the inventors provide evidence, that the stabilization of the hantaviral spikes elicits higher neutralizing antibody titers that the wt spikes.

To determine the efficacy of immune responses to wt or mutant hantaviral spikes, the inventors proceeded to assess the neutralizing antibody titers of animals which was each immunized with a different hantaviral spike mutant.

In brief, 16 week old Balb/C mice were immunized intraperitoneal with 50 µg of antigen with incomplete Freund adjuvant on day 0 and immunizations repeated on days 7 and 14 with 50 µg of antigen mixed with complete Freund Adjuvant. On day 16 blood was extracted and used to analyze the neutralizing antibody titers. The following antigens were used for immunizations: VLPs bearing wt hantaviral spikes, stabilized VLPs bearing the single mutation G838C at the Gc homodimer interface and stabilized VLPs bearing the double mutation H294C/T734C at the Gn/Gc heterodimer interface.

Neutralizing antibody titers of sera against Andes virus was assessed by incubation of Andes Orthohantavirus strain CHI-7913 with mice sera for 1 h and subsequent 1 h adsorption of the mixture to Vero E6 cells. As we established previously, using other cell entry inhibitors (Barriga et al., 2016), viral infection was allowed to proceed for 16 h to assess inhibition of the first round of infection. Next, cells were detached and the percentage of infected cells measured by cell cytometry using the anti-nucleoprotein MAb clone 7B3/F7. At a dilution of 1/500, the sera from mice immunized with VLPs bearing stabilized hantaviral spikes G838C showed 90% of viral inhibition while sera from mice immunized with wt VLPs only reduced infection by 45% (FIG. 9A). On the other hand, at a dilution of 1/500, the sera obtained from animals immunized with VLPs stabilized by double mutation H294V/T734C blocked viral infection by ~50% while in the same assay, sera from mice immunized with the wt VLPs achieved only 30% of inhibition (FIG. 9B).

These results provide evidence that stabilized hantaviral spikes induce higher neutralizaing antibody responses in animals and hence have a huge potential to be used as improved immunogens or screening for binding of other viral inhibitors.

SEQ ID NO: 1

MEGWYLVALGICYTLTLAMPKTTYELKMECPHTVGLGQGYIIGSTELGLI

SIEAASDIKLESSCNFDLHTTSMAQKSFTQVEWRKKSDTTDTTNAASTTF

EAQTKTVNLRGTCILAPELYDTLKKVKKTVLCYDLTCNQTHCQPTVYLIA

PVLTCMSIRSCMARVFTSRIQVIYEKTHCVTGQLIEGQCFNPAHTLTLSQ

PAHTYDTVTLPISCFFTPKESEQLKVIKTFEGILTKTGCTENALQGYYVC

FLGSHSEPLIVPSLEDIRSAEVVSRMLVHPRGEDHDAIQNSQSHLRIVGP

ITAKVPSTSSTDTLKGTAFAGVPMYSSLSTLVKNADPEFVFSPGIIPESN

HSVCDKKTVPITWTGYLPISGEMEKVTGCTVFCTLAGPGASCEAYSENGI

FNISSPTCLVNKVQRFRGSEQKINFICQRVDQDVVVYCNGQKKVILTKTL

VIGQCIYTFTSLFSLMPDVAHSLAVELCVPGLHGWATVMLLSTFCFGWVL

IPAVTLIILKCLRVLTFSCSHYTNESKFKFILEKVKVEYQKTMGSMVCDV

```
-continued
CHHECETAKELESHRQSCINGQCPYCMTITEATESALQAHYSICKLTGRF

QEALKKSLKKPEVKKGCYRTLGVFRYKSRCYVGLVWCLLLTCEIVIWAAS

AETPLMESGWSDTAHGVGEIPMKTDLELDFSLPSSSSYSYRRKLTNPANK

EESISFHFQMEKQVIHAEIQPLGHWMDATFNTKTAFHCYGACQKYSYPWQ

TSKCFFEKDYQYETGWGCNPGDCPGVGTGCTACGVYLDKLKSVGKAYKII

SLKYTRKVCIQLGTEQTCKHIDANDCLVTPSVKVCIVGTVSKLQPSDTLL

FLGPLEQGGVILKQWCTTSCAFGDPGDIMSTPSGMRCPEHTGSFRKICGF

ATTPVCEYQGNTISGYKRMMATKDSFQSFNLTEPHITANKLEWIDPDGNT

RDHVNLVLNRDVSFQDLSDNPCKVDLHTQAIEGAWGSGVGFTLTCTVGLT

ECPSFMTSIKACDLAMCYGSTVANLARGSNTVKVVGKGGHSGSSFKCCHD

TDCSSEGLLASAPHLERVTGFNQIDSDKVYDDGAPPCTFKCWFTKSGEWL

LGILNGNWIVVVVLVVILILSIIMFSVLCPRRGHKKTV
```

REFERENCES

Cifuentes-Muñoz N, Darlix I L, Tischler N D. Development of a lentiviral vector system to study the role of the Andes virus glycoproteins. Virus Res. 2010; 153(1):29-35. doi: 10.1016/j.virusres.2010.07.001.

Guardado-Calvo P, Bignon E A, Stettner E, Jeffers S A, Pérez-Vargas J, Pehau-Arnaudet G, Tortorici M A, Jestin J L, England P, Tischler N D, Rey F A. Mechanistic Insight into Bunyavirus-Induced Membrane Fusion from Structure-Function Analyses of the Hantavirus Envelope Glycoprotein Gc. PLoS Pathog. 2016; 12(10):e1005813. doi: 10.1371/journal.ppat.1005813. PMID: 27783711

Hardestam J, Simon M, Hedlund K O, Vaheri A, Klingström J, Lundkvist A. Ex vivo stability of the rodent-borne Hantaan virus in comparison to that of arthropod-borne members of the Bunyaviridae family. Appl Environ Microbiol. 2007; 73(8):2547-51. doi: 10.1128/AEM.02869-06. PMID: 17337567

Harrison S C. Viral membrane fusion. Virology 2015; 0:498-507. doi:10.1016/j.virol.2015.03.043.

Hepojoki J, Strandin T, Vaheri A, Lankinen H. Interactions and oligomerization of hantavirus glycoproteins. J Virol. 2010; 84(1):227-42. doi: 10.1128/JVI.00481-09.

Huiskonen J T, Hepojoki J, Laurinmaki P, Vaheri A, Lankinen H, Butcher S J, et al. Electron cryotomography of Tula hantavirus suggests a unique assembly paradigm for enveloped viruses. J Virol. 2010; 84(10):4889±97. doi: 10.1128/JVI.00057-10 PMID: 20219926

Kleinfelter L M, Jangra R K, Jae L T, Herbert A S, Mittler E, Stiles K M, Wirchnianski A S, Kielian M, Brummelkamp T R, Dye J M, Chandran K. Haploid Genetic Screen Reveals a Profound and Direct Dependence on Cholesterol for Hantavirus Membrane Fusion. MBio. 2015 Jun. 30; 6(4):e00801. doi: 10.1128/mBio.00801-15.

Li S, Rissanen I, Zeltina A, Hepojoki J, Raghwani J, Harlos K, Pybus O G, Huiskonen J T, Bowden T A. A Molecular-Level Account of the Antigenic Hantaviral Surface. Cell Rep. 2016; 16(1):278. doi: 10.1016/j.celrep.2016.06.039. PMID: 27355863

NIH, 2016: https://www.niaid.nih.gov/research/emerging-infectious-diseases-pathogens Ray N, Whidby J, Stewart S, Hooper J W, Bertolotti-Ciarlet A. Study of Andes virus entry and neutralization using a pseudovirion system. J Virol Methods 2010; 163(2):416-23. doi: 10.1016/j.jviromet.2009.11.004. Epub 2009 Nov. 10.

Rey, F A, Lok, S M. Common Features of Enveloped Viruses and Implications for Immunogen Design for Next-Generation Vaccines. Cell 2018; 172 (6), 1319-1334.

Boudreau E F, Josleyn M, Ullman D, Fisher D, Dalrymple L, Sellers-Myers K, Loudon P, Rusnak J, Rivard R, Schmaljohn C, Hooper J W. A Phase 1 clinical trial of Hantaan virus and Puumala virus M-segment DNA vaccines for hemorrhagic fever with renal syndrome. Vaccine 2012; 30(11):1951-8. doi: 10.1016/j.vaccine.2012.01.024.

Barriga G P, Villalón-Letelier F, Márquez CL, Bignon E A, Acuña R, Ross B H, Monasterio O, Mardones G A, Vidal S E, Tischler N D. Inhibition of the Hantavirus Fusion Process by Predicted Domain III and Stem Peptides from Glycoprotein Gc. PLoS Negl Trop Dis. 2016; 10(7): e0004799. doi: 10.1371/journal.pntd.0004799.

Vial P A, Valdivieso F, Calvo M, Rioseco M L, Riquelme R, Araneda A, Tomicic V, Graf J, Paredes L, Florenzano M, Bidart T, Cuiza A, Marco C, Hjelle B, Ye C, Hanfelt-Goade D, Vial C, Rivera J C, Delgado I, Mertz G J; Hantavirus Study Group in Chile. A non-randomized multicentre trial of human immune plasma for treatment of hantavirus cardiopulmonary syndrome caused by Andes virus. Antivir Ther. 2015; 20(4):377-86. doi: 10.3851/IMP2875.

Maes P, Clement J, Van Ranst M. Recent approaches in hantavirus vaccine development. Expert Rev Vaccines 2009; 8(1):67-76. doi: 10.1586/14760584.8.1.67.

The invention claimed is:

1. A stabilized hantaviral spike comprising at least one homodimer of Gc mutants, the at least one homodimer of Gc mutants comprising first and second polypeptide chains, each of the first and second polypeptide chains having an amino acid sequence that comprises the amino acid sequence of the Gc of SEQ ID NO: 1 at positions 652-1138 but with at least one amino acid substitution at a position determined when each of the first and second polypeptide chains is aligned with the Gc of SEQ ID NO: 1, wherein the at least one amino acid substitution in each of the first and second polypeptide chains is selected from the group consisting of: the substitution G838C that results in the Gc mutant sequence of SEQ ID NO: 2, the substitution T839C that results in the Gc mutant sequence of SEQ ID NO: 3, the substitution H953C that results in the Gc mutant sequence of SEQ ID NO: 4, and the substitution H953F that results in the Gc mutant sequence of SEQ ID NO: 5.

2. The stabilized hantaviral spike according to claim 1, wherein each polypeptide chain of the at least one homodimer of Gc mutants has the substitution G838C, wherein the amino acid residues 838C of the respective polypeptide chains are linked together through a disulphide inter-chain bond.

3. The stabilized hantaviral spike according to claim 1, wherein each polypeptide chain of the at least one homodimer of Gc mutants has the substitution T839C, wherein the amino acid residues 839C of the respective polypeptide chains are linked together through a disulphide inter-chain bond.

4. The stabilized hantaviral spike according to claim 1, wherein each polypeptide chain of the at least one homodimer of Gc mutants has the substitution H953C, wherein the amino acid residues 953C of the respective polypeptide chains are linked together through a disulphide inter-chain bond.

5. The stabilized hantaviral spike according to claim 1, wherein each polypeptide chain of the at least one homodimer of Gc mutants has the substitution H953F.

6. The stabilized hantaviral spike according to claim 1, wherein each polypeptide chain of the at least one homodimer of Gc mutants has a double substitution Q844C/H953C, wherein the amino acid residues 844C and 953C are linked respectively to the amino acid residues 844C and 953C through a disulphide inter-chain bond.

7. A stabilized hantaviral spike comprising at least one heterodimer of Gn/Gc mutants comprising a mutant Gn monomer and a mutant Gc monomer, wherein the mutant Gn monomer comprises the amino acid sequence of the Gn of SEQ ID NO: 1 at positions 1-651 but with at least one amino acid mutation (substitution) selected from the group consisting of: H294C, R281C, T99C, K85C, N94C and a combination thereof; and wherein the mutant Gc monomer comprises at least one amino acid mutation (substitution) selected from the group consisting of: T734C, P748C, P774C, V776C and a combination thereof, the positions of the substitutions being determined by alignment with SEQ ID NO: 1.

8. The stabilized hantaviral spike according to claim 7, which comprises the at least one heterodimer with the mutant Gn monomer having the substitution H294C and the mutant Gc monomer having the substitution T734C, wherein the amino acid residues 294C and 734C of the respective mutant Gn monomer and mutant Gc monomer are linked together through a disulphide inter-chain bond.

9. The stabilized hantaviral spike according to claim 7, which comprises the at least one heterodimer with the mutant Gn monomer having the substitution R281C and the mutant Gc monomer having the substitution P748C, wherein the residues 281C and 748C are linked together through a disulphide inter-chain bond.

10. The stabilized hantaviral spike according to claim 7, which comprises the at least one heterodimer with the mutant Gn monomer having the substitution T99C and the mutant Gc monomer having the substitution P774C, wherein the residues 99C and 774C are linked together through a disulphide inter-chain bond.

11. The stabilized hantaviral spike according to claim 7, which comprises the at least one heterodimer with the mutant Gn monomer having the substitution K85C and the mutant Gc monomer having the substitution P774C, wherein the residues 85C and 774C are linked together through a disulphide inter-chain bond.

12. The stabilized hantaviral spike according to claim 7, which comprises the at least one heterodimer with the mutant Gn monomer having the substitution N94C and the mutant Gc monomer having the substitution V776C, wherein the residues 85C and 774C are linked together through a disulphide inter-chain bond.

13. A stabilized hantaviral spike, which comprises at least one homooligomer comprising a first Gn mutant subunit and a second Gn mutant subunit, each of the first and second Gn mutant subunits having a double substitution E61C/Q200C, wherein positions of the substitutions are determined by alignment with SEQ ID NO: 1, wherein the amino acid residues 61C and 200C of the first Gn mutant subunit are linked respectively to the amino acid residues 61C and 200C of the second Gn mutant subunit through disulphide inter-chain bonds between the first and second Gn mutant subunits.

14. A kit comprising the stabilized hantaviral spike according to claim 1 and a vector selected from the group consisting of an envelope of a recombinant virus, a pseudotype virus vector, and a virus-like particle.

\* \* \* \* \*

SEQUENCE LISTING

```
<160> NUMBER OF SEQ ID NOS: 19

<210> SEQ ID NO 1
<211> LENGTH: 1138
<212> TYPE: PRT
<213> ORGANISM: Andes orthohantavirus
<220> FEATURE:
<221> NAME/KEY: misc_feature
<222> LOCATION: (1)..(1138)
<223> OTHER INFORMATION: ANDV GPC WT

<400> SEQUENCE: 1

Met Glu Gly Trp Tyr Leu Val Ala Leu Gly Ile Cys Tyr Thr Leu Thr
1               5                   10                  15
```

-continued

```
Leu Ala Met Pro Lys Thr Thr Tyr Glu Leu Lys Met Glu Cys Pro His
             20                  25                  30

Thr Val Gly Leu Gly Gln Gly Tyr Ile Ile Gly Ser Thr Glu Leu Gly
         35                  40                  45

Leu Ile Ser Ile Glu Ala Ala Ser Asp Ile Lys Leu Glu Ser Ser Cys
     50                  55                  60

Asn Phe Asp Leu His Thr Thr Ser Met Ala Gln Lys Ser Phe Thr Gln
65                  70                  75                  80

Val Glu Trp Arg Lys Lys Ser Asp Thr Thr Asp Thr Thr Asn Ala Ala
             85                  90                  95

Ser Thr Thr Phe Glu Ala Gln Thr Lys Thr Val Asn Leu Arg Gly Thr
         100                 105                 110

Cys Ile Leu Ala Pro Glu Leu Tyr Asp Thr Leu Lys Lys Val Lys Lys
     115                 120                 125

Thr Val Leu Cys Tyr Asp Leu Thr Cys Asn Gln Thr His Cys Gln Pro
    130                 135                 140

Thr Val Tyr Leu Ile Ala Pro Val Leu Thr Cys Met Ser Ile Arg Ser
145                 150                 155                 160

Cys Met Ala Arg Val Phe Thr Ser Arg Ile Gln Val Ile Tyr Glu Lys
             165                 170                 175

Thr His Cys Val Thr Gly Gln Leu Ile Glu Gly Gln Cys Phe Asn Pro
         180                 185                 190

Ala His Thr Leu Thr Leu Ser Gln Pro Ala His Thr Tyr Asp Thr Val
     195                 200                 205

Thr Leu Pro Ile Ser Cys Phe Phe Thr Pro Lys Glu Ser Glu Gln Leu
    210                 215                 220

Lys Val Ile Lys Thr Phe Glu Gly Ile Leu Thr Lys Thr Gly Cys Thr
225                 230                 235                 240

Glu Asn Ala Leu Gln Gly Tyr Tyr Val Cys Phe Leu Gly Ser His Ser
             245                 250                 255

Glu Pro Leu Ile Val Pro Ser Leu Glu Asp Ile Arg Ser Ala Glu Val
         260                 265                 270

Val Ser Arg Met Leu Val His Pro Arg Gly Glu Asp His Asp Ala Ile
     275                 280                 285

Gln Asn Ser Gln Ser His Leu Arg Ile Val Gly Pro Ile Thr Ala Lys
    290                 295                 300

Val Pro Ser Thr Ser Ser Thr Asp Thr Leu Lys Gly Thr Ala Phe Ala
305                 310                 315                 320

Gly Val Pro Met Tyr Ser Ser Leu Ser Thr Leu Val Lys Asn Ala Asp
             325                 330                 335

Pro Glu Phe Val Phe Ser Pro Gly Ile Ile Pro Glu Ser Asn His Ser
         340                 345                 350

Val Cys Asp Lys Lys Thr Val Pro Ile Thr Trp Thr Gly Tyr Leu Pro
     355                 360                 365

Ile Ser Gly Glu Met Glu Lys Val Thr Gly Cys Thr Val Phe Cys Thr
    370                 375                 380

Leu Ala Gly Pro Gly Ala Ser Cys Glu Ala Tyr Ser Glu Asn Gly Ile
385                 390                 395                 400

Phe Asn Ile Ser Ser Pro Thr Cys Leu Val Asn Lys Val Gln Arg Phe
             405                 410                 415

Arg Gly Ser Glu Gln Lys Ile Asn Phe Ile Cys Gln Arg Val Asp Gln
         420                 425                 430

Asp Val Val Val Tyr Cys Asn Gly Gln Lys Lys Val Ile Leu Thr Lys
```

```
                435                 440                 445
Thr Leu Val Ile Gly Gln Cys Ile Tyr Thr Phe Thr Ser Leu Phe Ser
450                 455                 460

Leu Met Pro Asp Val Ala His Ser Leu Ala Val Glu Leu Cys Val Pro
465                 470                 475                 480

Gly Leu His Gly Trp Ala Thr Val Met Leu Leu Ser Thr Phe Cys Phe
                485                 490                 495

Gly Trp Val Leu Ile Pro Ala Val Thr Leu Ile Ile Leu Lys Cys Leu
                500                 505                 510

Arg Val Leu Thr Phe Ser Cys Ser His Tyr Thr Asn Glu Ser Lys Phe
                515                 520                 525

Lys Phe Ile Leu Glu Lys Val Lys Val Glu Tyr Gln Lys Thr Met Gly
                530                 535                 540

Ser Met Val Cys Asp Val Cys His His Glu Cys Glu Thr Ala Lys Glu
545                 550                 555                 560

Leu Glu Ser His Arg Gln Ser Cys Ile Asn Gly Gln Cys Pro Tyr Cys
                565                 570                 575

Met Thr Ile Thr Glu Ala Thr Glu Ser Ala Leu Gln Ala His Tyr Ser
                580                 585                 590

Ile Cys Lys Leu Thr Gly Arg Phe Gln Glu Ala Leu Lys Lys Ser Leu
                595                 600                 605

Lys Lys Pro Glu Val Lys Lys Gly Cys Tyr Arg Thr Leu Gly Val Phe
610                 615                 620

Arg Tyr Lys Ser Arg Cys Tyr Val Gly Leu Val Trp Cys Leu Leu Leu
625                 630                 635                 640

Thr Cys Glu Ile Val Ile Trp Ala Ala Ser Ala Glu Thr Pro Leu Met
                645                 650                 655

Glu Ser Gly Trp Ser Asp Thr Ala His Gly Val Gly Glu Ile Pro Met
                660                 665                 670

Lys Thr Asp Leu Glu Leu Asp Phe Ser Leu Pro Ser Ser Ser Ser Tyr
                675                 680                 685

Ser Tyr Arg Arg Lys Leu Thr Asn Pro Ala Asn Lys Glu Glu Ser Ile
                690                 695                 700

Ser Phe His Phe Gln Met Glu Lys Gln Val Ile His Ala Glu Ile Gln
705                 710                 715                 720

Pro Leu Gly His Trp Met Asp Ala Thr Phe Asn Thr Lys Thr Ala Phe
                725                 730                 735

His Cys Tyr Gly Ala Cys Gln Lys Tyr Ser Tyr Pro Trp Gln Thr Ser
                740                 745                 750

Lys Cys Phe Phe Glu Lys Asp Tyr Gln Tyr Glu Thr Gly Trp Gly Cys
                755                 760                 765

Asn Pro Gly Asp Cys Pro Gly Val Gly Thr Gly Cys Thr Ala Cys Gly
                770                 775                 780

Val Tyr Leu Asp Lys Leu Lys Ser Val Gly Lys Ala Tyr Lys Ile Ile
785                 790                 795                 800

Ser Leu Lys Tyr Thr Arg Lys Val Cys Ile Gln Leu Gly Thr Glu Gln
                805                 810                 815

Thr Cys Lys His Ile Asp Ala Asn Asp Cys Leu Val Thr Pro Ser Val
                820                 825                 830

Lys Val Cys Ile Val Gly Thr Val Ser Lys Leu Gln Pro Ser Asp Thr
                835                 840                 845

Leu Leu Phe Leu Gly Pro Leu Glu Gln Gly Gly Val Ile Leu Lys Gln
850                 855                 860
```

```
Trp Cys Thr Thr Ser Cys Ala Phe Gly Asp Pro Gly Asp Ile Met Ser
865                 870                 875                 880

Thr Pro Ser Gly Met Arg Cys Pro Glu His Thr Gly Ser Phe Arg Lys
            885                 890                 895

Ile Cys Gly Phe Ala Thr Thr Pro Val Cys Glu Tyr Gln Gly Asn Thr
        900                 905                 910

Ile Ser Gly Tyr Lys Arg Met Met Ala Thr Lys Asp Ser Phe Gln Ser
            915                 920                 925

Phe Asn Leu Thr Glu Pro His Ile Thr Ala Asn Lys Leu Glu Trp Ile
930                 935                 940

Asp Pro Asp Gly Asn Thr Arg Asp His Val Asn Leu Val Leu Asn Arg
945                 950                 955                 960

Asp Val Ser Phe Gln Asp Leu Ser Asp Asn Pro Cys Lys Val Asp Leu
            965                 970                 975

His Thr Gln Ala Ile Glu Gly Ala Trp Gly Ser Gly Val Gly Phe Thr
        980                 985                 990

Leu Thr Cys Thr Val Gly Leu Thr Glu Cys Pro Ser Phe Met Thr Ser
            995             1000                1005

Ile Lys Ala Cys Asp Leu Ala Met Cys Tyr Gly Ser Thr Val Ala
    1010                1015                1020

Asn Leu Ala Arg Gly Ser Asn Thr Val Lys Val Val Gly Lys Gly
    1025                1030                1035

Gly His Ser Gly Ser Ser Phe Lys Cys Cys His Asp Thr Asp Cys
    1040                1045                1050

Ser Ser Glu Gly Leu Leu Ala Ser Ala Pro His Leu Glu Arg Val
    1055                1060                1065

Thr Gly Phe Asn Gln Ile Asp Ser Asp Lys Val Tyr Asp Asp Gly
    1070                1075                1080

Ala Pro Pro Cys Thr Phe Lys Cys Trp Phe Thr Lys Ser Gly Glu
    1085                1090                1095

Trp Leu Leu Gly Ile Leu Asn Gly Asn Trp Ile Val Val Val Val
    1100                1105                1110

Leu Val Val Ile Leu Ile Leu Ser Ile Ile Met Phe Ser Val Leu
    1115                1120                1125

Cys Pro Arg Arg Gly His Lys Lys Thr Val
    1130                1135

<210> SEQ ID NO 2
<211> LENGTH: 1138
<212> TYPE: PRT
<213> ORGANISM: Artificial Sequence
<220> FEATURE:
<223> OTHER INFORMATION: Synthetic: ANDV GPC G838C

<400> SEQUENCE: 2

Met Glu Gly Trp Tyr Leu Val Ala Leu Gly Ile Cys Tyr Thr Leu Thr
1               5                   10                  15

Leu Ala Met Pro Lys Thr Thr Tyr Glu Leu Lys Met Glu Cys Pro His
            20                  25                  30

Thr Val Gly Leu Gly Gln Gly Tyr Ile Ile Gly Ser Thr Glu Leu Gly
        35                  40                  45

Leu Ile Ser Ile Glu Ala Ala Ser Asp Ile Lys Leu Glu Ser Ser Cys
    50                  55                  60

Asn Phe Asp Leu His Thr Thr Ser Met Ala Gln Lys Ser Phe Thr Gln
65                  70                  75                  80
```

-continued

Val Glu Trp Arg Lys Lys Ser Asp Thr Thr Asp Thr Asn Ala Ala
                    85                  90                  95

Ser Thr Thr Phe Glu Ala Gln Thr Lys Thr Val Asn Leu Arg Gly Thr
                100                 105                 110

Cys Ile Leu Ala Pro Glu Leu Tyr Asp Thr Leu Lys Lys Val Lys Lys
            115                 120                 125

Thr Val Leu Cys Tyr Asp Leu Thr Cys Asn Gln Thr His Cys Gln Pro
    130                 135                 140

Thr Val Tyr Leu Ile Ala Pro Val Leu Thr Cys Met Ser Ile Arg Ser
145                 150                 155                 160

Cys Met Ala Arg Val Phe Thr Ser Arg Ile Gln Val Ile Tyr Glu Lys
                165                 170                 175

Thr His Cys Val Thr Gly Gln Leu Ile Glu Gly Gln Cys Phe Asn Pro
                180                 185                 190

Ala His Thr Leu Thr Leu Ser Gln Pro Ala His Thr Tyr Asp Thr Val
            195                 200                 205

Thr Leu Pro Ile Ser Cys Phe Phe Thr Pro Lys Glu Ser Glu Gln Leu
    210                 215                 220

Lys Val Ile Lys Thr Phe Glu Gly Ile Leu Thr Lys Thr Gly Cys Thr
225                 230                 235                 240

Glu Asn Ala Leu Gln Gly Tyr Tyr Val Cys Phe Leu Gly Ser His Ser
                245                 250                 255

Glu Pro Leu Ile Val Pro Ser Leu Glu Asp Ile Arg Ser Ala Glu Val
                260                 265                 270

Val Ser Arg Met Leu Val His Pro Arg Gly Glu Asp His Asp Ala Ile
                275                 280                 285

Gln Asn Ser Gln Ser His Leu Arg Ile Val Gly Pro Ile Thr Ala Lys
            290                 295                 300

Val Pro Ser Thr Ser Ser Thr Asp Thr Leu Lys Gly Thr Ala Phe Ala
305                 310                 315                 320

Gly Val Pro Met Tyr Ser Ser Leu Ser Thr Leu Val Lys Asn Ala Asp
                325                 330                 335

Pro Glu Phe Val Phe Ser Pro Gly Ile Ile Pro Glu Ser Asn His Ser
                340                 345                 350

Val Cys Asp Lys Lys Thr Val Pro Ile Thr Trp Thr Gly Tyr Leu Pro
            355                 360                 365

Ile Ser Gly Glu Met Glu Lys Val Thr Gly Cys Thr Val Phe Cys Thr
    370                 375                 380

Leu Ala Gly Pro Gly Ala Ser Cys Glu Ala Tyr Ser Glu Asn Gly Ile
385                 390                 395                 400

Phe Asn Ile Ser Ser Pro Thr Cys Leu Val Asn Lys Val Gln Arg Phe
                405                 410                 415

Arg Gly Ser Glu Gln Lys Ile Asn Phe Ile Cys Gln Arg Val Asp Gln
                420                 425                 430

Asp Val Val Tyr Cys Asn Gly Gln Lys Lys Val Ile Leu Thr Lys
            435                 440                 445

Thr Leu Val Ile Gly Gln Cys Ile Tyr Thr Phe Thr Ser Leu Phe Ser
    450                 455                 460

Leu Met Pro Asp Val Ala His Ser Leu Ala Val Glu Leu Cys Val Pro
465                 470                 475                 480

Gly Leu His Gly Trp Ala Thr Val Met Leu Leu Ser Thr Phe Cys Phe
                485                 490                 495

```
Gly Trp Val Leu Ile Pro Ala Val Thr Leu Ile Ile Leu Lys Cys Leu
            500             505             510

Arg Val Leu Thr Phe Ser Cys Ser His Tyr Thr Asn Glu Ser Lys Phe
            515             520             525

Lys Phe Ile Leu Glu Lys Val Lys Val Glu Tyr Gln Lys Thr Met Gly
            530             535             540

Ser Met Val Cys Asp Val Cys His His Glu Cys Glu Thr Ala Lys Glu
545             550             555             560

Leu Glu Ser His Arg Gln Ser Cys Ile Asn Gly Gln Cys Pro Tyr Cys
            565             570             575

Met Thr Ile Thr Glu Ala Thr Glu Ser Ala Leu Gln Ala His Tyr Ser
            580             585             590

Ile Cys Lys Leu Thr Gly Arg Phe Gln Glu Ala Leu Lys Lys Ser Leu
            595             600             605

Lys Lys Pro Glu Val Lys Lys Gly Cys Tyr Arg Thr Leu Gly Val Phe
            610             615             620

Arg Tyr Lys Ser Arg Cys Tyr Val Gly Leu Val Trp Cys Leu Leu Leu
625             630             635             640

Thr Cys Glu Ile Val Ile Trp Ala Ala Ser Ala Glu Thr Pro Leu Met
            645             650             655

Glu Ser Gly Trp Ser Asp Thr Ala His Gly Val Gly Glu Ile Pro Met
            660             665             670

Lys Thr Asp Leu Glu Leu Asp Phe Ser Leu Pro Ser Ser Ser Ser Tyr
            675             680             685

Ser Tyr Arg Arg Lys Leu Thr Asn Pro Ala Asn Lys Glu Glu Ser Ile
            690             695             700

Ser Phe His Phe Gln Met Glu Lys Gln Val Ile His Ala Glu Ile Gln
705             710             715             720

Pro Leu Gly His Trp Met Asp Ala Thr Phe Asn Thr Lys Thr Ala Phe
            725             730             735

His Cys Tyr Gly Ala Cys Gln Lys Tyr Ser Tyr Pro Trp Gln Thr Ser
            740             745             750

Lys Cys Phe Phe Glu Lys Asp Tyr Gln Tyr Glu Thr Gly Trp Gly Cys
            755             760             765

Asn Pro Gly Asp Cys Pro Gly Val Gly Thr Gly Cys Thr Ala Cys Gly
            770             775             780

Val Tyr Leu Asp Lys Leu Lys Ser Val Gly Lys Ala Tyr Lys Ile Ile
785             790             795             800

Ser Leu Lys Tyr Thr Arg Lys Val Cys Ile Gln Leu Gly Thr Glu Gln
            805             810             815

Thr Cys Lys His Ile Asp Ala Asn Asp Cys Leu Val Thr Pro Ser Val
            820             825             830

Lys Val Cys Ile Val Cys Thr Val Ser Lys Leu Gln Pro Ser Asp Thr
            835             840             845

Leu Leu Phe Leu Gly Pro Leu Glu Gln Gly Gly Val Ile Leu Lys Gln
            850             855             860

Trp Cys Thr Thr Ser Cys Ala Phe Gly Asp Pro Gly Asp Ile Met Ser
865             870             875             880

Thr Pro Ser Gly Met Arg Cys Pro Glu His Thr Gly Ser Phe Arg Lys
            885             890             895

Ile Cys Gly Phe Ala Thr Thr Pro Val Cys Glu Tyr Gln Gly Asn Thr
            900             905             910

Ile Ser Gly Tyr Lys Arg Met Met Ala Thr Lys Asp Ser Phe Gln Ser
```

```
                915                 920                 925
Phe Asn Leu Thr Glu Pro His Ile Thr Ala Asn Lys Leu Glu Trp Ile
            930                 935                 940
Asp Pro Asp Gly Asn Thr Arg Asp His Val Asn Leu Val Leu Asn Arg
945                 950                 955                 960
Asp Val Ser Phe Gln Asp Leu Ser Asp Asn Pro Cys Lys Val Asp Leu
                965                 970                 975
His Thr Gln Ala Ile Glu Gly Ala Trp Gly Ser Gly Val Gly Phe Thr
            980                 985                 990
Leu Thr Cys Thr Val Gly Leu Thr Glu Cys Pro Ser Phe Met Thr Ser
                995                 1000                1005
Ile Lys Ala Cys Asp Leu Ala Met Cys Tyr Gly Ser Thr Val Ala
        1010                1015                1020
Asn Leu Ala Arg Gly Ser Asn Thr Val Lys Val Val Gly Lys Gly
        1025                1030                1035
Gly His Ser Gly Ser Ser Phe Lys Cys Cys His Asp Thr Asp Cys
        1040                1045                1050
Ser Ser Glu Gly Leu Leu Ala Ser Ala Pro His Leu Glu Arg Val
        1055                1060                1065
Thr Gly Phe Asn Gln Ile Asp Ser Asp Lys Val Tyr Asp Asp Gly
        1070                1075                1080
Ala Pro Pro Cys Thr Phe Lys Cys Trp Phe Thr Lys Ser Gly Glu
        1085                1090                1095
Trp Leu Leu Gly Ile Leu Asn Gly Asn Trp Ile Val Val Val Val
        1100                1105                1110
Leu Val Val Ile Leu Ile Leu Ser Ile Ile Met Phe Ser Val Leu
        1115                1120                1125
Cys Pro Arg Arg Gly His Lys Lys Thr Val
        1130                1135
```

<210> SEQ ID NO 3
<211> LENGTH: 1138
<212> TYPE: PRT
<213> ORGANISM: Artificial Sequence
<220> FEATURE:
<223> OTHER INFORMATION: Synthetic: ANDV GPC T839C

<400> SEQUENCE: 3

```
Met Glu Gly Trp Tyr Leu Val Ala Leu Gly Ile Cys Tyr Thr Leu Thr
1               5                   10                  15
Leu Ala Met Pro Lys Thr Thr Tyr Glu Leu Lys Met Glu Cys Pro His
            20                  25                  30
Thr Val Gly Leu Gly Gln Gly Tyr Ile Ile Gly Ser Thr Glu Leu Gly
        35                  40                  45
Leu Ile Ser Ile Glu Ala Ala Ser Asp Ile Lys Leu Glu Ser Ser Cys
    50                  55                  60
Asn Phe Asp Leu His Thr Thr Ser Met Ala Gln Lys Ser Phe Thr Gln
65                  70                  75                  80
Val Glu Trp Arg Lys Lys Ser Asp Thr Thr Asp Thr Asn Ala Ala
                85                  90                  95
Ser Thr Thr Phe Glu Ala Gln Thr Lys Thr Val Asn Leu Arg Gly Thr
            100                 105                 110
Cys Ile Leu Ala Pro Glu Leu Tyr Asp Thr Leu Lys Lys Val Lys Lys
        115                 120                 125
Thr Val Leu Cys Tyr Asp Leu Thr Cys Asn Gln Thr His Cys Gln Pro
```

-continued

```
                130                 135                 140
Thr Val Tyr Leu Ile Ala Pro Val Leu Thr Cys Met Ser Ile Arg Ser
145                 150                 155                 160

Cys Met Ala Arg Val Phe Thr Ser Arg Ile Gln Val Ile Tyr Glu Lys
                165                 170                 175

Thr His Cys Val Thr Gly Gln Leu Ile Glu Gly Gln Cys Phe Asn Pro
                180                 185                 190

Ala His Thr Leu Thr Leu Ser Gln Pro Ala His Thr Tyr Asp Thr Val
                195                 200                 205

Thr Leu Pro Ile Ser Cys Phe Phe Thr Pro Lys Glu Ser Glu Gln Leu
210                 215                 220

Lys Val Ile Lys Thr Phe Glu Gly Ile Leu Thr Lys Thr Gly Cys Thr
225                 230                 235                 240

Glu Asn Ala Leu Gln Gly Tyr Tyr Val Cys Phe Leu Gly Ser His Ser
                245                 250                 255

Glu Pro Leu Ile Val Pro Ser Leu Glu Asp Ile Arg Ser Ala Glu Val
                260                 265                 270

Val Ser Arg Met Leu Val His Pro Arg Gly Glu Asp His Asp Ala Ile
                275                 280                 285

Gln Asn Ser Gln Ser His Leu Arg Ile Val Gly Pro Ile Thr Ala Lys
290                 295                 300

Val Pro Ser Thr Ser Ser Thr Asp Thr Leu Lys Gly Thr Ala Phe Ala
305                 310                 315                 320

Gly Val Pro Met Tyr Ser Ser Leu Ser Thr Leu Val Lys Asn Ala Asp
                325                 330                 335

Pro Glu Phe Val Phe Ser Pro Gly Ile Ile Pro Glu Ser Asn His Ser
                340                 345                 350

Val Cys Asp Lys Lys Thr Val Pro Ile Thr Trp Thr Gly Tyr Leu Pro
                355                 360                 365

Ile Ser Gly Glu Met Glu Lys Val Thr Gly Cys Thr Val Phe Cys Thr
370                 375                 380

Leu Ala Gly Pro Gly Ala Ser Cys Glu Ala Tyr Ser Glu Asn Gly Ile
385                 390                 395                 400

Phe Asn Ile Ser Ser Pro Thr Cys Leu Val Asn Lys Val Gln Arg Phe
                405                 410                 415

Arg Gly Ser Glu Gln Lys Ile Asn Phe Ile Cys Gln Arg Val Asp Gln
                420                 425                 430

Asp Val Val Val Tyr Cys Asn Gly Gln Lys Lys Val Ile Leu Thr Lys
                435                 440                 445

Thr Leu Val Ile Gly Gln Cys Ile Tyr Thr Phe Thr Ser Leu Phe Ser
450                 455                 460

Leu Met Pro Asp Val Ala His Ser Leu Ala Val Glu Leu Cys Val Pro
465                 470                 475                 480

Gly Leu His Gly Trp Ala Thr Val Met Leu Leu Ser Thr Phe Cys Phe
                485                 490                 495

Gly Trp Val Leu Ile Pro Ala Val Thr Leu Ile Ile Leu Lys Cys Leu
                500                 505                 510

Arg Val Leu Thr Phe Ser Cys Ser His Tyr Thr Asn Glu Ser Lys Phe
                515                 520                 525

Lys Phe Ile Leu Glu Lys Val Lys Val Glu Tyr Gln Lys Thr Met Gly
                530                 535                 540

Ser Met Val Cys Asp Val Cys His His Glu Cys Glu Thr Ala Lys Glu
545                 550                 555                 560
```

```
Leu Glu Ser His Arg Gln Ser Cys Ile Asn Gly Gln Cys Pro Tyr Cys
                565                 570                 575

Met Thr Ile Thr Glu Ala Thr Glu Ser Ala Leu Gln Ala His Tyr Ser
            580                 585                 590

Ile Cys Lys Leu Thr Gly Arg Phe Gln Glu Ala Leu Lys Lys Ser Leu
        595                 600                 605

Lys Lys Pro Glu Val Lys Lys Gly Cys Tyr Arg Thr Leu Gly Val Phe
    610                 615                 620

Arg Tyr Lys Ser Arg Cys Tyr Val Gly Leu Val Trp Cys Leu Leu Leu
625                 630                 635                 640

Thr Cys Glu Ile Val Ile Trp Ala Ala Ser Ala Glu Thr Pro Leu Met
                645                 650                 655

Glu Ser Gly Trp Ser Asp Thr Ala His Gly Val Gly Glu Ile Pro Met
            660                 665                 670

Lys Thr Asp Leu Glu Leu Asp Phe Ser Leu Pro Ser Ser Ser Ser Tyr
        675                 680                 685

Ser Tyr Arg Arg Lys Leu Thr Asn Pro Ala Asn Lys Glu Glu Ser Ile
    690                 695                 700

Ser Phe His Phe Gln Met Glu Lys Gln Val Ile His Ala Glu Ile Gln
705                 710                 715                 720

Pro Leu Gly His Trp Met Asp Ala Thr Phe Asn Thr Lys Thr Ala Phe
                725                 730                 735

His Cys Tyr Gly Ala Cys Gln Lys Tyr Ser Tyr Pro Trp Gln Thr Ser
            740                 745                 750

Lys Cys Phe Phe Glu Lys Asp Tyr Gln Tyr Glu Thr Gly Trp Gly Cys
        755                 760                 765

Asn Pro Gly Asp Cys Pro Gly Val Gly Thr Gly Cys Thr Ala Cys Gly
    770                 775                 780

Val Tyr Leu Asp Lys Leu Lys Ser Val Gly Lys Ala Tyr Lys Ile Ile
785                 790                 795                 800

Ser Leu Lys Tyr Thr Arg Lys Val Cys Ile Gln Leu Gly Thr Glu Gln
                805                 810                 815

Thr Cys Lys His Ile Asp Ala Asn Asp Cys Leu Val Thr Pro Ser Val
            820                 825                 830

Lys Val Cys Ile Val Gly Cys Val Ser Lys Leu Gln Pro Ser Asp Thr
        835                 840                 845

Leu Leu Phe Leu Gly Pro Leu Glu Gln Gly Gly Val Ile Leu Lys Gln
    850                 855                 860

Trp Cys Thr Thr Ser Cys Ala Phe Gly Asp Pro Gly Asp Ile Met Ser
865                 870                 875                 880

Thr Pro Ser Gly Met Arg Cys Pro Glu His Thr Gly Ser Phe Arg Lys
                885                 890                 895

Ile Cys Gly Phe Ala Thr Thr Pro Val Cys Glu Tyr Gln Gly Asn Thr
            900                 905                 910

Ile Ser Gly Tyr Lys Arg Met Met Ala Thr Lys Asp Ser Phe Gln Ser
        915                 920                 925

Phe Asn Leu Thr Glu Pro His Ile Thr Ala Asn Lys Leu Glu Trp Ile
    930                 935                 940

Asp Pro Asp Gly Asn Thr Arg Asp His Val Asn Leu Val Leu Asn Arg
945                 950                 955                 960

Asp Val Ser Phe Gln Asp Leu Ser Asp Asn Pro Cys Lys Val Asp Leu
                965                 970                 975
```

```
His Thr Gln Ala Ile Glu Gly Ala Trp Gly Ser Gly Val Gly Phe Thr
            980                 985                 990

Leu Thr Cys Thr Val Gly Leu Thr  Glu Cys Pro Ser Phe Met Thr Ser
        995                 1000                1005

Ile Lys  Ala Cys Asp Leu Ala  Met Cys Tyr Gly Ser  Thr Val Ala
    1010                 1015                 1020

Asn Leu Ala Arg Gly Ser Asn  Thr Val Lys Val Val  Gly Lys Gly
        1025                 1030                 1035

Gly His  Ser Gly Ser Ser Phe  Lys Cys Cys His Asp  Thr Asp Cys
        1040                 1045                 1050

Ser Ser Glu Gly Leu Leu Ala  Ser Ala Pro His Leu  Glu Arg Val
        1055                 1060                 1065

Thr Gly  Phe Asn Gln Ile Asp  Ser Asp Lys Val Tyr  Asp Asp Gly
        1070                 1075                 1080

Ala Pro Pro Cys Thr Phe Lys  Cys Trp Phe Thr Lys  Ser Gly Glu
        1085                 1090                 1095

Trp Leu Leu Gly Ile Leu Asn  Gly Asn Trp Ile Val  Val Val Val
        1100                 1105                 1110

Leu Val  Val Ile Leu Ile Leu  Ser Ile Ile Met Phe  Ser Val Leu
        1115                 1120                 1125

Cys Pro Arg Arg Gly His Lys  Lys Thr Val
        1130                 1135

<210> SEQ ID NO 4
<211> LENGTH: 1138
<212> TYPE: PRT
<213> ORGANISM: Artificial Sequence
<220> FEATURE:
<223> OTHER INFORMATION: Synthetic: ANDV GPC H953C

<400> SEQUENCE: 4

Met Glu Gly Trp Tyr Leu Val Ala Leu Gly Ile Cys Tyr Thr Leu Thr
1               5                   10                  15

Leu Ala Met Pro Lys Thr Thr Tyr Glu Leu Lys Met Glu Cys Pro His
            20                  25                  30

Thr Val Gly Leu Gly Gln Gly Tyr Ile Ile Gly Ser Thr Glu Leu Gly
        35                  40                  45

Leu Ile Ser Ile Glu Ala Ala Ser Asp Ile Lys Leu Glu Ser Ser Cys
    50                  55                  60

Asn Phe Asp Leu His Thr Thr Ser Met Ala Gln Lys Ser Phe Thr Gln
65                  70                  75                  80

Val Glu Trp Arg Lys Lys Ser Asp Thr Thr Asp Thr Thr Asn Ala Ala
                85                  90                  95

Ser Thr Thr Phe Glu Ala Gln Thr Lys Thr Val Asn Leu Arg Gly Thr
            100                 105                 110

Cys Ile Leu Ala Pro Glu Leu Tyr Asp Thr Leu Lys Lys Val Lys Lys
        115                 120                 125

Thr Val Leu Cys Tyr Asp Leu Thr Cys Asn Gln Thr His Cys Gln Pro
    130                 135                 140

Thr Val Tyr Leu Ile Ala Pro Val Leu Thr Cys Met Ser Ile Arg Ser
145                 150                 155                 160

Cys Met Ala Arg Val Phe Thr Ser Arg Ile Gln Val Ile Tyr Glu Lys
                165                 170                 175

Thr His Cys Val Thr Gly Gln Leu Ile Glu Gly Gln Cys Phe Asn Pro
            180                 185                 190
```

```
Ala His Thr Leu Thr Leu Ser Gln Pro Ala His Thr Tyr Asp Thr Val
        195                 200                 205

Thr Leu Pro Ile Ser Cys Phe Phe Thr Pro Lys Glu Ser Glu Gln Leu
210                 215                 220

Lys Val Ile Lys Thr Phe Glu Gly Ile Leu Thr Lys Thr Gly Cys Thr
225                 230                 235                 240

Glu Asn Ala Leu Gln Gly Tyr Tyr Val Cys Phe Leu Gly Ser His Ser
                245                 250                 255

Glu Pro Leu Ile Val Pro Ser Leu Glu Asp Ile Arg Ser Ala Glu Val
            260                 265                 270

Val Ser Arg Met Leu Val His Pro Arg Gly Glu Asp His Asp Ala Ile
        275                 280                 285

Gln Asn Ser Gln Ser His Leu Arg Ile Val Gly Pro Ile Thr Ala Lys
290                 295                 300

Val Pro Ser Thr Ser Ser Thr Asp Thr Leu Lys Gly Thr Ala Phe Ala
305                 310                 315                 320

Gly Val Pro Met Tyr Ser Ser Leu Ser Thr Leu Val Lys Asn Ala Asp
                325                 330                 335

Pro Glu Phe Val Phe Ser Pro Gly Ile Ile Pro Glu Ser Asn His Ser
            340                 345                 350

Val Cys Asp Lys Lys Thr Val Pro Ile Thr Trp Thr Gly Tyr Leu Pro
        355                 360                 365

Ile Ser Gly Glu Met Glu Lys Val Thr Gly Cys Thr Val Phe Cys Thr
370                 375                 380

Leu Ala Gly Pro Gly Ala Ser Cys Glu Ala Tyr Ser Glu Asn Gly Ile
385                 390                 395                 400

Phe Asn Ile Ser Ser Pro Thr Cys Leu Val Asn Lys Val Gln Arg Phe
                405                 410                 415

Arg Gly Ser Glu Gln Lys Ile Asn Phe Ile Cys Gln Arg Val Asp Gln
            420                 425                 430

Asp Val Val Val Tyr Cys Asn Gly Gln Lys Lys Val Ile Leu Thr Lys
        435                 440                 445

Thr Leu Val Ile Gly Gln Cys Ile Tyr Thr Phe Thr Ser Leu Phe Ser
450                 455                 460

Leu Met Pro Asp Val Ala His Ser Leu Ala Val Glu Leu Cys Val Pro
465                 470                 475                 480

Gly Leu His Gly Trp Ala Thr Val Met Leu Leu Ser Thr Phe Cys Phe
                485                 490                 495

Gly Trp Val Leu Ile Pro Ala Val Thr Leu Ile Ile Leu Lys Cys Leu
            500                 505                 510

Arg Val Leu Thr Phe Ser Cys Ser His Tyr Thr Asn Glu Ser Lys Phe
        515                 520                 525

Lys Phe Ile Leu Glu Lys Val Lys Val Glu Tyr Gln Lys Thr Met Gly
530                 535                 540

Ser Met Val Cys Asp Val Cys His His Glu Cys Glu Thr Ala Lys Glu
545                 550                 555                 560

Leu Glu Ser His Arg Gln Ser Cys Ile Asn Gly Gln Cys Pro Tyr Cys
                565                 570                 575

Met Thr Ile Thr Glu Ala Thr Glu Ser Ala Leu Gln Ala His Tyr Ser
            580                 585                 590

Ile Cys Lys Leu Thr Gly Arg Phe Gln Glu Ala Leu Lys Lys Ser Leu
        595                 600                 605

Lys Lys Pro Glu Val Lys Lys Gly Cys Tyr Arg Thr Leu Gly Val Phe
```

```
                610             615             620
Arg Tyr Lys Ser Arg Cys Tyr Val Gly Leu Val Trp Cys Leu Leu Leu
625             630             635             640

Thr Cys Glu Ile Val Ile Trp Ala Ala Ser Ala Glu Thr Pro Leu Met
            645             650             655

Glu Ser Gly Trp Ser Asp Thr Ala His Gly Val Gly Glu Ile Pro Met
            660             665             670

Lys Thr Asp Leu Glu Leu Asp Phe Ser Leu Pro Ser Ser Ser Ser Tyr
            675             680             685

Ser Tyr Arg Arg Lys Leu Thr Asn Pro Ala Asn Lys Glu Glu Ser Ile
            690             695             700

Ser Phe His Phe Gln Met Glu Lys Gln Val Ile His Ala Glu Ile Gln
705             710             715             720

Pro Leu Gly His Trp Met Asp Ala Thr Phe Asn Thr Lys Thr Ala Phe
            725             730             735

His Cys Tyr Gly Ala Cys Gln Lys Tyr Ser Tyr Pro Trp Gln Thr Ser
            740             745             750

Lys Cys Phe Phe Glu Lys Asp Tyr Gln Tyr Glu Thr Gly Trp Gly Cys
            755             760             765

Asn Pro Gly Asp Cys Pro Gly Val Gly Thr Gly Cys Thr Ala Cys Gly
770             775             780

Val Tyr Leu Asp Lys Leu Lys Ser Val Gly Lys Ala Tyr Lys Ile Ile
785             790             795             800

Ser Leu Lys Tyr Thr Arg Lys Val Cys Ile Gln Leu Gly Thr Glu Gln
            805             810             815

Thr Cys Lys His Ile Asp Ala Asn Asp Cys Leu Val Thr Pro Ser Val
            820             825             830

Lys Val Cys Ile Val Gly Thr Val Ser Lys Leu Gln Pro Ser Asp Thr
            835             840             845

Leu Leu Phe Leu Gly Pro Leu Glu Gln Gly Gly Val Ile Leu Lys Gln
            850             855             860

Trp Cys Thr Thr Ser Cys Ala Phe Gly Asp Pro Gly Asp Ile Met Ser
865             870             875             880

Thr Pro Ser Gly Met Arg Cys Pro Glu His Thr Gly Ser Phe Arg Lys
            885             890             895

Ile Cys Gly Phe Ala Thr Thr Pro Val Cys Glu Tyr Gln Gly Asn Thr
            900             905             910

Ile Ser Gly Tyr Lys Arg Met Met Ala Thr Lys Asp Ser Phe Gln Ser
            915             920             925

Phe Asn Leu Thr Glu Pro His Ile Thr Ala Asn Lys Leu Glu Trp Ile
930             935             940

Asp Pro Asp Gly Asn Thr Arg Asp Cys Val Asn Leu Val Leu Asn Arg
945             950             955             960

Asp Val Ser Phe Gln Asp Leu Ser Asp Asn Pro Cys Lys Val Asp Leu
            965             970             975

His Thr Gln Ala Ile Glu Gly Ala Trp Gly Ser Gly Val Gly Phe Thr
            980             985             990

Leu Thr Cys Thr Val Gly Leu Thr Glu Cys Pro Ser Phe Met Thr Ser
            995             1000            1005

Ile Lys Ala Cys Asp Leu Ala Met Cys Tyr Gly Ser Thr Val Ala
    1010            1015            1020

Asn Leu Ala Arg Gly Ser Asn Thr Val Lys Val Val Gly Lys Gly
    1025            1030            1035
```

```
Gly His Ser Gly Ser Ser Phe Lys Cys Cys His Asp Thr Asp Cys
    1040                1045                1050

Ser Ser Glu Gly Leu Leu Ala Ser Ala Pro His Leu Glu Arg Val
    1055                1060                1065

Thr Gly Phe Asn Gln Ile Asp Ser Asp Lys Val Tyr Asp Asp Gly
    1070                1075                1080

Ala Pro Pro Cys Thr Phe Lys Cys Trp Phe Thr Lys Ser Gly Glu
    1085                1090                1095

Trp Leu Leu Gly Ile Leu Asn Gly Asn Trp Ile Val Val Val Val
    1100                1105                1110

Leu Val Val Ile Leu Ile Leu Ser Ile Ile Met Phe Ser Val Leu
    1115                1120                1125

Cys Pro Arg Arg Gly His Lys Lys Thr Val
    1130                1135

<210> SEQ ID NO 5
<211> LENGTH: 1138
<212> TYPE: PRT
<213> ORGANISM: Artificial Sequence
<220> FEATURE:
<223> OTHER INFORMATION: Synthetic: ANDV GPC H953F

<400> SEQUENCE: 5

Met Glu Gly Trp Tyr Leu Val Ala Leu Gly Ile Cys Tyr Thr Leu
  1               5                  10                  15

Leu Ala Met Pro Lys Thr Thr Tyr Glu Leu Lys Met Glu Cys Pro His
             20                  25                  30

Thr Val Gly Leu Gly Gln Gly Tyr Ile Ile Gly Ser Thr Glu Leu Gly
         35                  40                  45

Leu Ile Ser Ile Glu Ala Ala Ser Asp Ile Lys Leu Glu Ser Ser Cys
 50                  55                  60

Asn Phe Asp Leu His Thr Thr Ser Met Ala Gln Lys Ser Phe Thr Gln
 65                  70                  75                  80

Val Glu Trp Arg Lys Lys Ser Asp Thr Thr Asp Thr Asn Ala Ala
                 85                  90                  95

Ser Thr Thr Phe Glu Ala Gln Thr Lys Thr Val Asn Leu Arg Gly Thr
            100                 105                 110

Cys Ile Leu Ala Pro Glu Leu Tyr Asp Thr Leu Lys Lys Val Lys Lys
            115                 120                 125

Thr Val Leu Cys Tyr Asp Leu Thr Cys Asn Gln Thr His Cys Gln Pro
130                 135                 140

Thr Val Tyr Leu Ile Ala Pro Val Leu Thr Cys Met Ser Ile Arg Ser
145                 150                 155                 160

Cys Met Ala Arg Val Phe Thr Ser Arg Ile Gln Val Ile Tyr Glu Lys
                165                 170                 175

Thr His Cys Val Thr Gly Gln Leu Ile Glu Gly Gln Cys Phe Asn Pro
            180                 185                 190

Ala His Thr Leu Thr Leu Ser Gln Pro Ala His Thr Tyr Asp Thr Val
            195                 200                 205

Thr Leu Pro Ile Ser Cys Phe Phe Thr Pro Lys Glu Ser Glu Gln Leu
    210                 215                 220

Lys Val Ile Lys Thr Phe Glu Gly Ile Leu Lys Thr Gly Cys Thr
225                 230                 235                 240

Glu Asn Ala Leu Gln Gly Tyr Tyr Val Cys Phe Leu Gly Ser His Ser
                245                 250                 255
```

```
Glu Pro Leu Ile Val Pro Ser Leu Glu Asp Ile Arg Ser Ala Glu Val
            260                 265                 270

Val Ser Arg Met Leu Val His Pro Arg Gly Glu Asp His Asp Ala Ile
275                 280                 285

Gln Asn Ser Gln Ser His Leu Arg Ile Val Gly Pro Ile Thr Ala Lys
        290                 295                 300

Val Pro Ser Thr Ser Ser Thr Asp Thr Leu Lys Gly Thr Ala Phe Ala
305                 310                 315                 320

Gly Val Pro Met Tyr Ser Ser Leu Ser Thr Leu Val Lys Asn Ala Asp
                    325                 330                 335

Pro Glu Phe Val Phe Ser Pro Gly Ile Ile Pro Glu Ser Asn His Ser
                340                 345                 350

Val Cys Asp Lys Lys Thr Val Pro Ile Thr Trp Thr Gly Tyr Leu Pro
            355                 360                 365

Ile Ser Gly Glu Met Glu Lys Val Thr Gly Cys Thr Val Phe Cys Thr
370                 375                 380

Leu Ala Gly Pro Gly Ala Ser Cys Glu Ala Tyr Ser Glu Asn Gly Ile
385                 390                 395                 400

Phe Asn Ile Ser Ser Pro Thr Cys Leu Val Asn Lys Val Gln Arg Phe
                    405                 410                 415

Arg Gly Ser Glu Gln Lys Ile Asn Phe Ile Cys Gln Arg Val Asp Gln
                420                 425                 430

Asp Val Val Val Tyr Cys Asn Gly Gln Lys Lys Val Ile Leu Thr Lys
            435                 440                 445

Thr Leu Val Ile Gly Gln Cys Ile Tyr Thr Phe Thr Ser Leu Phe Ser
450                 455                 460

Leu Met Pro Asp Val Ala His Ser Leu Ala Val Glu Leu Cys Val Pro
465                 470                 475                 480

Gly Leu His Gly Trp Ala Thr Val Met Leu Leu Ser Thr Phe Cys Phe
                    485                 490                 495

Gly Trp Val Leu Ile Pro Ala Val Thr Leu Ile Ile Leu Lys Cys Leu
                500                 505                 510

Arg Val Leu Thr Phe Ser Cys Ser His Tyr Thr Asn Glu Ser Lys Phe
            515                 520                 525

Lys Phe Ile Leu Glu Lys Val Lys Val Glu Tyr Gln Lys Thr Met Gly
530                 535                 540

Ser Met Val Cys Asp Val Cys His His Glu Cys Glu Thr Ala Lys Glu
545                 550                 555                 560

Leu Glu Ser His Arg Gln Ser Cys Ile Asn Gly Gln Cys Pro Tyr Cys
                    565                 570                 575

Met Thr Ile Thr Glu Ala Thr Glu Ser Ala Leu Gln Ala His Tyr Ser
                580                 585                 590

Ile Cys Lys Leu Thr Gly Arg Phe Gln Glu Ala Leu Lys Lys Ser Leu
            595                 600                 605

Lys Lys Pro Glu Val Lys Lys Gly Cys Tyr Arg Thr Leu Gly Val Phe
610                 615                 620

Arg Tyr Lys Ser Arg Cys Tyr Val Gly Leu Val Trp Cys Leu Leu Leu
625                 630                 635                 640

Thr Cys Glu Ile Val Ile Trp Ala Ala Ser Ala Glu Thr Pro Leu Met
                    645                 650                 655

Glu Ser Gly Trp Ser Asp Thr Ala His Gly Val Gly Glu Ile Pro Met
                660                 665                 670
```

```
Lys Thr Asp Leu Glu Leu Asp Phe Ser Leu Pro Ser Ser Ser Tyr
            675                 680                 685

Ser Tyr Arg Arg Lys Leu Thr Asn Pro Ala Asn Lys Glu Ser Ile
    690                 695                 700

Ser Phe His Phe Gln Met Glu Lys Gln Val Ile His Ala Glu Ile Gln
705                 710                 715                 720

Pro Leu Gly His Trp Met Asp Ala Thr Phe Asn Thr Lys Thr Ala Phe
                725                 730                 735

His Cys Tyr Gly Ala Cys Gln Lys Tyr Ser Tyr Pro Trp Gln Thr Ser
            740                 745                 750

Lys Cys Phe Phe Glu Lys Asp Tyr Gln Tyr Glu Thr Gly Trp Gly Cys
            755                 760                 765

Asn Pro Gly Asp Cys Pro Gly Val Gly Thr Gly Cys Thr Ala Cys Gly
            770                 775                 780

Val Tyr Leu Asp Lys Leu Lys Ser Val Gly Lys Ala Tyr Lys Ile Ile
785                 790                 795                 800

Ser Leu Lys Tyr Thr Arg Lys Val Cys Ile Gln Leu Gly Thr Glu Gln
                805                 810                 815

Thr Cys Lys His Ile Asp Ala Asn Asp Cys Leu Val Thr Pro Ser Val
            820                 825                 830

Lys Val Cys Ile Val Gly Thr Val Ser Lys Leu Gln Pro Ser Asp Thr
835                 840                 845

Leu Leu Phe Leu Gly Pro Leu Glu Gln Gly Gly Val Ile Leu Lys Gln
            850                 855                 860

Trp Cys Thr Thr Ser Cys Ala Phe Gly Asp Pro Gly Asp Ile Met Ser
865                 870                 875                 880

Thr Pro Ser Gly Met Arg Cys Pro Glu His Thr Gly Ser Phe Arg Lys
                885                 890                 895

Ile Cys Gly Phe Ala Thr Thr Pro Val Cys Glu Tyr Gln Gly Asn Thr
            900                 905                 910

Ile Ser Gly Tyr Lys Arg Met Met Ala Thr Lys Asp Ser Phe Gln Ser
            915                 920                 925

Phe Asn Leu Thr Glu Pro His Ile Thr Ala Asn Lys Leu Glu Trp Ile
            930                 935                 940

Asp Pro Asp Gly Asn Thr Arg Asp Phe Val Asn Leu Val Leu Asn Arg
945                 950                 955                 960

Asp Val Ser Phe Gln Asp Leu Ser Asp Asn Pro Cys Lys Val Asp Leu
                965                 970                 975

His Thr Gln Ala Ile Glu Gly Ala Trp Gly Ser Gly Val Gly Phe Thr
            980                 985                 990

Leu Thr Cys Thr Val Gly Leu Thr Glu Cys Pro Ser Phe Met Thr Ser
            995                 1000                1005

Ile Lys Ala Cys Asp Leu Ala Met Cys Tyr Gly Ser Thr Val Ala
    1010                1015                1020

Asn Leu Ala Arg Gly Ser Asn Thr Val Lys Val Val Gly Lys Gly
    1025                1030                1035

Gly His Ser Gly Ser Ser Phe Lys Cys Cys His Asp Thr Asp Cys
    1040                1045                1050

Ser Ser Glu Gly Leu Leu Ala Ser Ala Pro His Leu Glu Arg Val
    1055                1060                1065

Thr Gly Phe Asn Gln Ile Asp Ser Asp Lys Val Tyr Asp Asp Gly
    1070                1075                1080

Ala Pro Pro Cys Thr Phe Lys Cys Trp Phe Thr Lys Ser Gly Glu
```

-continued

```
                1085                1090                1095

Trp Leu Leu Gly Ile Leu Asn Gly Asn Trp Ile Val Val Val Val
            1100                1105                1110

Leu Val Val Ile Leu Ile Leu Ser Ile Ile Met Phe Ser Val Leu
        1115                1120                1125

Cys Pro Arg Arg Gly His Lys Lys Thr Val
        1130                1135

<210> SEQ ID NO 6
<211> LENGTH: 1138
<212> TYPE: PRT
<213> ORGANISM: Artificial Sequence
<220> FEATURE:
<223> OTHER INFORMATION: Synthetic: ANDV GPC Q844C/H953C

<400> SEQUENCE: 6

Met Glu Gly Trp Tyr Leu Val Ala Leu Gly Ile Cys Tyr Thr Leu Thr
1               5                   10                  15

Leu Ala Met Pro Lys Thr Thr Tyr Glu Leu Lys Met Glu Cys Pro His
            20                  25                  30

Thr Val Gly Leu Gly Gln Gly Tyr Ile Ile Gly Ser Thr Glu Leu Gly
        35                  40                  45

Leu Ile Ser Ile Glu Ala Ala Ser Asp Ile Lys Leu Glu Ser Ser Cys
    50                  55                  60

Asn Phe Asp Leu His Thr Thr Ser Met Ala Gln Lys Ser Phe Thr Gln
65                  70                  75                  80

Val Glu Trp Arg Lys Lys Ser Asp Thr Thr Asp Thr Thr Asn Ala Ala
                85                  90                  95

Ser Thr Thr Phe Glu Ala Gln Thr Lys Thr Val Asn Leu Arg Gly Thr
            100                 105                 110

Cys Ile Leu Ala Pro Glu Leu Tyr Asp Thr Leu Lys Lys Val Lys Lys
        115                 120                 125

Thr Val Leu Cys Tyr Asp Leu Thr Cys Asn Gln Thr His Cys Gln Pro
    130                 135                 140

Thr Val Tyr Leu Ile Ala Pro Val Leu Thr Cys Met Ser Ile Arg Ser
145                 150                 155                 160

Cys Met Ala Arg Val Phe Thr Ser Arg Ile Gln Val Ile Tyr Glu Lys
                165                 170                 175

Thr His Cys Val Thr Gly Gln Leu Ile Glu Gly Gln Cys Phe Asn Pro
            180                 185                 190

Ala His Thr Leu Thr Leu Ser Gln Pro Ala His Thr Tyr Asp Thr Val
        195                 200                 205

Thr Leu Pro Ile Ser Cys Phe Phe Thr Pro Lys Glu Ser Glu Gln Leu
    210                 215                 220

Lys Val Ile Lys Thr Phe Glu Gly Ile Leu Thr Lys Thr Gly Cys Thr
225                 230                 235                 240

Glu Asn Ala Leu Gln Gly Tyr Tyr Val Cys Phe Leu Gly Ser His Ser
                245                 250                 255

Glu Pro Leu Ile Val Pro Ser Leu Glu Asp Ile Arg Ser Ala Glu Val
            260                 265                 270

Val Ser Arg Met Leu Val His Pro Arg Gly Glu Asp His Asp Ala Ile
        275                 280                 285

Gln Asn Ser Gln Ser His Leu Arg Ile Val Gly Pro Ile Thr Ala Lys
    290                 295                 300

Val Pro Ser Thr Ser Ser Thr Asp Thr Leu Lys Gly Thr Ala Phe Ala
```

```
                        305                 310                 315                 320
Gly Val Pro Met Tyr Ser Ser Leu Ser Thr Leu Val Lys Asn Ala Asp
                    325                 330                 335

Pro Glu Phe Val Phe Ser Pro Gly Ile Ile Pro Glu Ser Asn His Ser
                340                 345                 350

Val Cys Asp Lys Lys Thr Val Pro Ile Thr Trp Thr Gly Tyr Leu Pro
            355                 360                 365

Ile Ser Gly Glu Met Glu Lys Val Thr Gly Cys Thr Val Phe Cys Thr
        370                 375                 380

Leu Ala Gly Pro Gly Ala Ser Cys Glu Ala Tyr Ser Glu Asn Gly Ile
385                 390                 395                 400

Phe Asn Ile Ser Ser Pro Thr Cys Leu Val Asn Lys Val Gln Arg Phe
                405                 410                 415

Arg Gly Ser Glu Gln Lys Ile Asn Phe Ile Cys Gln Arg Val Asp Gln
            420                 425                 430

Asp Val Val Val Tyr Cys Asn Gly Gln Lys Lys Val Ile Leu Thr Lys
        435                 440                 445

Thr Leu Val Ile Gly Gln Cys Ile Tyr Thr Phe Thr Ser Leu Phe Ser
    450                 455                 460

Leu Met Pro Asp Val Ala His Ser Leu Ala Val Glu Leu Cys Val Pro
465                 470                 475                 480

Gly Leu His Gly Trp Ala Thr Val Met Leu Leu Ser Thr Phe Cys Phe
                485                 490                 495

Gly Trp Val Leu Ile Pro Ala Val Thr Leu Ile Ile Leu Lys Cys Leu
            500                 505                 510

Arg Val Leu Thr Phe Ser Cys Ser His Tyr Thr Asn Glu Ser Lys Phe
        515                 520                 525

Lys Phe Ile Leu Glu Lys Val Lys Val Glu Tyr Gln Lys Thr Met Gly
    530                 535                 540

Ser Met Val Cys Asp Val Cys His His Glu Cys Glu Thr Ala Lys Glu
545                 550                 555                 560

Leu Glu Ser His Arg Gln Ser Cys Ile Asn Gly Gln Cys Pro Tyr Cys
                565                 570                 575

Met Thr Ile Thr Glu Ala Thr Glu Ser Ala Leu Gln Ala His Tyr Ser
            580                 585                 590

Ile Cys Lys Leu Thr Gly Arg Phe Gln Glu Ala Leu Lys Lys Ser Leu
        595                 600                 605

Lys Lys Pro Glu Val Lys Lys Gly Cys Tyr Arg Thr Leu Gly Val Phe
    610                 615                 620

Arg Tyr Lys Ser Arg Cys Tyr Val Gly Leu Val Trp Cys Leu Leu Leu
625                 630                 635                 640

Thr Cys Glu Ile Val Ile Trp Ala Ala Ser Ala Glu Thr Pro Leu Met
                645                 650                 655

Glu Ser Gly Trp Ser Asp Thr His Gly Val Gly Glu Ile Pro Met
            660                 665                 670

Lys Thr Asp Leu Glu Leu Asp Phe Ser Leu Pro Ser Ser Ser Tyr
        675                 680                 685

Ser Tyr Arg Arg Lys Leu Thr Asn Pro Ala Asn Lys Glu Glu Ser Ile
    690                 695                 700

Ser Phe His Phe Gln Met Glu Lys Gln Val Ile His Ala Glu Ile Gln
705                 710                 715                 720

Pro Leu Gly His Trp Met Asp Ala Thr Phe Asn Thr Lys Thr Ala Phe
                725                 730                 735
```

```
His Cys Tyr Gly Ala Cys Gln Lys Tyr Ser Tyr Pro Trp Gln Thr Ser
             740                 745                 750

Lys Cys Phe Phe Glu Lys Asp Tyr Gln Tyr Glu Thr Gly Trp Gly Cys
             755                 760                 765

Asn Pro Gly Asp Cys Pro Gly Val Gly Thr Gly Cys Thr Ala Cys Gly
    770                 775                 780

Val Tyr Leu Asp Lys Leu Lys Ser Val Gly Lys Ala Tyr Lys Ile Ile
785                 790                 795                 800

Ser Leu Lys Tyr Thr Arg Lys Val Cys Ile Gln Leu Gly Thr Glu Gln
             805                 810                 815

Thr Cys Lys His Ile Asp Ala Asn Asp Cys Leu Val Thr Pro Ser Val
             820                 825                 830

Lys Val Cys Ile Val Gly Thr Val Ser Lys Leu Cys Pro Ser Asp Thr
             835                 840                 845

Leu Leu Phe Leu Gly Pro Leu Glu Gln Gly Gly Val Ile Leu Lys Gln
    850                 855                 860

Trp Cys Thr Thr Ser Cys Ala Phe Gly Asp Pro Gly Asp Ile Met Ser
865                 870                 875                 880

Thr Pro Ser Gly Met Arg Cys Pro Glu His Thr Gly Ser Phe Arg Lys
             885                 890                 895

Ile Cys Gly Phe Ala Thr Thr Pro Val Cys Glu Tyr Gln Gly Asn Thr
             900                 905                 910

Ile Ser Gly Tyr Lys Arg Met Met Ala Thr Lys Asp Ser Phe Gln Ser
             915                 920                 925

Phe Asn Leu Thr Glu Pro His Ile Thr Ala Asn Lys Leu Glu Trp Ile
    930                 935                 940

Asp Pro Asp Gly Asn Thr Arg Asp Cys Val Asn Leu Val Leu Asn Arg
945                 950                 955                 960

Asp Val Ser Phe Gln Asp Leu Ser Asp Asn Pro Cys Lys Val Asp Leu
             965                 970                 975

His Thr Gln Ala Ile Glu Gly Ala Trp Gly Ser Gly Val Gly Phe Thr
             980                 985                 990

Leu Thr Cys Thr Val Gly Leu Thr  Glu Cys Pro Ser Phe  Met Thr Ser
             995                1000                1005

Ile Lys  Ala Cys Asp Leu Ala  Met Cys Tyr Gly Ser  Thr Val Ala
    1010                1015                1020

Asn Leu  Ala Arg Gly Ser Asn  Thr Val Lys Val Val  Gly Lys Gly
    1025                1030                1035

Gly His  Ser Gly Ser Ser Phe  Lys Cys Cys His Asp  Thr Asp Cys
    1040                1045                1050

Ser Ser  Glu Gly Leu Leu Ala  Ser Ala Pro His Leu  Glu Arg Val
    1055                1060                1065

Thr Gly  Phe Asn Gln Ile Asp  Ser Asp Lys Val Tyr  Asp Asp Gly
    1070                1075                1080

Ala Pro  Pro Cys Thr Phe Lys  Cys Trp Phe Thr Lys  Ser Gly Glu
    1085                1090                1095

Trp Leu  Leu Gly Ile Leu Asn  Gly Asn Trp Ile Val  Val Val Val
    1100                1105                1110

Leu Val  Val Ile Leu Ile Leu  Ser Ile Ile Met Phe  Ser Val Leu
    1115                1120                1125

Cys Pro  Arg Arg Gly His Lys  Lys Thr Val
    1130                1135
```

<210> SEQ ID NO 7
<211> LENGTH: 1138
<212> TYPE: PRT
<213> ORGANISM: Artificial Sequence
<220> FEATURE:
<223> OTHER INFORMATION: Synthetic: ANDV GPC H294C/T734C

<400> SEQUENCE: 7

```
Met Glu Gly Trp Tyr Leu Val Ala Leu Gly Ile Cys Tyr Thr Leu Thr
1               5                   10                  15

Leu Ala Met Pro Lys Thr Thr Tyr Glu Leu Lys Met Glu Cys Pro His
                20                  25                  30

Thr Val Gly Leu Gly Gln Gly Tyr Ile Ile Gly Ser Thr Glu Leu Gly
            35                  40                  45

Leu Ile Ser Ile Glu Ala Ala Ser Asp Ile Lys Leu Glu Ser Ser Cys
        50                  55                  60

Asn Phe Asp Leu His Thr Thr Ser Met Ala Gln Lys Ser Phe Thr Gln
65                  70                  75                  80

Val Glu Trp Arg Lys Lys Ser Asp Thr Thr Asp Thr Asn Ala Ala
                85                  90                  95

Ser Thr Thr Phe Glu Ala Gln Thr Lys Thr Val Asn Leu Arg Gly Thr
            100                 105                 110

Cys Ile Leu Ala Pro Glu Leu Tyr Asp Thr Leu Lys Lys Val Lys Lys
        115                 120                 125

Thr Val Leu Cys Tyr Asp Leu Thr Cys Asn Gln Thr His Cys Gln Pro
130                 135                 140

Thr Val Tyr Leu Ile Ala Pro Val Leu Thr Cys Met Ser Ile Arg Ser
145                 150                 155                 160

Cys Met Ala Arg Val Phe Thr Ser Arg Ile Gln Val Ile Tyr Glu Lys
                165                 170                 175

Thr His Cys Val Thr Gly Gln Leu Ile Glu Gly Gln Cys Phe Asn Pro
            180                 185                 190

Ala His Thr Leu Thr Leu Ser Gln Pro Ala His Thr Tyr Asp Thr Val
        195                 200                 205

Thr Leu Pro Ile Ser Cys Phe Phe Thr Pro Lys Glu Ser Glu Gln Leu
210                 215                 220

Lys Val Ile Lys Thr Phe Glu Gly Ile Leu Thr Lys Thr Gly Cys Thr
225                 230                 235                 240

Glu Asn Ala Leu Gln Gly Tyr Tyr Val Cys Phe Leu Gly Ser His Ser
                245                 250                 255

Glu Pro Leu Ile Val Pro Ser Leu Glu Asp Ile Arg Ser Ala Glu Val
            260                 265                 270

Val Ser Arg Met Leu Val His Pro Arg Gly Glu Asp His Asp Ala Ile
        275                 280                 285

Gln Asn Ser Gln Ser Cys Leu Arg Ile Val Gly Pro Ile Thr Ala Lys
290                 295                 300

Val Pro Ser Thr Ser Ser Thr Asp Thr Leu Lys Gly Thr Ala Phe Ala
305                 310                 315                 320

Gly Val Pro Met Tyr Ser Ser Leu Ser Thr Leu Val Lys Asn Ala Asp
                325                 330                 335

Pro Glu Phe Val Phe Ser Pro Gly Ile Ile Pro Glu Ser Asn His Ser
            340                 345                 350

Val Cys Asp Lys Lys Thr Val Pro Ile Thr Trp Thr Gly Tyr Leu Pro
        355                 360                 365
```

```
Ile Ser Gly Glu Met Glu Lys Val Thr Gly Cys Thr Val Phe Cys Thr
370                 375                 380
Leu Ala Gly Pro Gly Ala Ser Cys Glu Ala Tyr Ser Glu Asn Gly Ile
385                 390                 395                 400
Phe Asn Ile Ser Ser Pro Thr Cys Leu Val Asn Lys Val Gln Arg Phe
                405                 410                 415
Arg Gly Ser Glu Gln Lys Ile Asn Phe Ile Cys Gln Arg Val Asp Gln
            420                 425                 430
Asp Val Val Tyr Cys Asn Gly Gln Lys Lys Val Ile Leu Thr Lys
                435                 440                 445
Thr Leu Val Ile Gly Gln Cys Ile Tyr Thr Phe Thr Ser Leu Phe Ser
450                 455                 460
Leu Met Pro Asp Val Ala His Ser Leu Ala Val Glu Leu Cys Val Pro
465                 470                 475                 480
Gly Leu His Gly Trp Ala Thr Val Met Leu Leu Ser Thr Phe Cys Phe
                485                 490                 495
Gly Trp Val Leu Ile Pro Ala Val Thr Leu Ile Ile Leu Lys Cys Leu
            500                 505                 510
Arg Val Leu Thr Phe Ser Cys Ser His Tyr Thr Asn Glu Ser Lys Phe
                515                 520                 525
Lys Phe Ile Leu Glu Lys Val Lys Val Glu Tyr Gln Lys Thr Met Gly
530                 535                 540
Ser Met Val Cys Asp Val Cys His His Glu Cys Glu Thr Ala Lys Glu
545                 550                 555                 560
Leu Glu Ser His Arg Gln Ser Cys Ile Asn Gly Gln Cys Pro Tyr Cys
                565                 570                 575
Met Thr Ile Thr Glu Ala Thr Glu Ser Ala Leu Gln Ala His Tyr Ser
            580                 585                 590
Ile Cys Lys Leu Thr Gly Arg Phe Gln Glu Ala Leu Lys Lys Ser Leu
                595                 600                 605
Lys Lys Pro Glu Val Lys Lys Gly Cys Tyr Arg Thr Leu Gly Val Phe
610                 615                 620
Arg Tyr Lys Ser Arg Cys Tyr Val Gly Leu Val Trp Cys Leu Leu Leu
625                 630                 635                 640
Thr Cys Glu Ile Val Ile Trp Ala Ala Ser Ala Glu Thr Pro Leu Met
                645                 650                 655
Glu Ser Gly Trp Ser Asp Thr Ala His Gly Val Gly Glu Ile Pro Met
            660                 665                 670
Lys Thr Asp Leu Glu Leu Asp Phe Ser Leu Pro Ser Ser Ser Ser Tyr
                675                 680                 685
Ser Tyr Arg Arg Lys Leu Thr Asn Pro Ala Asn Lys Glu Glu Ser Ile
690                 695                 700
Ser Phe His Phe Gln Met Glu Lys Gln Val Ile His Ala Glu Ile Gln
705                 710                 715                 720
Pro Leu Gly His Trp Met Asp Ala Thr Phe Asn Thr Lys Cys Ala Phe
                725                 730                 735
His Cys Tyr Gly Ala Cys Gln Lys Tyr Ser Tyr Pro Trp Gln Thr Ser
            740                 745                 750
Lys Cys Phe Phe Glu Lys Asp Tyr Gln Tyr Glu Thr Gly Trp Gly Cys
                755                 760                 765
Asn Pro Gly Asp Cys Pro Gly Val Gly Thr Gly Cys Thr Ala Cys Gly
770                 775                 780
Val Tyr Leu Asp Lys Leu Lys Ser Val Gly Lys Ala Tyr Lys Ile Ile
```

```
                785                 790                 795                 800
Ser Leu Lys Tyr Thr Arg Lys Val Cys Ile Gln Leu Gly Thr Glu Gln
                    805                 810                 815

Thr Cys Lys His Ile Asp Ala Asn Asp Cys Leu Val Thr Pro Ser Val
                820                 825                 830

Lys Val Cys Ile Val Gly Thr Val Ser Lys Leu Gln Pro Ser Asp Thr
                835                 840                 845

Leu Leu Phe Leu Gly Pro Leu Glu Gln Gly Gly Val Ile Leu Lys Gln
            850                 855                 860

Trp Cys Thr Thr Ser Cys Ala Phe Gly Asp Pro Gly Asp Ile Met Ser
865                 870                 875                 880

Thr Pro Ser Gly Met Arg Cys Pro Glu His Thr Gly Ser Phe Arg Lys
                    885                 890                 895

Ile Cys Gly Phe Ala Thr Thr Pro Val Cys Glu Tyr Gln Gly Asn Thr
                900                 905                 910

Ile Ser Gly Tyr Lys Arg Met Met Ala Thr Lys Asp Ser Phe Gln Ser
                915                 920                 925

Phe Asn Leu Thr Glu Pro His Ile Thr Ala Asn Lys Leu Glu Trp Ile
            930                 935                 940

Asp Pro Asp Gly Asn Thr Arg Asp His Val Asn Leu Val Leu Asn Arg
945                 950                 955                 960

Asp Val Ser Phe Gln Asp Leu Ser Asp Asn Pro Cys Lys Val Asp Leu
                    965                 970                 975

His Thr Gln Ala Ile Glu Gly Ala Trp Gly Ser Gly Val Gly Phe Thr
                980                 985                 990

Leu Thr Cys Thr Val Gly Leu Thr  Glu Cys Pro Ser Phe  Met Thr Ser
                995                 1000                1005

Ile Lys  Ala Cys Asp Leu Ala  Met Cys Tyr Gly Ser  Thr Val Ala
        1010                1015                1020

Asn Leu  Ala Arg Gly Ser Asn  Thr Val Lys Val Val  Gly Lys Gly
        1025                1030                1035

Gly His  Ser Gly Ser Ser Phe  Lys Cys Cys His Asp  Thr Asp Cys
        1040                1045                1050

Ser Ser  Glu Gly Leu Leu Ala  Ser Ala Pro His Leu  Glu Arg Val
        1055                1060                1065

Thr Gly  Phe Asn Gln Ile Asp  Ser Asp Lys Val Tyr  Asp Asp Gly
        1070                1075                1080

Ala Pro  Pro Cys Thr Phe Lys  Cys Trp Phe Thr Lys  Ser Gly Glu
        1085                1090                1095

Trp Leu  Leu Gly Ile Leu Asn  Gly Asn Trp Ile Val  Val Val Val
        1100                1105                1110

Leu Val  Val Ile Leu Ile Leu  Ser Ile Ile Met Phe  Ser Val Leu
        1115                1120                1125

Cys Pro  Arg Arg Gly His Lys  Lys Thr Val
        1130                1135

<210> SEQ ID NO 8
<211> LENGTH: 1138
<212> TYPE: PRT
<213> ORGANISM: Artificial Sequence
<220> FEATURE:
<223> OTHER INFORMATION: Synthetic: ANDV GPC R281C/P748C

<400> SEQUENCE: 8

Met Glu Gly Trp Tyr Leu Val Ala Leu Gly Ile Cys Tyr Thr Leu Thr
```

-continued

```
1               5                   10                  15
Leu Ala Met Pro Lys Thr Thr Tyr Glu Leu Lys Met Glu Cys Pro His
            20                  25                  30
Thr Val Gly Leu Gly Gln Gly Tyr Ile Ile Gly Ser Thr Glu Leu Gly
            35                  40                  45
Leu Ile Ser Ile Glu Ala Ala Ser Asp Ile Lys Leu Glu Ser Ser Cys
50                  55                  60
Asn Phe Asp Leu His Thr Thr Ser Met Ala Gln Lys Ser Phe Thr Gln
65                  70                  75                  80
Val Glu Trp Arg Lys Lys Ser Asp Thr Thr Asp Thr Thr Asn Ala Ala
            85                  90                  95
Ser Thr Thr Phe Glu Ala Gln Thr Lys Thr Val Asn Leu Arg Gly Thr
            100                 105                 110
Cys Ile Leu Ala Pro Glu Leu Tyr Asp Thr Leu Lys Lys Val Lys Lys
            115                 120                 125
Thr Val Leu Cys Tyr Asp Leu Thr Cys Asn Gln Thr His Cys Gln Pro
            130                 135                 140
Thr Val Tyr Leu Ile Ala Pro Val Leu Thr Cys Met Ser Ile Arg Ser
145                 150                 155                 160
Cys Met Ala Arg Val Phe Thr Ser Arg Ile Gln Val Ile Tyr Glu Lys
            165                 170                 175
Thr His Cys Val Thr Gly Gln Leu Ile Glu Gly Gln Cys Phe Asn Pro
            180                 185                 190
Ala His Thr Leu Thr Leu Ser Gln Pro Ala His Thr Tyr Asp Thr Val
            195                 200                 205
Thr Leu Pro Ile Ser Cys Phe Phe Thr Pro Lys Glu Ser Glu Gln Leu
            210                 215                 220
Lys Val Ile Lys Thr Phe Glu Gly Ile Leu Thr Lys Thr Gly Cys Thr
225                 230                 235                 240
Glu Asn Ala Leu Gln Gly Tyr Tyr Val Cys Phe Leu Gly Ser His Ser
            245                 250                 255
Glu Pro Leu Ile Val Pro Ser Leu Glu Asp Ile Arg Ser Ala Glu Val
            260                 265                 270
Val Ser Arg Met Leu Val His Pro Cys Gly Glu Asp His Asp Ala Ile
            275                 280                 285
Gln Asn Ser Gln Ser His Leu Arg Ile Val Gly Pro Ile Thr Ala Lys
            290                 295                 300
Val Pro Ser Thr Ser Ser Thr Asp Thr Leu Lys Gly Thr Ala Phe Ala
305                 310                 315                 320
Gly Val Pro Met Tyr Ser Ser Leu Ser Thr Leu Val Lys Asn Ala Asp
            325                 330                 335
Pro Glu Phe Val Phe Ser Pro Gly Ile Ile Pro Glu Ser Asn His Ser
            340                 345                 350
Val Cys Asp Lys Lys Thr Val Pro Ile Thr Trp Thr Gly Tyr Leu Pro
            355                 360                 365
Ile Ser Gly Glu Met Glu Lys Val Thr Gly Cys Thr Val Phe Cys Thr
            370                 375                 380
Leu Ala Gly Pro Gly Ala Ser Cys Glu Ala Tyr Ser Glu Asn Gly Ile
385                 390                 395                 400
Phe Asn Ile Ser Ser Pro Thr Cys Leu Val Asn Lys Val Gln Arg Phe
            405                 410                 415
Arg Gly Ser Glu Gln Lys Ile Asn Phe Ile Cys Gln Arg Val Asp Gln
            420                 425                 430
```

```
Asp Val Val Tyr Cys Asn Gly Gln Lys Val Ile Leu Thr Lys
        435                 440                 445

Thr Leu Val Ile Gly Gln Cys Ile Tyr Thr Phe Thr Ser Leu Phe Ser
    450                 455                 460

Leu Met Pro Asp Val Ala His Ser Leu Ala Val Glu Leu Cys Val Pro
465                 470                 475                 480

Gly Leu His Gly Trp Ala Thr Val Met Leu Leu Ser Thr Phe Cys Phe
                485                 490                 495

Gly Trp Val Leu Ile Pro Ala Val Thr Leu Ile Ile Leu Lys Cys Leu
            500                 505                 510

Arg Val Leu Thr Phe Ser Cys Ser His Tyr Thr Asn Glu Ser Lys Phe
        515                 520                 525

Lys Phe Ile Leu Glu Lys Val Lys Val Glu Tyr Gln Lys Thr Met Gly
    530                 535                 540

Ser Met Val Cys Asp Val Cys His His Glu Cys Glu Thr Ala Lys Glu
545                 550                 555                 560

Leu Glu Ser His Arg Gln Ser Cys Ile Asn Gly Gln Cys Pro Tyr Cys
                565                 570                 575

Met Thr Ile Thr Glu Ala Thr Glu Ser Ala Leu Gln Ala His Tyr Ser
            580                 585                 590

Ile Cys Lys Leu Thr Gly Arg Phe Gln Glu Ala Leu Lys Lys Ser Leu
        595                 600                 605

Lys Lys Pro Glu Val Lys Lys Gly Cys Tyr Arg Thr Leu Gly Val Phe
    610                 615                 620

Arg Tyr Lys Ser Arg Cys Tyr Val Gly Leu Val Trp Cys Leu Leu Leu
625                 630                 635                 640

Thr Cys Glu Ile Val Ile Trp Ala Ala Ser Ala Glu Thr Pro Leu Met
                645                 650                 655

Glu Ser Gly Trp Ser Asp Thr Ala His Gly Val Gly Glu Ile Pro Met
            660                 665                 670

Lys Thr Asp Leu Glu Leu Asp Phe Ser Leu Pro Ser Ser Ser Ser Tyr
        675                 680                 685

Ser Tyr Arg Arg Lys Leu Thr Asn Pro Ala Asn Lys Glu Glu Ser Ile
    690                 695                 700

Ser Phe His Phe Gln Met Glu Lys Gln Val Ile His Ala Glu Ile Gln
705                 710                 715                 720

Pro Leu Gly His Trp Met Asp Ala Thr Phe Asn Thr Lys Thr Ala Phe
                725                 730                 735

His Cys Tyr Gly Ala Cys Gln Lys Tyr Ser Tyr Cys Trp Gln Thr Ser
            740                 745                 750

Lys Cys Phe Phe Glu Lys Asp Tyr Gln Tyr Glu Thr Gly Trp Gly Cys
        755                 760                 765

Asn Pro Gly Asp Cys Pro Gly Val Gly Thr Gly Cys Thr Ala Cys Gly
    770                 775                 780

Val Tyr Leu Asp Lys Leu Lys Ser Val Gly Lys Ala Tyr Lys Ile Ile
785                 790                 795                 800

Ser Leu Lys Tyr Thr Arg Lys Val Cys Ile Gln Leu Gly Thr Glu Gln
                805                 810                 815

Thr Cys Lys His Ile Asp Ala Asn Asp Cys Leu Val Thr Pro Ser Val
            820                 825                 830

Lys Val Cys Ile Val Gly Thr Val Ser Lys Leu Gln Pro Ser Asp Thr
        835                 840                 845
```

Leu Leu Phe Leu Gly Pro Leu Glu Gln Gly Gly Val Ile Leu Lys Gln
850                 855                 860

Trp Cys Thr Thr Ser Cys Ala Phe Gly Asp Pro Gly Asp Ile Met Ser
865                 870                 875                 880

Thr Pro Ser Gly Met Arg Cys Pro Glu His Thr Gly Ser Phe Arg Lys
            885                 890                 895

Ile Cys Gly Phe Ala Thr Thr Pro Val Cys Glu Tyr Gln Gly Asn Thr
            900                 905                 910

Ile Ser Gly Tyr Lys Arg Met Met Ala Thr Lys Asp Ser Phe Gln Ser
            915                 920                 925

Phe Asn Leu Thr Glu Pro His Ile Thr Ala Asn Lys Leu Glu Trp Ile
930                 935                 940

Asp Pro Asp Gly Asn Thr Arg Asp His Val Asn Leu Val Leu Asn Arg
945                 950                 955                 960

Asp Val Ser Phe Gln Asp Leu Ser Asp Asn Pro Cys Lys Val Asp Leu
            965                 970                 975

His Thr Gln Ala Ile Glu Gly Ala Trp Gly Ser Gly Val Gly Phe Thr
            980                 985                 990

Leu Thr Cys Thr Val Gly Leu Thr Glu Cys Pro Ser Phe Met Thr Ser
            995                 1000                1005

Ile Lys Ala Cys Asp Leu Ala Met Cys Tyr Gly Ser Thr Val Ala
    1010                1015                1020

Asn Leu Ala Arg Gly Ser Asn Thr Val Lys Val Val Gly Lys Gly
    1025                1030                1035

Gly His Ser Gly Ser Ser Phe Lys Cys Cys His Asp Thr Asp Cys
    1040                1045                1050

Ser Ser Glu Gly Leu Leu Ala Ser Ala Pro His Leu Glu Arg Val
    1055                1060                1065

Thr Gly Phe Asn Gln Ile Asp Ser Asp Lys Val Tyr Asp Asp Gly
    1070                1075                1080

Ala Pro Pro Cys Thr Phe Lys Cys Trp Phe Thr Lys Ser Gly Glu
    1085                1090                1095

Trp Leu Leu Gly Ile Leu Asn Gly Asn Trp Ile Val Val Val Val
    1100                1105                1110

Leu Val Val Ile Leu Ile Leu Ser Ile Ile Met Phe Ser Val Leu
    1115                1120                1125

Cys Pro Arg Arg Gly His Lys Lys Thr Val
    1130                1135

<210> SEQ ID NO 9
<211> LENGTH: 1138
<212> TYPE: PRT
<213> ORGANISM: Artificial Sequence
<220> FEATURE:
<223> OTHER INFORMATION: Synthetic: ANDV GPC T99C/P744C

<400> SEQUENCE: 9

Met Glu Gly Trp Tyr Leu Val Ala Leu Gly Ile Cys Tyr Thr Leu Thr
1               5                   10                  15

Leu Ala Met Pro Lys Thr Thr Tyr Glu Leu Lys Met Glu Cys Pro His
                20                  25                  30

Thr Val Gly Leu Gly Gln Gly Tyr Ile Ile Gly Ser Thr Glu Leu Gly
            35                  40                  45

Leu Ile Ser Ile Glu Ala Ala Ser Asp Ile Lys Leu Glu Ser Ser Cys
50                  55                  60

```
Asn Phe Asp Leu His Thr Thr Ser Met Ala Gln Lys Ser Phe Thr Gln
 65                  70                  75                  80

Val Glu Trp Arg Lys Lys Ser Asp Thr Thr Asp Thr Thr Asn Ala Ala
                 85                  90                  95

Ser Thr Cys Phe Glu Ala Gln Thr Lys Thr Val Asn Leu Arg Gly Thr
            100                 105                 110

Cys Ile Leu Ala Pro Glu Leu Tyr Asp Thr Leu Lys Lys Val Lys Lys
        115                 120                 125

Thr Val Leu Cys Tyr Asp Leu Thr Cys Asn Gln Thr His Cys Gln Pro
    130                 135                 140

Thr Val Tyr Leu Ile Ala Pro Val Leu Thr Cys Met Ser Ile Arg Ser
145                 150                 155                 160

Cys Met Ala Arg Val Phe Thr Ser Arg Ile Gln Val Ile Tyr Glu Lys
                165                 170                 175

Thr His Cys Val Thr Gly Gln Leu Ile Glu Gly Gln Cys Phe Asn Pro
            180                 185                 190

Ala His Thr Leu Thr Leu Ser Gln Pro Ala His Thr Tyr Asp Thr Val
        195                 200                 205

Thr Leu Pro Ile Ser Cys Phe Phe Thr Pro Lys Glu Ser Glu Gln Leu
    210                 215                 220

Lys Val Ile Lys Thr Phe Glu Gly Ile Leu Thr Lys Thr Gly Cys Thr
225                 230                 235                 240

Glu Asn Ala Leu Gln Gly Tyr Tyr Val Cys Phe Leu Gly Ser His Ser
                245                 250                 255

Glu Pro Leu Ile Val Pro Ser Leu Glu Asp Ile Arg Ser Ala Glu Val
            260                 265                 270

Val Ser Arg Met Leu Val His Pro Arg Gly Glu Asp His Asp Ala Ile
        275                 280                 285

Gln Asn Ser Gln Ser His Leu Arg Ile Val Gly Pro Ile Thr Ala Lys
    290                 295                 300

Val Pro Ser Thr Ser Ser Thr Asp Thr Leu Lys Gly Thr Ala Phe Ala
305                 310                 315                 320

Gly Val Pro Met Tyr Ser Ser Leu Ser Thr Leu Val Lys Asn Ala Asp
                325                 330                 335

Pro Glu Phe Val Phe Ser Pro Gly Ile Ile Pro Glu Ser Asn His Ser
            340                 345                 350

Val Cys Asp Lys Lys Thr Val Pro Ile Thr Trp Thr Gly Tyr Leu Pro
        355                 360                 365

Ile Ser Gly Glu Met Glu Lys Val Thr Gly Cys Thr Val Phe Cys Thr
    370                 375                 380

Leu Ala Gly Pro Gly Ala Ser Cys Glu Ala Tyr Ser Glu Asn Gly Ile
385                 390                 395                 400

Phe Asn Ile Ser Ser Pro Thr Cys Leu Val Asn Lys Val Gln Arg Phe
                405                 410                 415

Arg Gly Ser Glu Gln Lys Ile Asn Phe Ile Cys Gln Arg Val Asp Gln
            420                 425                 430

Asp Val Val Val Tyr Cys Asn Gly Gln Lys Lys Val Ile Leu Thr Lys
        435                 440                 445

Thr Leu Val Ile Gly Gln Cys Ile Tyr Thr Phe Thr Ser Leu Phe Ser
    450                 455                 460

Leu Met Pro Asp Val Ala His Ser Leu Ala Val Glu Leu Cys Val Pro
465                 470                 475                 480

Gly Leu His Gly Trp Ala Thr Val Met Leu Leu Ser Thr Phe Cys Phe
```

-continued

```
                485                 490                 495
Gly Trp Val Leu Ile Pro Ala Val Thr Leu Ile Ile Leu Lys Cys Leu
                500                 505                 510
Arg Val Leu Thr Phe Ser Cys Ser His Tyr Thr Asn Glu Ser Lys Phe
                515                 520                 525
Lys Phe Ile Leu Glu Lys Val Lys Val Glu Tyr Gln Lys Thr Met Gly
                530                 535                 540
Ser Met Val Cys Asp Val Cys His His Glu Cys Glu Thr Ala Lys Glu
545                 550                 555                 560
Leu Glu Ser His Arg Gln Ser Cys Ile Asn Gly Gln Cys Pro Tyr Cys
                565                 570                 575
Met Thr Ile Thr Glu Ala Thr Glu Ser Ala Leu Gln Ala His Tyr Ser
                580                 585                 590
Ile Cys Lys Leu Thr Gly Arg Phe Gln Glu Ala Leu Lys Lys Ser Leu
                595                 600                 605
Lys Lys Pro Glu Val Lys Lys Gly Cys Tyr Arg Thr Leu Gly Val Phe
                610                 615                 620
Arg Tyr Lys Ser Arg Cys Tyr Val Gly Leu Val Trp Cys Leu Leu Leu
625                 630                 635                 640
Thr Cys Glu Ile Val Ile Trp Ala Ala Ser Ala Glu Thr Pro Leu Met
                645                 650                 655
Glu Ser Gly Trp Ser Asp Thr Ala His Gly Val Gly Glu Ile Pro Met
                660                 665                 670
Lys Thr Asp Leu Glu Leu Asp Phe Ser Leu Pro Ser Ser Ser Ser Tyr
                675                 680                 685
Ser Tyr Arg Arg Lys Leu Thr Asn Pro Ala Asn Lys Glu Glu Ser Ile
                690                 695                 700
Ser Phe His Phe Gln Met Glu Lys Gln Val Ile His Ala Glu Ile Gln
705                 710                 715                 720
Pro Leu Gly His Trp Met Asp Ala Thr Phe Asn Thr Lys Thr Ala Phe
                725                 730                 735
His Cys Tyr Gly Ala Cys Gln Lys Tyr Ser Tyr Cys Trp Gln Thr Ser
                740                 745                 750
Lys Cys Phe Phe Glu Lys Asp Tyr Gln Tyr Glu Thr Gly Trp Gly Cys
                755                 760                 765
Asn Pro Gly Asp Cys Pro Gly Val Gly Thr Gly Cys Thr Ala Cys Gly
                770                 775                 780
Val Tyr Leu Asp Lys Leu Lys Ser Val Gly Lys Ala Tyr Lys Ile Ile
785                 790                 795                 800
Ser Leu Lys Tyr Thr Arg Lys Val Cys Ile Gln Leu Gly Thr Glu Gln
                805                 810                 815
Thr Cys Lys His Ile Asp Ala Asn Asp Cys Leu Val Thr Pro Ser Val
                820                 825                 830
Lys Val Cys Ile Val Gly Thr Val Ser Lys Leu Gln Pro Ser Asp Thr
                835                 840                 845
Leu Leu Phe Leu Gly Pro Leu Glu Gln Gly Gly Val Ile Leu Lys Gln
                850                 855                 860
Trp Cys Thr Thr Ser Cys Ala Phe Gly Asp Pro Gly Asp Ile Met Ser
865                 870                 875                 880
Thr Pro Ser Gly Met Arg Cys Pro Glu His Thr Gly Ser Phe Arg Lys
                885                 890                 895
Ile Cys Gly Phe Ala Thr Thr Pro Val Cys Glu Tyr Gln Gly Asn Thr
                900                 905                 910
```

```
Ile Ser Gly Tyr Lys Arg Met Met Ala Thr Lys Asp Ser Phe Gln Ser
        915                 920                 925

Phe Asn Leu Thr Glu Pro His Ile Thr Ala Asn Lys Leu Glu Trp Ile
        930                 935                 940

Asp Pro Asp Gly Asn Thr Arg Asp His Val Asn Leu Val Leu Asn Arg
945                 950                 955                 960

Asp Val Ser Phe Gln Asp Leu Ser Asp Asn Pro Cys Lys Val Asp Leu
                965                 970                 975

His Thr Gln Ala Ile Glu Gly Ala Trp Gly Ser Gly Val Gly Phe Thr
            980                 985                 990

Leu Thr Cys Thr Val Gly Leu Thr Glu Cys Pro Ser Phe Met Thr Ser
        995                 1000                1005

Ile Lys Ala Cys Asp Leu Ala Met Cys Tyr Gly Ser Thr Val Ala
        1010                1015                1020

Asn Leu Ala Arg Gly Ser Asn Thr Val L

```
Thr Val Leu Cys Tyr Asp Leu Thr Cys Asn Gln Thr His Cys Gln Pro
130                 135                 140
Thr Val Tyr Leu Ile Ala Pro Val Leu Thr Cys Met Ser Ile Arg Ser
145                 150                 155                 160
Cys Met Ala Arg Val Phe Thr Ser Arg Ile Gln Val Ile Tyr Glu Lys
                165                 170                 175
Thr His Cys Val Thr Gly Gln Leu Ile Glu Gly Gln Cys Phe Asn Pro
                180                 185                 190
Ala His Thr Leu Thr Leu Ser Gln Pro Ala His Thr Tyr Asp Thr Val
        195                 200                 205
Thr Leu Pro Ile Ser Cys Phe Phe Thr Pro Lys Glu Ser Glu Gln Leu
210                 215                 220
Lys Val Ile Lys Thr Phe Glu Gly Ile Leu Thr Lys Thr Gly Cys Thr
225                 230                 235                 240
Glu Asn Ala Leu Gln Gly Tyr Tyr Val Cys Phe Leu Gly Ser His Ser
                245                 250                 255
Glu Pro Leu Ile Val Pro Ser Leu Glu Asp Ile Arg Ser Ala Glu Val
                260                 265                 270
Val Ser Arg Met Leu Val His Pro Arg Gly Glu Asp His Asp Ala Ile
        275                 280                 285
Gln Asn Ser Gln Ser His Leu Arg Ile Val Gly Pro Ile Thr Ala Lys
290                 295                 300
Val Pro Ser Thr Ser Ser Thr Asp Thr Leu Lys Gly Thr Ala Phe Ala
305                 310                 315                 320
Gly Val Pro Met Tyr Ser Ser Leu Ser Thr Leu Val Lys Asn Ala Asp
                325                 330                 335
Pro Glu Phe Val Phe Ser Pro Gly Ile Ile Pro Glu Ser Asn His Ser
                340                 345                 350
Val Cys Asp Lys Lys Thr Val Pro Ile Thr Trp Thr Gly Tyr Leu Pro
        355                 360                 365
Ile Ser Gly Glu Met Glu Lys Val Thr Gly Cys Thr Val Phe Cys Thr
370                 375                 380
Leu Ala Gly Pro Gly Ala Ser Cys Glu Ala Tyr Ser Glu Asn Gly Ile
385                 390                 395                 400
Phe Asn Ile Ser Ser Pro Thr Cys Leu Val Asn Lys Val Gln Arg Phe
                405                 410                 415
Arg Gly Ser Glu Gln Lys Ile Asn Phe Ile Cys Gln Arg Val Asp Gln
                420                 425                 430
Asp Val Val Val Tyr Cys Asn Gly Gln Lys Lys Val Ile Leu Thr Lys
        435                 440                 445
Thr Leu Val Ile Gly Gln Cys Ile Tyr Thr Phe Thr Ser Leu Phe Ser
450                 455                 460
Leu Met Pro Asp Val Ala His Ser Leu Ala Val Glu Leu Cys Val Pro
465                 470                 475                 480
Gly Leu His Gly Trp Ala Thr Val Met Leu Leu Ser Thr Phe Cys Phe
                485                 490                 495
Gly Trp Val Leu Ile Pro Ala Val Thr Leu Ile Ile Leu Lys Cys Leu
                500                 505                 510
Arg Val Leu Thr Phe Ser Cys Ser His Tyr Thr Asn Glu Ser Lys Phe
        515                 520                 525
Lys Phe Ile Leu Glu Lys Val Lys Val Glu Tyr Gln Lys Thr Met Gly
530                 535                 540
```

-continued

```
Ser Met Val Cys Asp Val Cys His His Glu Cys Glu Thr Ala Lys Glu
545                 550                 555                 560

Leu Glu Ser His Arg Gln Ser Cys Ile Asn Gly Gln Cys Pro Tyr Cys
            565                 570                 575

Met Thr Ile Thr Glu Ala Thr Glu Ser Ala Leu Gln Ala His Tyr Ser
        580                 585                 590

Ile Cys Lys Leu Thr Gly Arg Phe Gln Glu Ala Leu Lys Lys Ser Leu
    595                 600                 605

Lys Lys Pro Glu Val Lys Lys Gly Cys Tyr Arg Thr Leu Gly Val Phe
610                 615                 620

Arg Tyr Lys Ser Arg Cys Tyr Val Gly Leu Val Trp Cys Leu Leu Leu
625                 630                 635                 640

Thr Cys Glu Ile Val Ile Trp Ala Ala Ser Ala Glu Thr Pro Leu Met
            645                 650                 655

Glu Ser Gly Trp Ser Asp Thr Ala His Gly Val Gly Glu Ile Pro Met
                660                 665                 670

Lys Thr Asp Leu Glu Leu Asp Phe Ser Leu Pro Ser Ser Ser Ser Tyr
            675                 680                 685

Ser Tyr Arg Arg Lys Leu Thr Asn Pro Ala Asn Lys Glu Glu Ser Ile
    690                 695                 700

Ser Phe His Phe Gln Met Glu Lys Gln Val Ile His Ala Glu Ile Gln
705                 710                 715                 720

Pro Leu Gly His Trp Met Asp Ala Thr Phe Asn Thr Lys Thr Ala Phe
                725                 730                 735

His Cys Tyr Gly Ala Cys Gln Lys Tyr Ser Tyr Pro Trp Gln Thr Ser
            740                 745                 750

Lys Cys Phe Phe Glu Lys Asp Tyr Gln Tyr Glu Thr Gly Trp Gly Cys
        755                 760                 765

Asn Pro Gly Asp Cys Cys Gly Val Gly Thr Gly Cys Thr Ala Cys Gly
    770                 775                 780

Val Tyr Leu Asp Lys Leu Lys Ser Val Gly Lys Ala Tyr Lys Ile Ile
785                 790                 795                 800

Ser Leu Lys Tyr Thr Arg Lys Val Cys Ile Gln Leu Gly Thr Glu Gln
                805                 810                 815

Thr Cys Lys His Ile Asp Ala Asn Asp Cys Leu Val Thr Pro Ser Val
            820                 825                 830

Lys Val Cys Ile Val Gly Thr Val Ser Lys Leu Gln Pro Ser Asp Thr
        835                 840                 845

Leu Leu Phe Leu Gly Pro Leu Glu Gln Gly Val Ile Leu Lys Gln
850                 855                 860

Trp Cys Thr Thr Ser Cys Ala Phe Gly Asp Pro Gly Asp Ile Met Ser
865                 870                 875                 880

Thr Pro Ser Gly Met Arg Cys Pro Glu His Thr Gly Ser Phe Arg Lys
                885                 890                 895

Ile Cys Gly Phe Ala Thr Thr Pro Val Cys Glu Tyr Gln Gly Asn Thr
            900                 905                 910

Ile Ser Gly Tyr Lys Arg Met Met Ala Thr Lys Asp Ser Phe Gln Ser
        915                 920                 925

Phe Asn Leu Thr Glu Pro His Ile Thr Ala Asn Lys Leu Glu Trp Ile
    930                 935                 940

Asp Pro Asp Gly Asn Thr Arg Asp His Val Asn Leu Val Leu Asn Arg
945                 950                 955                 960

Asp Val Ser Phe Gln Asp Leu Ser Asp Asn Pro Cys Lys Val Asp Leu
```

His Thr Gln Ala Ile Glu Gly Ala Trp Gly Ser Gly Val Gly Phe Thr
                    980                 985                 990

Leu Thr Cys Thr Val Gly Leu Thr Glu Cys Pro Ser Phe Met Thr Ser
            995                 1000                1005

Ile Lys Ala Cys Asp Leu Ala Met Cys Tyr Gly Ser Thr Val Ala
    1010                1015                1020

Asn Leu Ala Arg Gly Ser Asn Thr Val Lys Val Val Gly Lys Gly
    1025                1030                1035

Gly His Ser Gly Ser Ser Phe Lys Cys Cys His Asp Thr Asp Cys
    1040                1045                1050

Ser Ser Glu Gly Leu Leu Ala Ser Ala Pro His Leu Glu Arg Val
    1055                1060                1065

Thr Gly Phe Asn Gln Ile Asp Ser Asp Lys Val Tyr Asp Asp Gly
    1070                1075                1080

Ala Pro Pro Cys Thr Phe Lys Cys Trp Phe Thr Lys Ser Gly Glu
    1085                1090                1095

Trp Leu Leu Gly Ile Leu Asn Gly Asn Trp Ile Val Val Val Val
    1100                1105                1110

Leu Val Val Ile Leu Ile Leu Ser Ile Ile Met Phe Ser Val Leu
    1115                1120                1125

Cys Pro Arg Arg Gly His Lys Lys Thr Val
    1130                1135

<210> SEQ ID NO 11
<211> LENGTH: 1138
<212> TYPE: PRT
<213> ORGANISM: Artificial Sequence
<220> FEATURE:
<223> OTHER INFORMATION: Synthetic: ANDV GPC N94C/V776C

<400> SEQUENCE: 11

Met Glu Gly Trp Tyr Leu Val Ala Leu Gly Ile Cys Tyr Thr Leu Thr
1               5                   10                  15

Leu Ala Met Pro Lys Thr Thr Tyr Glu Leu Lys Met Glu Cys Pro His
            20                  25                  30

Thr Val Gly Leu Gly Gln Gly Tyr Ile Ile Gly Ser Thr Glu Leu Gly
        35                  40                  45

Leu Ile Ser Ile Glu Ala Ala Ser Asp Ile Lys Leu Glu Ser Ser Cys
    50                  55                  60

Asn Phe Asp Leu His Thr Thr Ser Met Ala Gln Lys Ser Phe Thr Gln
65                  70                  75                  80

Val Glu Trp Arg Lys Lys Ser Asp Thr Thr Asp Thr Cys Ala Ala
                85                  90                  95

Ser Thr Thr Phe Glu Ala Gln Thr Lys Thr Val Asn Leu Arg Gly Thr
            100                 105                 110

Cys Ile Leu Ala Pro Glu Leu Tyr Asp Thr Leu Lys Lys Val Lys Lys
        115                 120                 125

Thr Val Leu Cys Tyr Asp Leu Thr Cys Asn Gln Thr His Cys Gln Pro
    130                 135                 140

Thr Val Tyr Leu Ile Ala Pro Val Leu Thr Cys Met Ser Ile Arg Ser
145                 150                 155                 160

Cys Met Ala Arg Val Phe Thr Ser Arg Ile Gln Val Ile Tyr Glu Lys
                165                 170                 175

Thr His Cys Val Thr Gly Gln Leu Ile Glu Gly Gln Cys Phe Asn Pro

```
            180             185             190
Ala His Thr Leu Thr Leu Ser Gln Pro Ala His Thr Tyr Asp Thr Val
            195             200             205
Thr Leu Pro Ile Ser Cys Phe Phe Thr Pro Lys Glu Ser Glu Gln Leu
    210             215             220
Lys Val Ile Lys Thr Phe Glu Gly Ile Leu Thr Lys Thr Gly Cys Thr
225             230             235             240
Glu Asn Ala Leu Gln Gly Tyr Tyr Val Cys Phe Leu Gly Ser His Ser
            245             250             255
Glu Pro Leu Ile Val Pro Ser Leu Glu Asp Ile Arg Ser Ala Glu Val
        260             265             270
Val Ser Arg Met Leu Val His Pro Arg Gly Glu Asp His Asp Ala Ile
        275             280             285
Gln Asn Ser Gln Ser His Leu Arg Ile Val Gly Pro Ile Thr Ala Lys
        290             295             300
Val Pro Ser Thr Ser Ser Thr Asp Thr Leu Lys Gly Thr Ala Phe Ala
305             310             315             320
Gly Val Pro Met Tyr Ser Ser Leu Ser Thr Leu Val Lys Asn Ala Asp
                325             330             335
Pro Glu Phe Val Phe Ser Pro Gly Ile Ile Pro Glu Ser Asn His Ser
                340             345             350
Val Cys Asp Lys Lys Thr Val Pro Ile Thr Trp Thr Gly Tyr Leu Pro
            355             360             365
Ile Ser Gly Glu Met Glu Lys Val Thr Gly Cys Thr Val Phe Cys Thr
        370             375             380
Leu Ala Gly Pro Gly Ala Ser Cys Glu Ala Tyr Ser Glu Asn Gly Ile
385             390             395             400
Phe Asn Ile Ser Ser Pro Thr Cys Leu Val Asn Lys Val Gln Arg Phe
                405             410             415
Arg Gly Ser Glu Gln Lys Ile Asn Phe Ile Cys Gln Arg Val Asp Gln
            420             425             430
Asp Val Val Val Tyr Cys Asn Gly Gln Lys Lys Val Ile Leu Thr Lys
                435             440             445
Thr Leu Val Ile Gly Gln Cys Ile Tyr Thr Phe Thr Ser Leu Phe Ser
        450             455             460
Leu Met Pro Asp Val Ala His Ser Leu Ala Val Glu Leu Cys Val Pro
465             470             475             480
Gly Leu His Gly Trp Ala Thr Val Met Leu Leu Ser Thr Phe Cys Phe
                485             490             495
Gly Trp Val Leu Ile Pro Ala Val Thr Leu Ile Ile Leu Lys Cys Leu
            500             505             510
Arg Val Leu Thr Phe Ser Cys Ser His Tyr Thr Asn Glu Ser Lys Phe
        515             520             525
Lys Phe Ile Leu Glu Lys Val Lys Val Glu Tyr Gln Lys Thr Met Gly
        530             535             540
Ser Met Val Cys Asp Val Cys His His Glu Cys Glu Thr Ala Lys Glu
545             550             555             560
Leu Glu Ser His Arg Gln Ser Cys Ile Asn Gly Gln Cys Pro Tyr Cys
                565             570             575
Met Thr Ile Thr Glu Ala Thr Glu Ser Ala Leu Gln Ala His Tyr Ser
            580             585             590
Ile Cys Lys Leu Thr Gly Arg Phe Gln Glu Ala Leu Lys Lys Ser Leu
        595             600             605
```

-continued

Lys Lys Pro Glu Val Lys Lys Gly Cys Tyr Arg Thr Leu Gly Val Phe
610             615                 620

Arg Tyr Lys Ser Arg Cys Tyr Val Gly Leu Val Trp Cys Leu Leu Leu
625             630                 635                 640

Thr Cys Glu Ile Val Ile Trp Ala Ala Ser Ala Glu Thr Pro Leu Met
            645                 650                 655

Glu Ser Gly Trp Ser Asp Thr Ala His Gly Val Gly Glu Ile Pro Met
            660                 665                 670

Lys Thr Asp Leu Glu Leu Asp Phe Ser Leu Pro Ser Ser Ser Ser Tyr
            675                 680                 685

Ser Tyr Arg Arg Lys Leu Thr Asn Pro Ala Asn Lys Glu Glu Ser Ile
690                 695                 700

Ser Phe His Phe Gln Met Glu Lys Gln Val Ile His Ala Glu Ile Gln
705             710                 715                 720

Pro Leu Gly His Trp Met Asp Ala Thr Phe Asn Thr Lys Thr Ala Phe
                725                 730                 735

His Cys Tyr Gly Ala Cys Gln Lys Tyr Ser Tyr Pro Trp Gln Thr Ser
                740                 745                 750

Lys Cys Phe Phe Glu Lys Asp Tyr Gln Tyr Glu Thr Gly Trp Gly Cys
            755                 760                 765

Asn Pro Gly Asp Cys Pro Gly Cys Gly Thr Gly Cys Thr Ala Cys Gly
770                 775                 780

Val Tyr Leu Asp Lys Leu Lys Ser Val Gly Lys Ala Tyr Lys Ile Ile
785                 790                 795                 800

Ser Leu Lys Tyr Thr Arg Lys Val Cys Ile Gln Leu Gly Thr Glu Gln
                805                 810                 815

Thr Cys Lys His Ile Asp Ala Asn Asp Cys Leu Val Thr Pro Ser Val
                820                 825                 830

Lys Val Cys Ile Val Gly Thr Val Ser Lys Leu Gln Pro Ser Asp Thr
            835                 840                 845

Leu Leu Phe Leu Gly Pro Leu Glu Gln Gly Gly Val Ile Leu Lys Gln
            850                 855                 860

Trp Cys Thr Thr Ser Cys Ala Phe Gly Asp Pro Gly Asp Ile Met Ser
865                 870                 875                 880

Thr Pro Ser Gly Met Arg Cys Pro Glu His Thr Gly Ser Phe Arg Lys
                885                 890                 895

Ile Cys Gly Phe Ala Thr Thr Pro Val Cys Glu Tyr Gln Gly Asn Thr
                900                 905                 910

Ile Ser Gly Tyr Lys Arg Met Met Ala Thr Lys Asp Ser Phe Gln Ser
            915                 920                 925

Phe Asn Leu Thr Glu Pro His Ile Thr Ala Asn Lys Leu Glu Trp Ile
            930                 935                 940

Asp Pro Asp Gly Asn Thr Arg Asp His Val Asn Leu Val Leu Asn Arg
945                 950                 955                 960

Asp Val Ser Phe Gln Asp Leu Ser Asp Asn Pro Cys Lys Val Asp Leu
                965                 970                 975

His Thr Gln Ala Ile Glu Gly Ala Trp Gly Ser Gly Val Gly Phe Thr
            980                 985                 990

Leu Thr Cys Thr Val Gly Leu Thr Glu Cys Pro Ser Phe Met Thr Ser
            995                 1000                1005

Ile Lys Ala Cys Asp Leu Ala Met Cys Tyr Gly Ser Thr Val Ala
    1010                1015                1020

-continued

Asn Leu Ala Arg Gly Ser Asn Thr Val Lys Val Val Gly Lys Gly
    1025                1030                1035

Gly His Ser Gly Ser Ser Phe Lys Cys Cys His Asp Thr Asp Cys
    1040                1045                1050

Ser Ser Glu Gly Leu Leu Ala Ser Ala Pro His Leu Glu Arg Val
    1055                1060                1065

Thr Gly Phe Asn Gln Ile Asp Ser Asp Lys Val Tyr Asp Asp Gly
    1070                1075                1080

Ala Pro Pro Cys Thr Phe Lys Cys Trp Phe Thr Lys Ser Gly Glu
    1085                1090                1095

Trp Leu Leu Gly Ile Leu Asn Gly Asn Trp Ile Val Val Val Val
    1100                1105                1110

Leu Val Val Ile Leu Ile Leu Ser Ile Ile Met Phe Ser Val Leu
    1115                1120                1125

Cys Pro Arg Arg Gly His Lys Lys Thr Val
    1130                1135

<210> SEQ ID NO 12
<211> LENGTH: 1138
<212> TYPE: PRT
<213> ORGANISM: Artificial Sequence
<220> FEATURE:
<223> OTHER INFORMATION: Synthetic: ANDV GPC E61C/Q200C

<400> SEQUENCE: 12

Met Glu Gly Trp Tyr Leu Val Ala Leu Gly Ile Cys Tyr Thr Leu Thr
1               5                   10                  15

Leu Ala Met Pro Lys Thr Thr Tyr Glu Leu Lys Met Glu Cys Pro His
                20                  25                  30

Thr Val Gly Leu Gly Gln Gly Tyr Ile Ile Gly Ser Thr Glu Leu Gly
            35                  40                  45

Leu Ile Ser Ile Glu Ala Ala Ser Asp Ile Lys Leu Cys Ser Ser Cys
        50                  55                  60

Asn Phe Asp Leu His Thr Thr Ser Met Ala Gln Lys Ser Phe Thr Gln
65                  70                  75                  80

Val Glu Trp Arg Lys Lys Ser Asp Thr Thr Asp Thr Asn Ala Ala
                85                  90                  95

Ser Thr Thr Phe Glu Ala Gln Thr Lys Thr Val Asn Leu Arg Gly Thr
                100                 105                 110

Cys Ile Leu Ala Pro Glu Leu Tyr Asp Thr Leu Lys Lys Val Lys Lys
            115                 120                 125

Thr Val Leu Cys Tyr Asp Leu Thr Cys Asn Gln Thr His Cys Gln Pro
    130                 135                 140

Thr Val Tyr Leu Ile Ala Pro Val Leu Thr Cys Met Ser Ile Arg Ser
145                 150                 155                 160

Cys Met Ala Arg Val Phe Thr Ser Arg Ile Gln Val Ile Tyr Glu Lys
                165                 170                 175

Thr His Cys Val Thr Gly Gln Leu Ile Glu Gly Gln Cys Phe Asn Pro
            180                 185                 190

Ala His Thr Leu Thr Leu Ser Cys Pro Ala His Thr Tyr Asp Thr Val
        195                 200                 205

Thr Leu Pro Ile Ser Cys Phe Phe Thr Pro Lys Glu Ser Glu Gln Leu
    210                 215                 220

Lys Val Ile Lys Thr Phe Glu Gly Ile Leu Thr Lys Thr Gly Cys Thr
225                 230                 235                 240

-continued

```
Glu Asn Ala Leu Gln Gly Tyr Tyr Val Cys Phe Leu Gly Ser His Ser
                245                 250                 255

Glu Pro Leu Ile Val Pro Ser Leu Glu Asp Ile Arg Ser Ala Glu Val
            260                 265                 270

Val Ser Arg Met Leu Val His Pro Arg Gly Glu Asp His Asp Ala Ile
        275                 280                 285

Gln Asn Ser Gln Ser His Leu Arg Ile Val Gly Pro Ile Thr Ala Lys
    290                 295                 300

Val Pro Ser Thr Ser Ser Thr Asp Thr Leu Lys Gly Thr Ala Phe Ala
305                 310                 315                 320

Gly Val Pro Met Tyr Ser Ser Leu Ser Thr Leu Val Lys Asn Ala Asp
                325                 330                 335

Pro Glu Phe Val Phe Ser Pro Gly Ile Ile Pro Glu Ser Asn His Ser
            340                 345                 350

Val Cys Asp Lys Lys Thr Val Pro Ile Thr Trp Thr Gly Tyr Leu Pro
        355                 360                 365

Ile Ser Gly Glu Met Glu Lys Val Thr Gly Cys Thr Val Phe Cys Thr
    370                 375                 380

Leu Ala Gly Pro Gly Ala Ser Cys Glu Ala Tyr Ser Glu Asn Gly Ile
385                 390                 395                 400

Phe Asn Ile Ser Ser Pro Thr Cys Leu Val Asn Lys Val Gln Arg Phe
                405                 410                 415

Arg Gly Ser Glu Gln Lys Ile Asn Phe Ile Cys Gln Arg Val Asp Gln
            420                 425                 430

Asp Val Val Val Tyr Cys Asn Gly Gln Lys Lys Val Ile Leu Thr Lys
        435                 440                 445

Thr Leu Val Ile Gly Gln Cys Ile Tyr Thr Phe Thr Ser Leu Phe Ser
    450                 455                 460

Leu Met Pro Asp Val Ala His Ser Leu Ala Val Glu Leu Cys Val Pro
465                 470                 475                 480

Gly Leu His Gly Trp Ala Thr Val Met Leu Leu Ser Thr Phe Cys Phe
                485                 490                 495

Gly Trp Val Leu Ile Pro Ala Val Thr Leu Ile Ile Leu Lys Cys Leu
            500                 505                 510

Arg Val Leu Thr Phe Ser Cys Ser His Tyr Thr Asn Glu Ser Lys Phe
        515                 520                 525

Lys Phe Ile Leu Glu Lys Val Lys Val Glu Tyr Gln Lys Thr Met Gly
    530                 535                 540

Ser Met Val Cys Asp Val Cys His His Glu Cys Glu Thr Ala Lys Glu
545                 550                 555                 560

Leu Glu Ser His Arg Gln Ser Cys Ile Asn Gly Gln Cys Pro Tyr Cys
                565                 570                 575

Met Thr Ile Thr Glu Ala Thr Glu Ser Ala Leu Gln Ala His Tyr Ser
            580                 585                 590

Ile Cys Lys Leu Thr Gly Arg Phe Gln Glu Ala Leu Lys Lys Ser Leu
        595                 600                 605

Lys Lys Pro Glu Val Lys Lys Gly Cys Tyr Arg Thr Leu Gly Val Phe
    610                 615                 620

Arg Tyr Lys Ser Arg Cys Tyr Val Gly Leu Val Trp Cys Leu Leu Leu
625                 630                 635                 640

Thr Cys Glu Ile Val Ile Trp Ala Ala Ser Ala Glu Thr Pro Leu Met
                645                 650                 655

Glu Ser Gly Trp Ser Asp Thr Ala His Gly Val Gly Glu Ile Pro Met
```

```
                  660               665               670
Lys Thr Asp Leu Glu Leu Asp Phe Ser Leu Pro Ser Ser Ser Ser Tyr
                675               680               685

Ser Tyr Arg Arg Lys Leu Thr Asn Pro Ala Asn Lys Glu Glu Ser Ile
                690               695               700

Ser Phe His Phe Gln Met Glu Lys Gln Val Ile His Ala Glu Ile Gln
705               710               715               720

Pro Leu Gly His Trp Met Asp Ala Thr Phe Asn Thr Lys Thr Ala Phe
                725               730               735

His Cys Tyr Gly Ala Cys Gln Lys Tyr Ser Tyr Pro Trp Gln Thr Ser
                740               745               750

Lys Cys Phe Phe Glu Lys Asp Tyr Gln Tyr Glu Thr Gly Trp Gly Cys
                755               760               765

Asn Pro Gly Asp Cys Pro Gly Val Gly Thr Gly Cys Thr Ala Cys Gly
                770               775               780

Val Tyr Leu Asp Lys Leu Lys Ser Val Gly Lys Ala Tyr Lys Ile Ile
785               790               795               800

Ser Leu Lys Tyr Thr Arg Lys Val Cys Ile Gln Leu Gly Thr Glu Gln
                805               810               815

Thr Cys Lys His Ile Asp Ala Asn Asp Cys Leu Val Thr Pro Ser Val
                820               825               830

Lys Val Cys Ile Val Gly Thr Val Ser Lys Leu Gln Pro Ser Asp Thr
835               840               845

Leu Leu Phe Leu Gly Pro Leu Glu Gln Gly Gly Val Ile Leu Lys Gln
                850               855               860

Trp Cys Thr Thr Ser Cys Ala Phe Gly Asp Pro Gly Asp Ile Met Ser
865               870               875               880

Thr Pro Ser Gly Met Arg Cys Pro Glu His Thr Gly Ser Phe Arg Lys
                885               890               895

Ile Cys Gly Phe Ala Thr Thr Pro Val Cys Glu Tyr Gln Gly Asn Thr
                900               905               910

Ile Ser Gly Tyr Lys Arg Met Met Ala Thr Lys Asp Ser Phe Gln Ser
                915               920               925

Phe Asn Leu Thr Glu Pro His Ile Thr Ala Asn Lys Leu Glu Trp Ile
930               935               940

Asp Pro Asp Gly Asn Thr Arg Asp His Val Asn Leu Val Leu Asn Arg
945               950               955               960

Asp Val Ser Phe Gln Asp Leu Ser Asp Asn Pro Cys Lys Val Asp Leu
                965               970               975

His Thr Gln Ala Ile Glu Gly Ala Trp Gly Ser Gly Val Gly Phe Thr
                980               985               990

Leu Thr Cys Thr Val Gly Leu Thr Glu Cys Pro Ser Phe Met Thr Ser
                995               1000              1005

Ile Lys Ala Cys Asp Leu Ala Met Cys Tyr Gly Ser Thr Val Ala
                1010              1015              1020

Asn Leu Ala Arg Gly Ser Asn Thr Val Lys Val Val Gly Lys Gly
                1025              1030              1035

Gly His Ser Gly Ser Ser Phe Lys Cys Cys His Asp Thr Asp Cys
                1040              1045              1050

Ser Ser Glu Gly Leu Leu Ala Ser Ala Pro His Leu Glu Arg Val
                1055              1060              1065

Thr Gly Phe Asn Gln Ile Asp Ser Asp Lys Val Tyr Asp Asp Gly
                1070              1075              1080
```

-continued

```
Ala Pro Pro Cys Thr Phe Lys Cys Trp Phe Thr Lys Ser Gly Glu
    1085                1090                1095

Trp Leu Leu Gly Ile Leu Asn Gly Asn Trp Ile Val Val Val Val
    1100                1105                1110

Leu Val Val Ile Leu Ile Leu Ser Ile Ile Met Phe Ser Val Leu
    1115                1120                1125

Cys Pro Arg Arg Gly His Lys Lys Thr Val
    1130                1135

<210> SEQ ID NO 13
<211> LENGTH: 1140
<212> TYPE: PRT
<213> ORGANISM: Sin Nombre orthohantavirus
<220> FEATURE:
<221> NAME/KEY: misc_feature
<222> LOCATION: (1)..(1140)
<223> OTHER INFORMATION: Sin_Nombre_Orthohantavirus_GPC AAA75530.1

<400> SEQUENCE: 13

Met Val Gly Trp Val Cys Ile Phe Leu Val Val Leu Thr Thr Ala Thr
1               5                   10                  15

Ala Gly Leu Thr Arg Asn Leu Tyr Glu Leu Lys Ile Glu Cys Pro His
            20                  25                  30

Thr Val Gly Leu Gly Gln Gly Tyr Val Thr Gly Ser Val Glu Ile Thr
        35                  40                  45

Pro Ile Leu Leu Thr Gln Val Ala Asp Leu Lys Ile Glu Ser Ser Cys
    50                  55                  60

Asn Phe Asp Leu His Val Pro Ala Thr Thr Thr Gln Lys Tyr Asn Gln
65                  70                  75                  80

Val Asp Trp Thr Lys Lys Ser Ser Thr Thr Glu Ser Thr Asn Ala Gly
                85                  90                  95

Ala Thr Thr Phe Glu Ala Lys Thr Lys Glu Ile Asn Leu Lys Gly Thr
            100                 105                 110

Cys Asn Ile Pro Pro Thr Thr Phe Glu Ala Ala Tyr Lys Ser Arg Lys
        115                 120                 125

Thr Val Ile Cys Tyr Asp Leu Ala Cys Asn Gln Thr His Cys Leu Pro
    130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Ile Glu Gly Leu Cys Phe Ile Pro
            180                 185                 190

Thr His Thr Ile Ala Leu Thr Gln Pro Gly His Thr Tyr Asp Thr Met
        195                 200                 205

Thr Leu Pro Val Thr Cys Phe Leu Val Ala Lys Lys Leu Gly Thr Gln
    210                 215                 220

Leu Lys Leu Ala Val Glu Leu Glu Lys Leu Ile Thr Gly Val Ser Cys
225                 230                 235                 240

Thr Glu Asn Ser Phe Gln Gly Tyr Tyr Ile Cys Phe Ile Gly Lys His
                245                 250                 255

Ser Glu Pro Leu Phe Val Pro Thr Met Glu Asp Tyr Arg Ser Ala Glu
            260                 265                 270

Leu Phe Thr Arg Met Val Leu Asn Pro Arg Gly Glu Asp His Asp Pro
        275                 280                 285
```

```
Asp Gln Asn Gly Gln Gly Leu Met Arg Ile Ala Gly Pro Val Thr Ala
    290                 295                 300
Lys Val Pro Ser Thr Glu Thr Thr Glu Thr Met Gln Gly Ile Ala Phe
305                 310                 315                 320
Ala Gly Ala Pro Met Tyr Ser Ser Phe Ser Thr Leu Val Arg Lys Ala
                325                 330                 335
Asp Pro Glu Tyr Val Phe Ser Pro Gly Ile Ile Ala Glu Ser Asn His
            340                 345                 350
Ser Val Cys Asp Lys Lys Thr Val Pro Leu Thr Trp Thr Gly Phe Leu
        355                 360                 365
Ala Val Ser Gly Glu Ile Glu Lys Ile Thr Gly Cys Thr Val Phe Cys
    370                 375                 380
Thr Leu Ala Gly Pro Gly Ala Ser Cys Glu Ala Tyr Ser Glu Thr Gly
385                 390                 395                 400
Ile Phe Asn Ile Ser Ser Pro Thr Cys Leu Val Asn Lys Val Gln Lys
                405                 410                 415
Phe Arg Gly Ser Glu Gln Arg Ile Asn Phe Met Cys Gln Arg Val Asp
            420                 425                 430
Gln Asp Val Val Tyr Cys Asn Gly Gln Lys Lys Val Ile Leu Thr
        435                 440                 445
Lys Thr Leu Val Ile Gly Gln Cys Ile Tyr Thr Phe Thr Ser Leu Phe
    450                 455                 460
Ser Leu Ile Pro Gly Val Ala His Ser Leu Ala Val Glu Leu Cys Val
465                 470                 475                 480
Pro Gly Leu His Gly Trp Ala Thr Thr Ala Leu Leu Ile Thr Phe Cys
                485                 490                 495
Phe Gly Trp Leu Leu Ile Pro Ala Val Thr Leu Ile Ile Leu Lys Ile
            500                 505                 510
Leu Arg Leu Leu Thr Phe Ser Cys Ser His Tyr Ser Thr Glu Ser Lys
        515                 520                 525
Phe Lys Val Ile Leu Glu Arg Val Lys Val Glu Tyr Gln Lys Thr Met
    530                 535                 540
Gly Ser Met Val Cys Asp Ile Cys His His Glu Cys Glu Thr Ala Lys
545                 550                 555                 560
Glu Leu Glu Thr His Lys Lys Ser Cys Pro Glu Gly Gln Cys Pro Tyr
                565                 570                 575
Cys Met Thr Ile Thr Glu Ser Thr Glu Ser Ala Leu Gln Ala His Phe
            580                 585                 590
Ala Ile Cys Lys Leu Thr Asn Arg Phe Gln Glu Asn Leu Lys Lys Ser
        595                 600                 605
Leu Lys Arg Pro Glu Val Arg Lys Gly Cys Tyr Arg Thr Leu Gly Val
    610                 615                 620
Phe Arg Tyr Lys Ser Arg Cys Tyr Val Gly Leu Val Trp Gly Ile Leu
625                 630                 635                 640
Leu Thr Thr Glu Leu Ile Ile Trp Ala Ala Ser Ala Asp Thr Pro Leu
                645                 650                 655
Met Glu Ser Gly Trp Ser Asp Thr Ala His Gly Val Gly Ile Ile Pro
            660                 665                 670
Met Lys Thr Asp Leu Glu Leu Asp Phe Ala Leu Ala Ser Ser Ser
        675                 680                 685
Tyr Ser Tyr Arg Arg Lys Leu Val Asn Pro Ala Asn Gln Glu Glu Thr
    690                 695                 700
Leu Pro Phe His Phe Gln Leu Asp Lys Gln Val Val His Ala Glu Ile
```

```
            705                 710                 715                 720
        Gln Asn Leu Gly His Trp Met Asp Gly Thr Phe Asn Ile Lys Thr Ala
                        725                 730                 735
        Phe His Cys Tyr Gly Glu Cys Lys Lys Tyr Ala Tyr Pro Trp Gln Thr
                        740                 745                 750
        Ala Lys Cys Phe Phe Glu Lys Asp Tyr Gln Tyr Glu Thr Ser Trp Gly
                        755                 760                 765
        Cys Asn Pro Pro Asp Cys Pro Gly Val Gly Thr Gly Cys Thr Ala Cys
                        770                 775                 780
        Gly Val Tyr Leu Asp Lys Leu Arg Ser Val Gly Lys Ala Tyr Lys Ile
        785                 790                 795                 800
        Val Ser Leu Lys Tyr Thr Arg Lys Val Cys Ile Gln Leu Gly Thr Glu
                        805                 810                 815
        Gln Thr Cys Lys His Ile Asp Val Asn Asp Cys Leu Val Thr Pro Ser
                        820                 825                 830
        Val Lys Val Cys Met Ile Gly Thr Ile Ser Lys Leu Gln Pro Gly Asp
                        835                 840                 845
        Thr Leu Leu Phe Leu Gly Pro Leu Glu Gln Gly Gly Ile Ile Leu Lys
                        850                 855                 860
        Gln Trp Cys Thr Thr Ser Cys Val Phe Gly Asp Pro Gly Asp Ile Met
        865                 870                 875                 880
        Ser Thr Thr Ser Gly Met Arg Cys Pro Glu His Thr Gly Ser Phe Arg
                        885                 890                 895
        Lys Ile Cys Gly Phe Ala Thr Thr Pro Thr Cys Glu Tyr Gln Gly Asn
                        900                 905                 910
        Thr Val Ser Gly Phe Gln Arg Met Met Ala Thr Arg Asp Ser Phe Gln
                        915                 920                 925
        Ser Phe Asn Val Thr Glu Pro His Ile Thr Ser Asn Arg Leu Glu Trp
                        930                 935                 940
        Ile Asp Pro Asp Ser Ser Ile Lys Asp His Ile Asn Met Val Leu Asn
        945                 950                 955                 960
        Arg Asp Val Ser Phe Gln Asp Leu Ser Asp Asn Pro Cys Lys Val Asp
                        965                 970                 975
        Leu His Thr Gln Ser Ile Asp Gly Ala Trp Gly Ser Gly Val Gly Phe
                        980                 985                 990
        Thr Leu Val Cys Thr Val Gly Leu Thr Glu Cys Ala Asn Phe Ile Thr
                        995                 1000                1005
        Ser Ile Lys Ala Cys Asp Ser Ala Met Cys Tyr Gly Ala Thr Val
                1010                1015                1020
        Thr Asn Leu Leu Arg Gly Ser Asn Thr Val Lys Val Val Gly Lys
                1025                1030                1035
        Gly Gly His Ser Gly Ser Leu Phe Lys Cys Cys His Asp Thr Asp
                1040                1045                1050
        Cys Thr Glu Glu Gly Leu Ala Ala Ser Pro Pro His Leu Asp Arg
                1055                1060                1065
        Val Thr Gly Tyr Asn Gln Ile Asp Ser Asp Lys Val Tyr Asp Asp
                1070                1075                1080
        Gly Ala Pro Pro Cys Thr Ile Lys Cys Trp Phe Thr Lys Ser Gly
                1085                1090                1095
        Glu Trp Leu Leu Gly Ile Leu Asn Gly Asn Trp Val Val Val Ala
                1100                1105                1110
        Val Leu Ile Val Ile Leu Ile Leu Ser Ile Leu Leu Phe Ser Phe
                1115                1120                1125
```

```
Phe Cys Pro Val Arg Ser Lys Asn Lys Ala Asn
        1130            1135            1140

<210> SEQ ID NO 14
<211> LENGTH: 1148
<212> TYPE: PRT
<213> ORGANISM: Puumala orthohantavirus
<220> FEATURE:
<221> NAME/KEY: misc_feature
<222> LOCATION: (1)..(1148)
<223> OTHER INFORMATION: Puumala_Orthohantavirus_GPC NP_941983.1

<400> SEQUENCE: 14

Met Gly Lys Ser Ser Pro Val Cys Leu Tyr Leu Ile Leu Gln Gly Leu
1               5                   10                  15

Leu Leu Phe Asp Thr Val Asn Ala Lys Asn Leu Asn Glu Leu Lys Met
            20                  25                  30

Glu Cys Pro His Thr Ile Gly Leu Gly Gln Gly Leu Val Val Gly Ser
        35                  40                  45

Val Glu Leu Pro Pro Val Pro Ile Gln Gln Ile Glu Ser Leu Lys Leu
    50                  55                  60

Glu Ser Ser Cys Asn Phe Asp Leu His Thr Ser Thr Ala Gly Gln Gln
65                  70                  75                  80

Ser Phe Thr Lys Trp Thr Trp Glu Thr Lys Gly Asp Leu Ala Glu Asn
                85                  90                  95

Thr Gln Ala Ser Ser Thr Ser Phe Gln Thr Lys Ser Ser Glu Val Asn
            100                 105                 110

Leu Arg Gly Leu Cys Leu Ile Pro Thr Leu Val Val Glu Thr Ala Ala
        115                 120                 125

Arg Met Arg Lys Thr Ile Ala Cys Tyr Asp Leu Ser Cys Asn Gln Thr
130                 135                 140

Val Cys Gln Pro Thr Val Tyr Leu Met Gly Pro Ile Gln Thr Cys Leu
145                 150                 155                 160

Thr Thr Lys Ser Cys Leu Leu Gly Leu Gly Asp Gln Arg Ile Gln Val
                165                 170                 175

Asn Tyr Glu Arg Thr Tyr Cys Val Ser Gly Gln Leu Val Glu Gly Val
            180                 185                 190

Cys Phe Asn Pro Ile His Thr Met Ala Leu Ser Gln Pro Ser His Thr
        195                 200                 205

Tyr Asp Ile Val Thr Ile Met Val Arg Cys Phe Leu Val Ile Lys Lys
    210                 215                 220

Val Thr Ser Gly Asp Ser Met Lys Ile Glu Lys Asn Phe Glu Thr Leu
225                 230                 235                 240

Val Gln Lys Thr Gly Cys Thr Ala Asn Gly Phe Gln Gly Tyr Tyr Ile
                245                 250                 255

Cys Leu Ile Gly Ser Ser Ser Glu Pro Leu Tyr Val Pro Thr Leu Asp
            260                 265                 270

Asp Tyr Arg Ser Ala Glu Val Leu Ser Arg Met Ala Phe Ala Pro His
        275                 280                 285

Gly Glu Asp His Asp Ile Glu Lys Asn Ala Val Ser Ala Leu Arg Ile
    290                 295                 300

Ala Gly Lys Val Thr Gly Lys Ala Pro Ser Thr Glu Ser Ser Asp Thr
305                 310                 315                 320

Val Gln Gly Ile Ala Phe Ser Gly Ser Pro Leu Tyr Thr Ser Thr Gly
                325                 330                 335
```

```
Val Leu Thr Ala Lys Asp Asp Pro Val Tyr Val Trp Ala Pro Gly Ile
            340                 345                 350

Ile Met Glu Gly Asn His Ser Val Cys Glu Lys Lys Thr Leu Pro Leu
            355                 360                 365

Thr Trp Thr Gly Phe Ile Pro Leu Pro Gly Glu Ile Glu Lys Thr Thr
            370                 375                 380

Gln Cys Thr Val Phe Cys Thr Leu Ala Gly Pro Gly Ala Asp Cys Glu
385                 390                 395                 400

Ala Tyr Ser Glu Thr Gly Ile Phe Asn Ile Ser Ser Pro Thr Cys Leu
            405                 410                 415

Ile Asn Arg Val Gln Arg Phe Arg Gly Ala Glu Gln Gln Ile Lys Phe
            420                 425                 430

Val Cys Gln Arg Val Asp Met Asp Ile Thr Val Tyr Cys Asn Gly Val
            435                 440                 445

Lys Lys Val Ile Leu Thr Lys Thr Leu Val Ile Gly Gln Cys Ile Tyr
            450                 455                 460

Thr Phe Thr Ser Ile Phe Ser Met Ile Pro Gly Ile Ala His Ser Leu
465                 470                 475                 480

Ala Val Glu Leu Cys Val Pro Gly Leu His Gly Trp Ala Thr Val Leu
            485                 490                 495

Leu Leu Leu Thr Phe Cys Phe Gly Trp Val Leu Ile Pro Thr Ile Thr
            500                 505                 510

Met Ile Leu Leu Lys Ile Leu Ile Ala Phe Ala Tyr Leu Cys Ser Lys
            515                 520                 525

Tyr Asn Thr Asp Ser Lys Phe Arg Ile Leu Val Glu Lys Val Lys Lys
            530                 535                 540

Glu Tyr Gln Lys Thr Met Gly Ser Met Val Cys Glu Val Cys Gln Tyr
545                 550                 555                 560

Glu Cys Glu Thr Ala Lys Glu Leu Glu Ser His Arg Lys Ser Cys Ser
            565                 570                 575

Ile Gly Ser Cys Pro Tyr Cys Leu Asn Pro Ser Glu Ala Thr Pro Ser
            580                 585                 590

Ala Leu Gln Ala His Phe Lys Val Cys Lys Leu Thr Ser Arg Phe Gln
            595                 600                 605

Glu Asn Leu Lys Lys Ser Leu Thr Met Tyr Glu Pro Met Gln Gly Cys
            610                 615                 620

Tyr Arg Thr Leu Ser Leu Phe Arg Tyr Arg Ser Arg Phe Phe Val Gly
625                 630                 635                 640

Leu Val Trp Cys Met Leu Leu Val Leu Glu Leu Ile Val Trp Ala Ala
            645                 650                 655

Ser Ala Glu Thr Gln Asn Leu Asn Asp Gly Trp Thr Asp Thr Ala His
            660                 665                 670

Gly Ser Gly Ile Ile Pro Met Lys Ala Asp Leu Glu Leu Asp Phe Ser
            675                 680                 685

Leu Pro Ser Ser Ala Ser Tyr Thr Tyr Arg Arg Gln Leu Gln Asn Pro
            690                 695                 700

Ala Asn Glu Gln Glu Lys Ile Pro Phe His Leu Gln Ile Ser Lys Gln
705                 710                 715                 720

Val Ile His Ala Glu Ile Gln His Leu Gly His Trp Met Asp Ala Thr
            725                 730                 735

Phe Asn Leu Lys Thr Ala Phe His Cys Tyr Gly Ser Cys Glu Lys Tyr
            740                 745                 750

Ala Tyr Pro Trp Gln Thr Ala Gly Cys Phe Val Glu Lys Asp Tyr Glu
```

```
                755              760              765
Tyr Glu Thr Gly Trp Gly Cys Asn Pro Pro Asp Cys Pro Gly Val Gly
770              775              780

Thr Gly Cys Thr Ala Cys Gly Val Tyr Leu Asp Lys Leu Lys Ser Val
785              790              795              800

Gly Lys Val Phe Lys Ile Val Ser Leu Arg Tyr Thr Arg Lys Val Cys
                805              810              815

Ile Gln Leu Gly Thr Gly Gln Thr Cys Lys Thr Val Asp Ser Asn Asp
                820              825              830

Cys Leu Ile Thr Thr Ser Val Lys Val Cys Leu Ile Gly Thr Ile Ser
                835              840              845

Lys Phe Gln Pro Ser Asp Thr Leu Leu Phe Leu Gly Pro Leu Gln Gln
850              855              860

Gly Gly Leu Ile Phe Lys Gln Trp Cys Thr Thr Thr Cys Gln Phe Gly
865              870              875              880

Asp Pro Gly Asp Ile Met Ser Thr Pro Thr Gly Met Lys Cys Pro Glu
                885              890              895

Leu Asn Gly Ser Phe Arg Lys Lys Cys Ala Phe Ala Thr Thr Pro Val
                900              905              910

Cys Gln Phe Asp Gly Asn Thr Ile Ser Gly Tyr Lys Arg Met Val Ala
                915              920              925

Thr Lys Asp Ser Phe Gln Ser Phe Asn Val Thr Glu Pro His Ile Ser
930              935              940

Thr Ser Ala Leu Glu Trp Ile Asp Leu Asp Ser Ser Leu Arg Asp His
945              950              955              960

Ile Asn Val Ile Val Ser Arg Asp Leu Ser Phe Gln Asp Leu Ser Glu
                965              970              975

Thr Pro Cys Gln Val Asp Leu Thr Thr Ser Ala Thr Asp Gly Ala Trp
                980              985              990

Gly Ser Gly Val Gly Phe Asn Leu Val Cys Thr Val Ser Leu Thr Glu
                995              1000             1005

Cys Ser Ala Phe Leu Thr Ser Ile Lys Ala Cys His Ala Ala Met
                1010             1015             1020

Cys Tyr Gly Ser Thr Thr Thr Asn Leu Val Arg Gly Gln Asn Thr
1025             1030             1035

Ile His Val Val Gly Lys Gly His Ser Gly Ser Lys Phe Met
1040             1045             1050

Cys Cys His Asp Thr Lys Cys Ser Ser Thr Gly Leu Val Ala Ala
1055             1060             1065

Ala Pro His Leu Asp Arg Val Thr Gly Phe Asn Gln Ala Asp Ser
1070             1075             1080

Asp Lys Ile Phe Asp Asp Gly Ala Pro Glu Cys Gly Met Ser Cys
1085             1090             1095

Trp Phe Lys Lys Leu Gly Glu Trp Val Leu Gly Val Leu Asn Gly
1100             1105             1110

Asn Trp Met Val Val Ala Val Leu Ile Ala Leu Leu Ile Leu Ser
1115             1120             1125

Ile Phe Leu Phe Ala Leu Cys Cys Pro Arg Arg Pro Ser Tyr Lys
1130             1135             1140

Lys Asp His Lys Pro
1145

<210> SEQ ID NO 15
```

```
<211> LENGTH: 1135
<212> TYPE: PRT
<213> ORGANISM: Dobrava-Belgrade orthohantavirus
<220> FEATURE:
<221> NAME/KEY: misc_feature
<222> LOCATION: (1)..(1135)
<223> OTHER INFORMATION: Dobrava_Orthohantavirus_GPC NP_942554

<400> SEQUENCE: 15
```

Met Ile Met Trp Gly Leu Leu Leu Thr Met Ile Leu Ile Asp Phe Gly
1               5                   10                  15

Ala Ser Leu Arg Asn Val Tyr Asp Met Lys Ile Glu Cys Pro His Ser
            20                  25                  30

Ile Asn Phe Gly Glu Ser Ser Val Thr Gly Lys Val Glu Leu Pro Pro
        35                  40                  45

Leu Leu Leu Thr Asp Ala Glu Ala Leu Val Pro Glu Ser Ser Cys Asn
    50                  55                  60

Met Asp Asn His Gln Ser Met Ser Ile Ile Gln Lys Val Thr Lys Val
65                  70                  75                  80

Ser Trp Arg Lys Lys Ala Asp Lys Ala Gln Ala Ala Lys Asp Ser Phe
                85                  90                  95

Glu Thr Thr Ser Ser Glu Val Asn Leu Lys Gly Thr Cys Ala Leu Ser
            100                 105                 110

His Arg Met Val Glu Glu Ser Tyr Arg Asn Arg Ser Val Ile Cys
        115                 120                 125

Tyr Asp Leu Ser Cys Asn Ser Thr His Cys Lys Pro Thr Met His Met
    130                 135                 140

Ile Val Pro Val His Ser Cys Asn Met Met Lys Ser Cys Leu Val Gly
145                 150                 155                 160

Leu Gly Pro Tyr Arg Ile Gln Ile Val Tyr Glu Arg Thr Tyr Cys Thr
                165                 170                 175

Thr Gly Ile Leu Thr Glu Gly Lys Cys Phe Val Pro Asp Gln Ser Ile
            180                 185                 190

Val Asn Val Ile Lys Asn Gly Val Phe Asp Ile Ala Ser Val Ser Ile
        195                 200                 205

Val Cys Phe Phe Ile Arg Val Lys Gly Thr Asn Tyr Lys Ile Met Ala
    210                 215                 220

Ser Ile Lys Thr Ala Thr Ala Asn Asn Cys Asn Asp Thr Asp Asn Lys
225                 230                 235                 240

Val Gln Gly Tyr Tyr Leu Cys Ile Val Gly Gly Asn Ser Ser Pro Val
                245                 250                 255

Tyr Ala Pro Ser Thr Thr Asp Phe Arg Ser Met Glu Ala Leu Ala Ser
            260                 265                 270

Leu Leu Arg Ala Pro His Gly Glu Asp His Asp Leu Ser Gly Glu Glu
        275                 280                 285

Val Ala Thr Tyr Ser Ile Ala Gly Gln Ile Glu Gly Lys Ile Pro His
    290                 295                 300

Thr Ala Asn Ala Ala Asn Met Leu Phe Thr Ala Phe Ser Gly Ile Pro
305                 310                 315                 320

Ser Tyr Ser Ser Leu Ser Val Phe Ile Gly Ser Gln Asp Gly Pro Val
                325                 330                 335

Ile Tyr Ser Pro Gly Leu Phe Pro Arg Leu Asn Gln Ser Ser Cys Asp
            340                 345                 350

Lys Ile Ala Leu Pro Leu Ile Trp Glu Gly Tyr Ile Asp Leu Pro Gly
        355                 360                 365

```
Tyr Tyr Glu Thr Val His Pro Cys Asn Val Phe Cys Val Leu Ser Gly
    370             375                 380
Pro Gly Ala Ser Cys Glu Ala Phe Ser Glu Gly Gly Ile Phe Asn Ile
385             390                 395                 400
Thr Ser Pro Thr Cys Leu Val Ser Lys Gln Asn Arg Phe Arg Ala Ala
            405                 410                 415
Glu Gln Gln Val Asn Phe Val Cys Gln Arg Val Asp Gln Asp Ile Val
        420                 425                 430
Ile Tyr Cys Asn Gly Gln Lys Lys Thr Ile Leu Thr Lys Thr Leu Val
        435                 440                 445
Ile Gly Gln Cys Ile Tyr Ser Val Thr Ser Leu Phe Ser Ile Met Pro
450                 455                 460
Gly Val Ala His Ser Ile Ala Ile Glu Leu Cys Val Pro Gly Phe His
465                 470                 475                 480
Gly Trp Ala Thr Ala Ala Leu Leu Thr Thr Phe Cys Phe Gly Trp Ile
            485                 490                 495
Leu Ile Leu Ser Ile Thr Leu Ala Val Leu Val Val Leu Lys Phe Phe
            500                 505                 510
Ala Ala Ile Leu His Asn Ser Ser Gln Glu Asn Arg Phe Lys Ile Ile
        515                 520                 525
Leu Arg Lys Ile Lys Glu Glu Phe Glu Lys Thr Lys Gly Ser Met Val
    530                 535                 540
Cys Glu Val Cys Lys Tyr Glu Cys Glu Thr Gly Lys Glu Leu Lys Ala
545                 550                 555                 560
His Asn Leu Ser Cys Pro Gln Ser Gln Cys Pro Tyr Cys Phe Thr His
            565                 570                 575
Cys Glu Pro Thr Glu Ser Ala Phe Gln Ala His Tyr Lys Val Cys Gln
        580                 585                 590
Ala Thr His Arg Phe Arg Asp Asp Leu Lys Lys Thr Ile Thr Pro Gln
        595                 600                 605
Ser Thr Ser Pro Gly Cys Tyr Arg Thr Leu Asn Leu Phe Arg Tyr Lys
    610                 615                 620
Ser Arg Cys Tyr Ile Phe Thr Val Trp Val Thr Leu Ile Ile Glu
625                 630                 635                 640
Ser Ile Met Trp Ala Ala Ser Ala Ser Glu Thr Val Leu Glu Pro Ser
            645                 650                 655
Trp Asn Asp Asn Ala His Gly Val Gly Val Val Pro Met His Thr Asp
            660                 665                 670
Leu Glu Leu Asp Phe Ser Leu Pro Ser Ser Ser Lys Tyr Thr Tyr Lys
        675                 680                 685
Arg Lys Leu Thr Ser Pro Leu Asn Gln Glu Gln Ser Val Asp Leu His
        690                 695                 700
Ile Glu Ile Glu Ser Gln Gly Ile Ser Thr Ser Val His Ala Leu Gly
705                 710                 715                 720
His Trp Phe Asp Gly Arg Leu Asn Leu Lys Thr Ser Phe His Cys Tyr
            725                 730                 735
Gly Ala Cys Thr Lys Tyr Glu Tyr Pro Trp His Thr Ala Lys Cys His
            740                 745                 750
Phe Glu Arg Asp Phe Glu Tyr Glu Asn Asn Trp Gly Cys Asn Pro Ala
        755                 760                 765
Asp Cys Pro Gly Ile Gly Thr Gly Cys Thr Ala Cys Gly Leu Tyr Ile
    770                 775                 780
Asp Gln Leu Lys Pro Val Gly Ser Ala Tyr Lys Leu Ile Thr Val Arg
```

```
                785                 790                 795                 800

Tyr Ser Arg Lys Val Cys Val Gln Phe Gly Glu Glu Asn Leu Cys Lys
                    805                 810                 815

Thr Ile Asp Met Asn Asp Cys Phe Val Thr Arg His Val Lys Val Cys
                    820                 825                 830

Ile Ile Gly Thr Val Ser Lys Phe Ser Gln Gly Asp Thr Leu Val Phe
                    835                 840                 845

Leu Gly Pro Met Glu Gly Gly Leu Ile Phe Lys Asp Trp Cys Thr
            850                 855                 860

Ser Thr Cys Gln Phe Gly Asp Pro Gly Asp Ile Met Ser Pro Lys Asp
        865                 870                 875                 880

Lys Gly Phe Ser Cys Pro Asp Phe Thr Gly His Phe Arg Lys Lys Cys
                        885                 890                 895

Asn Phe Ala Thr Thr Pro Val Cys Glu Tyr Asp Gly Asn Met Val Ser
                        900                 905                 910

Gly Tyr Lys Lys Val Met Ala Thr Ile Asp Ser Phe Gln Ser Phe Asn
                        915                 920                 925

Thr Ser Ser Ile His Tyr Thr Asp Glu Arg Ile Glu Trp Lys Asp Pro
        930                 935                 940

Asp Gly Met Leu Lys Asp His Leu Asn Ile Leu Val Thr Lys Asp Ile
        945                 950                 955                 960

Asp Phe Glu Asn Leu Gly Glu Asn Pro Cys Lys Val Gly Leu Gln Thr
                        965                 970                 975

Ser Ser Ile Glu Gly Ala Trp Gly Ser Gly Val Gly Phe Thr Leu Thr
                        980                 985                 990

Cys Gln Ile Ser Leu Thr Glu Cys Ser Arg Phe Leu Thr Ser Ile Lys
                        995                 1000                1005

Ala Cys Asp Met Ala Ile Cys Tyr Gly Ala Gln Ser Val Thr Leu
                1010                1015                1020

Ile Arg Gly Gln Asn Thr Val Lys Val Ser Gly Lys Gly Gly His
                1025                1030                1035

Ser Gly Ser Ser Phe Lys Cys Cys His Gly Thr Asp Cys Ser Gln
                1040                1045                1050

Gln Gly Leu Gln Ala Ser Ala Pro His Leu Asp Lys Val Asn Gly
                1055                1060                1065

Ile Val Glu Gln Glu Ser Glu Lys Val Tyr Asp Asp Gly Ala Pro
                1070                1075                1080

Gln Cys Gly Ile Ser Cys Trp Phe Val Lys Ser Gly Glu Trp Ile
                1085                1090                1095

Thr Gly Ile Phe Asn Gly Asn Trp Ile Val Ile Val Val Leu Val
                1100                1105                1110

Phe Phe Phe Ile Leu Ser Leu Ile Leu Leu Ser Leu Leu Cys Pro
                1115                1120                1125

Ile Arg Lys His Lys Arg Ser
                1130                1135

<210> SEQ ID NO 16
<211> LENGTH: 1135
<212> TYPE: PRT
<213> ORGANISM: Hantaan orthohantavirus
<220> FEATURE:
<221> NAME/KEY: misc_feature
<222> LOCATION: (1)..(1135)
<223> OTHER INFORMATION: Hantaan_Orthohantavirus_GPC NP_941978.1

<400> SEQUENCE: 16
```

```
Met Gly Ile Trp Lys Trp Leu Val Met Ala Ser Leu Val Trp Pro Val
1               5                   10                  15

Leu Thr Leu Arg Asn Val Tyr Asp Met Lys Ile Glu Cys Pro His Thr
            20                  25                  30

Val Ser Phe Gly Glu Asn Ser Val Ile Gly Tyr Val Glu Leu Pro Pro
        35                  40                  45

Val Pro Leu Ala Asp Thr Ala Gln Met Val Pro Glu Ser Ser Cys Asn
    50                  55                  60

Met Asp Asn His Gln Ser Leu Asn Thr Ile Thr Lys Tyr Thr Gln Val
65                  70                  75                  80

Ser Trp Arg Gly Lys Ala Asp Gln Ser Gln Ser Ser Gln Asn Ser Phe
                85                  90                  95

Glu Thr Val Ser Thr Glu Val Asp Leu Lys Gly Thr Cys Val Leu Lys
                100                 105                 110

His Lys Met Val Glu Glu Ser Tyr Arg Ser Arg Lys Ser Val Thr Cys
        115                 120                 125

Tyr Asp Leu Ser Cys Asn Ser Thr Tyr Cys Lys Pro Thr Leu Tyr Met
    130                 135                 140

Ile Val Pro Ile His Ala Cys Asn Met Met Lys Ser Cys Leu Ile Ala
145                 150                 155                 160

Leu Gly Pro Tyr Arg Val Gln Val Val Tyr Glu Arg Ser Tyr Cys Met
                165                 170                 175

Thr Gly Val Leu Ile Glu Gly Lys Cys Phe Val Pro Asp Gln Ser Val
            180                 185                 190

Val Ser Ile Ile Lys His Gly Ile Phe Asp Ile Ala Ser Val His Ile
        195                 200                 205

Val Cys Phe Phe Val Ala Val Lys Gly Asn Thr Tyr Lys Ile Phe Glu
    210                 215                 220

Gln Val Lys Lys Ser Phe Glu Ser Thr Cys Asn Asp Thr Glu Asn Lys
225                 230                 235                 240

Val Gln Gly Tyr Tyr Ile Cys Ile Val Gly Gly Asn Ser Ala Pro Ile
                245                 250                 255

Tyr Val Pro Thr Leu Asp Asp Phe Arg Ser Met Glu Ala Phe Thr Gly
            260                 265                 270

Ile Phe Arg Ser Pro His Gly Glu Asp His Asp Leu Ala Gly Glu Glu
        275                 280                 285

Ile Ala Ser Tyr Ser Ile Val Gly Pro Ala Asn Ala Lys Val Pro His
    290                 295                 300

Ser Ala Ser Ser Asp Thr Leu Ser Leu Ile Ala Tyr Ser Gly Ile Pro
305                 310                 315                 320

Ser Tyr Ser Ser Leu Ser Ile Leu Thr Ser Thr Glu Ala Lys His
                325                 330                 335

Val Phe Ser Pro Gly Leu Phe Pro Lys Leu Asn His Thr Asn Cys Asp
            340                 345                 350

Lys Ser Ala Ile Pro Leu Ile Trp Thr Gly Met Ile Asp Leu Pro Gly
        355                 360                 365

Tyr Tyr Glu Ala Val His Pro Cys Thr Val Phe Cys Val Leu Ser Gly
    370                 375                 380

Pro Gly Ala Ser Cys Glu Ala Phe Ser Glu Gly Gly Ile Phe Asn Ile
385                 390                 395                 400

Thr Ser Pro Met Cys Leu Val Ser Lys Gln Asn Arg Phe Arg Leu Thr
                405                 410                 415
```

```
Glu Gln Gln Val Asn Phe Val Cys Gln Arg Val Asp Met Asp Ile Val
                420                 425                 430

Val Tyr Cys Asn Gly Gln Arg Lys Val Ile Leu Thr Lys Thr Leu Val
            435                 440                 445

Ile Gly Gln Cys Ile Tyr Thr Ile Thr Ser Leu Phe Ser Leu Leu Pro
        450                 455                 460

Gly Val Ala His Ser Ile Ala Val Glu Leu Cys Val Pro Gly Phe His
465                 470                 475                 480

Gly Trp Ala Thr Ala Ala Leu Leu Val Thr Phe Cys Phe Gly Trp Val
                485                 490                 495

Leu Ile Pro Ala Ile Thr Phe Ile Ile Leu Thr Val Leu Lys Phe Ile
            500                 505                 510

Ala Asn Ile Phe His Thr Ser Asn Gln Glu Asn Arg Leu Lys Ser Val
            515                 520                 525

Leu Arg Lys Ile Lys Glu Glu Phe Glu Lys Thr Lys Gly Ser Met Val
        530                 535                 540

Cys Asp Val Cys Lys Tyr Glu Cys Glu Thr Tyr Lys Glu Leu Lys Ala
545                 550                 555                 560

His Gly Val Ser Cys Pro Gln Ser Gln Cys Pro Tyr Cys Phe Thr His
                565                 570                 575

Cys Glu Pro Thr Glu Ala Ala Phe Gln Ala His Tyr Lys Val Cys Gln
            580                 585                 590

Val Thr His Arg Phe Arg Asp Asp Leu Lys Lys Thr Val Thr Pro Gln
            595                 600                 605

Asn Phe Thr Pro Gly Cys Tyr Arg Thr Leu Asn Leu Phe Arg Tyr Lys
        610                 615                 620

Ser Arg Cys Tyr Ile Phe Thr Met Trp Ile Phe Leu Leu Val Leu Glu
625                 630                 635                 640

Ser Ile Leu Trp Ala Ala Ser Ala Ser Glu Thr Pro Leu Thr Pro Val
                645                 650                 655

Trp Asn Asp Asn Ala His Gly Val Gly Ser Val Pro Met His Thr Asp
            660                 665                 670

Leu Glu Leu Asp Phe Ser Leu Thr Ser Ser Lys Tyr Thr Tyr Arg
            675                 680                 685

Arg Lys Leu Thr Asn Pro Leu Glu Glu Ala Gln Ser Ile Asp Leu His
        690                 695                 700

Ile Glu Ile Glu Glu Gln Thr Ile Gly Val Asp Val His Ala Leu Gly
705                 710                 715                 720

His Trp Phe Asp Gly Arg Leu Asn Leu Lys Thr Ser Phe His Cys Tyr
                725                 730                 735

Gly Ala Cys Thr Lys Tyr Glu Tyr Pro Trp His Thr Ala Lys Cys His
            740                 745                 750

Tyr Glu Arg Asp Tyr Gln Tyr Glu Thr Ser Trp Gly Cys Asn Pro Ser
        755                 760                 765

Asp Cys Pro Gly Val Gly Thr Gly Cys Thr Ala Cys Gly Leu Tyr Leu
770                 775                 780

Asp Gln Leu Lys Pro Val Gly Ser Ala Tyr Lys Ile Thr Ile Arg
            785                 790                 795                 800

Tyr Ser Arg Arg Val Cys Val Gln Phe Gly Glu Glu Asn Leu Cys Lys
            805                 810                 815

Ile Ile Asp Met Asn Asp Cys Phe Val Ser Arg His Val Lys Val Cys
        820                 825                 830

Ile Ile Gly Thr Val Ser Lys Phe Ser Gln Gly Asp Thr Leu Leu Phe
```

```
835 840 845

Phe Gly Pro Leu Glu Gly Gly Gly Leu Ile Phe Lys His Trp Cys Thr
850 855 860

Ser Thr Cys Gln Phe Gly Asp Pro Gly Asp Ile Met Ser Pro Arg Asp
865 870 875 880

Lys Gly Phe Leu Cys Pro Glu Phe Pro Gly Ser Phe Arg Lys Lys Cys
885 890 895

Asn Phe Ala Thr Thr Pro Ile Cys Glu Tyr Asp Gly Asn Met Val Ser
900 905 910

Gly Tyr Lys Lys Val Met Ala Thr Ile Asp Ser Phe Gln Ser Phe Asn
915 920 925

Thr Ser Thr Met His Phe Thr Asp Glu Arg Ile Glu Trp Lys Asp Pro
930 935 940

Asp Gly Met Leu Arg Asp His Ile Asn Ile Leu Val Thr Lys Asp Ile
945 950 955 960

Asp Phe Asp Asn Leu Gly Glu Asn Pro Cys Lys Ile Gly Leu Gln Thr
965 970 975

Ser Ser Ile Glu Gly Ala Trp Gly Ser Gly Val Gly Phe Thr Leu Thr
980 985 990

Cys Leu Val Ser Leu Thr Glu Cys Pro Thr Phe Leu Thr Ser Ile Lys
995 1000 1005

Ala Cys Asp Lys Ala Ile Cys Tyr Gly Ala Glu Ser Val Thr Leu
1010 1015 1020

Thr Arg Gly Gln Asn Thr Val Lys Val Ser Gly Lys Gly Gly His
1025 1030 1035

Ser Gly Ser Thr Phe Arg Cys Cys His Gly Glu Asp Cys Ser Gln
1040 1045 1050

Ile Gly Leu His Ala Ala Ala Pro His Leu Asp Lys Val Asn Gly
1055 1060 1065

Ile Ser Glu Ile Glu Asn Ser Lys Val Tyr Asp Asp Gly Ala Pro
1070 1075 1080

Gln Cys Gly Ile Lys Cys Trp Phe Val Lys Ser Gly Glu Trp Ile
1085 1090 1095

Ser Gly Ile Phe Ser Gly Asn Trp Ile Val Leu Ile Val Leu Cys
1100 1105 1110

Val Phe Leu Leu Phe Ser Leu Val Leu Leu Ser Ile Leu Cys Pro
1115 1120 1125

Val Arg Lys His Lys Lys Ser
1130 1135

<210> SEQ ID NO 17
<211> LENGTH: 1133
<212> TYPE: PRT
<213> ORGANISM: Seoul orthohantavirus
<220> FEATURE:
<221> NAME/KEY: misc_feature
<222> LOCATION: (1)..(1133)
<223> OTHER INFORMATION: Seoul_Orthohantavirus_GPC NP_942557.1

<400> SEQUENCE: 17

Met Trp Ser Leu Leu Leu Leu Ala Ala Leu Val Gly Gln Gly Phe Ala
1 5 10 15

Leu Lys Asn Val Phe Asp Met Arg Ile Gln Cys Pro His Ser Val Lys
20 25 30

Phe Gly Glu Thr Ser Val Ser Gly Tyr Thr Glu Leu Pro Pro Leu Ser
35 40 45

```
Leu Gln Glu Ala Glu Gln Leu Val Pro Glu Ser Ser Cys Asn Met Asp
    50                  55                  60

Asn His Gln Ser Leu Ser Thr Ile Asn Lys Leu Thr Lys Val Ile Trp
65                  70                  75                  80

Arg Lys Lys Ala Asn Gln Glu Ser Ala Asn Gln Asn Ser Phe Glu Leu
                85                  90                  95

Met Glu Ser Glu Val Ser Phe Lys Gly Leu Cys Met Leu Lys His Arg
            100                 105                 110

Met Val Glu Glu Ser Tyr Arg Asn Arg Ser Val Ile Cys Tyr Asp
            115                 120                 125

Leu Ala Cys Asn Ser Thr Phe Cys Lys Pro Thr Val Tyr Met Ile Val
        130                 135                 140

Pro Ile His Ala Cys Asn Met Met Lys Ser Cys Leu Ile Gly Leu Gly
145                 150                 155                 160

Pro Tyr Arg Val Gln Val Val Tyr Glu Arg Thr Tyr Cys Thr Thr Gly
                165                 170                 175

Ile Leu Thr Glu Gly Lys Cys Phe Val Pro Asp Lys Ala Val Val Ser
            180                 185                 190

Ala Leu Lys Arg Gly Met Tyr Ala Ile Ala Ser Ile Glu Thr Ile Cys
        195                 200                 205

Phe Phe Ile His Gln Lys Gly Asn Thr Tyr Lys Ile Val Thr Ala Ile
    210                 215                 220

Thr Ser Ala Met Gly Ser Lys Cys Asn Asn Thr Asp Thr Lys Val Gln
225                 230                 235                 240

Gly Tyr Tyr Ile Cys Ile Ile Gly Gly Asn Ser Ala Pro Val Tyr Ala
                245                 250                 255

Pro Ala Gly Glu Asp Phe Arg Ala Met Glu Val Phe Ser Gly Ile Ile
            260                 265                 270

Thr Ser Pro His Gly Glu Asp His Asp Leu Pro Gly Glu Glu Ile Ala
        275                 280                 285

Thr Tyr Gln Ile Ser Gly Gln Ile Glu Ala Lys Ile Pro His Thr Val
    290                 295                 300

Ser Ser Lys Asn Leu Lys Leu Thr Ala Phe Ala Gly Ile Pro Ser Tyr
305                 310                 315                 320

Ser Ser Thr Ser Ile Leu Thr Ala Ser Glu Asp Gly Arg Phe Ile Phe
                325                 330                 335

Ser Pro Gly Leu Phe Pro Asn Leu Asn Gln Ser Val Cys Asp Asn Asn
            340                 345                 350

Ala Leu Pro Leu Ile Trp Arg Gly Leu Ile Asp Leu Thr Gly Tyr Tyr
        355                 360                 365

Glu Ala Val His Pro Cys Asn Val Phe Cys Val Leu Ser Gly Pro Gly
    370                 375                 380

Ala Ser Cys Glu Ala Phe Ser Glu Gly Gly Ile Phe Asn Ile Thr Ser
385                 390                 395                 400

Pro Met Cys Leu Val Ser Lys Gln Asn Arg Phe Arg Ala Ala Glu Gln
                405                 410                 415

Gln Ile Ser Phe Val Cys Gln Arg Val Asp Met Asp Ile Ile Val Tyr
            420                 425                 430

Cys Asn Gly Gln Lys Lys Thr Ile Leu Thr Lys Thr Leu Val Ile Gly
        435                 440                 445

Gln Cys Ile Tyr Thr Ile Thr Ser Leu Phe Ser Leu Leu Pro Gly Val
    450                 455                 460
```

```
Ala His Ser Ile Ala Ile Glu Leu Cys Val Pro Gly Phe His Gly Trp
465                 470                 475                 480

Ala Thr Ala Ala Leu Leu Ile Thr Phe Cys Phe Gly Trp Val Leu Ile
            485                 490                 495

Pro Ala Cys Thr Leu Ala Ile Leu Leu Val Leu Lys Phe Phe Ala Asn
        500                 505                 510

Ile Leu His Thr Ser Asn Gln Glu Asn Arg Phe Lys Ala Ile Leu Arg
        515                 520                 525

Lys Ile Lys Glu Glu Phe Glu Lys Thr Lys Gly Ser Met Val Cys Glu
        530                 535                 540

Ile Cys Lys Tyr Glu Cys Glu Thr Leu Lys Glu Leu Lys Ala His Asn
545                 550                 555                 560

Leu Ser Cys Val Gln Gly Glu Cys Pro Tyr Cys Phe Thr His Cys Glu
            565                 570                 575

Pro Thr Glu Thr Ala Ile Gln Ala His Tyr Lys Val Cys Gln Ala Thr
        580                 585                 590

His Arg Phe Arg Glu Asp Leu Lys Lys Thr Val Thr Pro Gln Asn Ile
        595                 600                 605

Gly Pro Gly Cys Tyr Arg Thr Leu Asn Leu Phe Arg Tyr Lys Ser Arg
610                 615                 620

Cys Tyr Ile Leu Thr Met Trp Thr Leu Leu Ile Ile Glu Ser Ile
625                 630                 635                 640

Leu Trp Ala Ala Ser Ala Ala Glu Ile Pro Leu Val Pro Leu Trp Thr
            645                 650                 655

Asp Asn Ala His Gly Val Gly Ser Val Pro Met His Thr Asp Leu Glu
        660                 665                 670

Leu Asp Phe Ser Leu Pro Ser Ser Arg Tyr Thr Tyr Lys Arg His
        675                 680                 685

Leu Thr Asn Pro Val Asn Asp Gln Gln Ser Val Ser Leu His Ile Glu
        690                 695                 700

Ile Glu Ser Gln Gly Ile Gly Ala Asp Val His His Leu Gly His Trp
705                 710                 715                 720

Tyr Asp Ala Arg Leu Asn Leu Lys Thr Ser Phe His Cys Tyr Gly Ala
            725                 730                 735

Cys Thr Lys Tyr Gln Tyr Pro Trp His Thr Ala Lys Cys His Phe Glu
        740                 745                 750

Lys Asp Tyr Glu Tyr Glu Asn Ser Trp Ala Cys Asn Pro Asp Cys
        755                 760                 765

Pro Gly Val Gly Thr Gly Cys Thr Ala Cys Gly Leu Tyr Leu Asp Gln
        770                 775                 780

Leu Lys Pro Val Gly Thr Ala Phe Lys Ile Ile Ser Val Arg Tyr Ser
785                 790                 795                 800

Arg Lys Val Cys Val Gln Phe Gly Glu Glu Tyr Leu Cys Lys Thr Ile
            805                 810                 815

Asp Met Asn Asp Cys Phe Val Thr Arg His Ala Lys Ile Cys Ile Ile
        820                 825                 830

Gly Thr Val Ser Lys Phe Ser Gln Gly Asp Thr Leu Leu Phe Leu Gly
        835                 840                 845

Pro Met Glu Gly Gly Ile Ile Phe Lys His Trp Cys Thr Ser Thr
        850                 855                 860

Cys His Phe Gly Asp Pro Gly Asp Val Met Gly Pro Lys Asp Lys Pro
865                 870                 875                 880

Phe Ile Cys Pro Glu Phe Pro Gly Gln Phe Arg Lys Lys Cys Asn Phe
```

885                 890                 895
Ala Thr Thr Pro Val Cys Glu Tyr Asp Gly Asn Ile Ile Ser Gly Tyr
                900                 905                 910

Lys Lys Val Leu Ala Thr Ile Asp Ser Phe Gln Ser Phe Asn Thr Ser
            915                 920                 925

Asn Ile His Phe Thr Asp Glu Arg Ile Glu Trp Arg Asp Pro Asp Gly
    930                 935                 940

Met Leu Arg Asp His Ile Asn Ile Val Ile Ser Lys Asp Ile Asp Phe
945                 950                 955                 960

Glu Asn Leu Ala Glu Asn Pro Cys Lys Val Gly Leu Gln Ala Ala Asn
                965                 970                 975

Ile Glu Gly Ala Trp Gly Ser Gly Val Gly Phe Thr Leu Thr Cys Gln
            980                 985                 990

Val Ser Leu Thr Glu Cys Pro Thr Phe Leu Thr Ser Ile Arg Ala Cys
    995                 1000                1005

Asp Met Ala Ile Cys Tyr Gly Ala Glu Ser Val Thr Leu Ser Arg
    1010                1015                1020

Gly Gln Asn Thr Val Lys Ile Thr Gly Lys Gly His Ser Gly
    1025                1030                1035

Ser Ser Phe Lys Cys Cys His Gly Lys Glu Cys Ser Leu Thr Gly
    1040                1045                1050

Leu Gln Ala Ser Ala Pro His Leu Asp Lys Val Asn Gly Ile Ser
    1055                1060                1065

Glu Leu Glu Asn Glu Lys Val Tyr Asp Asp Gly Ala Pro Glu Cys
    1070                1075                1080

Gly Ile Thr Cys Trp Phe Lys Lys Ser Gly Glu Trp Val Met Gly
    1085                1090                1095

Ile Ile Asn Gly Asn Trp Val Val Leu Ile Val Leu Cys Val Leu
    1100                1105                1110

Leu Leu Phe Ser Leu Ile Leu Leu Ser Ile Leu Cys Pro Val Arg
    1115                1120                1125

Lys His Lys Lys Ser
    1130

<210> SEQ ID NO 18
<211> LENGTH: 1133
<212> TYPE: PRT
<213> ORGANISM: Longquan virus
<220> FEATURE:
<221> NAME/KEY: misc_feature
<222> LOCATION: (1)..(1133)
<223> OTHER INFORMATION: Longquan Loanvirus_GPC AGI62348.1

<400> SEQUENCE: 18

Met Lys Ser Ile Leu Leu Ile Leu Leu Leu Glu Gln Val Arg Ser Lys
1               5                   10                  15

Ala Thr Asn Glu Ile Lys Leu Glu Cys Pro His Asp Gln Arg Val Glu
                20                  25                  30

Thr Gly Phe Ser His Gly Phe Thr Asp Leu Ser Pro Ile Leu Tyr Thr
            35                  40                  45

Lys Gly Leu Phe Thr Lys His Leu Glu Asn Asn Cys Pro Phe Asp Ile
        50                  55                  60

Ser Ile Ile Asn Arg Leu Val Arg Asp Val Arg Ile Ser Thr Trp Gln
65              70                  75                  80

Ala Lys Ser Thr Asn Thr Asp Ala Thr Val Ala Ser Ala Thr Ser Phe
                85                  90                  95

```
Glu Thr Lys Asp Thr Asp Lys Leu Ala Gly Val Cys Gly Phe Phe
            100                 105                 110

Asp Asp Ile Thr Lys Pro Lys Gln Gly Gln Arg Lys Ala Ile Ile Cys
            115                 120                 125

Tyr Asp Leu Ser Cys Asn Gln Thr His Cys Leu Pro Thr Leu His Leu
        130                 135                 140

Ile Phe Pro Gln Gln Phe Cys Gln Ser Leu Lys Gln Cys Ser Ile Asn
145                 150                 155                 160

Ala Tyr Asp His Lys Ile Leu Ile Thr Ile Ser Leu Ser Phe Cys Pro
                165                 170                 175

Glu Gly Leu Ile Ile Gly Gly Asn Cys Ile Val Pro Val Leu Ala Gln
            180                 185                 190

Ser Gln Leu Leu His Asn His Met Thr Tyr Asn Ile Lys Val Thr Cys
        195                 200                 205

Phe Phe Glu Tyr Ser Met Ala Arg Glu Ser Leu Asp Asn Lys Phe Leu
        210                 215                 220

Glu Glu Met Asn Arg Leu Val Leu Gly Arg Asn Cys Glu Lys Thr Glu
225                 230                 235                 240

Tyr Leu Gly Gly Tyr Val Cys Phe Leu Ala Gly Tyr Gly Thr Ala Ile
                245                 250                 255

His Val Pro Tyr Asp Asn Thr Tyr Leu Ser Gly Ala Val Val Asn Ser
            260                 265                 270

Met Lys Ala Asn Leu His Gly Glu Asp His Asp Arg Leu Lys Leu Gly
        275                 280                 285

Asp Thr Ser Ala Val Ile Ala Gly Asn Leu Lys Phe Val Ile Asp Ser
        290                 295                 300

Thr Ala Pro Glu Lys Ser Tyr Gln Gly Glu Cys Phe Thr Gly His Met
305                 310                 315                 320

Gly Tyr Thr Ser Leu Tyr Phe Tyr Pro Val Arg Ser Lys Gly Lys Tyr
                325                 330                 335

Val Thr Ile Leu Thr Lys Gly Val Ile Pro Val Ile Asn Lys Thr Thr
            340                 345                 350

Cys Met Pro Lys Ile Val Pro Leu Val Trp Thr Gly Met Val Glu Met
        355                 360                 365

Arg Gly Ile Glu Glu Lys Leu Glu Ala Cys Thr Met His Cys Ile Met
        370                 375                 380

Val Gly Asn Gly Ala Thr Cys Glu Ala Phe Ser Ala Thr Gly Ile Phe
385                 390                 395                 400

Asp Ile Lys Ser Thr Thr Cys Gln Ile Gly Lys Thr His Lys Tyr Arg
                405                 410                 415

Arg Thr Glu Asp Gln Ile Thr Phe Thr Cys Gln Asp Leu Asn Lys Asp
            420                 425                 430

Ile Ser Val Ile Cys Asn Gly Glu Asn Ile Thr Val Pro Val Lys Ser
        435                 440                 445

Leu Ile Val Gly Gln Cys Ile Tyr Thr Ile Thr Ser Ile Phe Ser Ile
        450                 455                 460

Phe Pro Ala Thr Ala His Ser Ile Ala Thr Glu Met Cys Val Gln Gly
465                 470                 475                 480

Ile His Gly Trp Leu Thr Ile Ile Phe Phe Thr Phe Cys Phe Gly
                485                 490                 495

Trp Leu Leu Ile Pro Ile Leu Thr Cys Leu Ile Ile Asn Thr Ile Ala
            500                 505                 510
```

```
Tyr Ser Leu Ile Thr Leu Ala Tyr Phe Lys Asn Gly Ala Arg Leu Gly
            515                 520                 525

Asn Leu Ile Lys Arg Met Lys Ser Glu Phe Gln Arg Thr Ile Gly Asn
530                 535                 540

Thr Thr Cys Asn Ile Cys Leu Arg Glu Cys Glu Ser Glu Ser Glu Tyr
545                 550                 555                 560

Lys Ser His Glu Glu Leu Cys Lys Asn Gly Ser Cys Pro Tyr Cys Met
            565                 570                 575

Lys Asp Ile Gly Val Ser Gln Val Leu Leu Asn Glu His Tyr Asn Ala
            580                 585                 590

Cys Met Leu Ile Asp Arg Tyr Glu Lys Arg Leu Thr His Thr Leu Asn
            595                 600                 605

Gln Thr Pro Leu Tyr Ser Arg Lys Val Arg Lys Ile Gln Ser Phe Arg
            610                 615                 620

Tyr Arg Asn Arg Cys Phe Ile Leu Thr Val Trp Ile Ile Leu Leu Thr
625                 630                 635                 640

Val Glu Ser Leu Ile Trp Ala Ser Ser Ala Glu Asp Ile Lys Pro Ala
            645                 650                 655

Pro Lys Trp Gln Asn Thr Ala His Gly Ile Gly Thr Ile Lys Leu Asn
            660                 665                 670

Ser Asp Tyr Glu Leu Asp Phe Ser Val Val Ala Gly Ser Glu Phe Thr
            675                 680                 685

His Lys Arg Met Leu Gln Ser Pro Glu Ser Gly Lys Lys Asn Ile Pro
            690                 695                 700

Phe Thr Val Tyr Leu Ser Glu Gln Leu Ile Thr Ser Thr Val Gln Ile
705                 710                 715                 720

Leu Gly Asn Trp Met Asp Ala Glu Ile Asn Val Lys Ser Val Phe His
            725                 730                 735

Cys Tyr Gly Thr Cys Lys Lys Tyr Ser Tyr Pro Trp Gln Ser Ser Pro
            740                 745                 750

Cys His Lys Glu Val Asp Phe Glu Phe Gln Ser Ser Trp Gly Cys Asn
            755                 760                 765

Pro Ile Ser Cys Pro Gly Ile Asn Ser Gly Cys Thr Ala Cys Gly Thr
770                 775                 780

Tyr Val Asp Lys Leu Lys Thr Ile Ala Lys Ala Tyr Arg Ile Ile Thr
785                 790                 795                 800

Val Lys Tyr Ser Arg Lys Val Cys Tyr Gln Ile Gly Thr Lys Lys Ala
            805                 810                 815

Cys Lys Thr Leu Glu Ser Asn Asp Cys Leu Val Ser Asn Gly Val Lys
            820                 825                 830

Ile Cys Ala Ile Gly Thr Ile Ser Thr Leu Gln Thr Gly Met Thr Leu
            835                 840                 845

Val Phe Phe Gly Pro Leu Asn Gly Gly Ala Leu Leu Ile Lys Asp Trp
850                 855                 860

Cys Ile Ser Ser Cys Lys Phe Gly Asp Pro Gly Asp Ile Met Gln Ile
865                 870                 875                 880

Ser Asn Asn Ile Thr Cys Pro Ser Phe Asp Gly Thr Met Gln Arg Val
            885                 890                 895

Cys Arg Phe Gly Leu Glu Pro Met Cys Ser Tyr Ser Gly Asn Lys Ile
            900                 905                 910

Ser Gly Val Lys Arg Val Leu Glu Thr Lys Asp Ser Tyr Leu Ser Val
            915                 920                 925

Asn Leu Thr Lys Pro Lys Leu Val Gly Ser Thr Leu Leu Trp Asn Ser
```

```
                930             935             940
Leu Asp Ser Ser Ile Lys Asp His Ile Asn Ile Val Val Ser Asn Asp
945                 950             955                 960

Ile Asp Phe Glu Asp Leu Ala Glu Thr Pro Cys Lys Val Thr Ile Lys
                965             970             975

Asn Leu Lys Ile Glu Gly Ala Trp Gly Ser Gly Ile Gly Ile Lys Leu
                980             985             990

His Cys Glu Val Ser Leu Ser Glu Cys Ser Glu Tyr Leu Thr Thr Ile
                995             1000            1005

Lys Val Cys Asp Asn Ala Ile Cys Tyr Gly Gly Asn Val Ala His
        1010            1015            1020

Leu Ser Arg Gly Leu Asn Thr Val Ile Ile Lys Gly Ala Gly Gly
        1025            1030            1035

His Ser Gly Ser Ser Phe Lys Cys Cys His Glu Thr Ser Cys Ser
        1040            1045            1050

Asp Ile Gly Phe Lys Ala Glu Ala Pro His Leu Ala Arg Ile Val
        1055            1060            1065

Asp Asp Gly Ile Thr Thr Ser Met Ser Tyr Ser Asp Gly Ala Pro
        1070            1075            1080

Glu Ala Gly Ile Val Ser Trp Ile Tyr Lys Val Ala Glu Trp Ile
        1085            1090            1095

Lys Gly Met Phe Asn Gly Asn Trp Phe Val Leu Ile Ile Met Ile
        1100            1105            1110

Leu Phe Leu Ile Ile Ser Ile Val Leu Leu Ile Phe Leu Cys Pro
        1115            1120            1125

Val Lys Lys Tyr Lys
        1130

<210> SEQ ID NO 19
<211> LENGTH: 1140
<212> TYPE: PRT
<213> ORGANISM: Asama virus
<220> FEATURE:
<221> NAME/KEY: misc_feature
<222> LOCATION: (1)..(1140)
<223> OTHER INFORMATION: Asama_Orthohantavirus_GPC ACI28508.1

<400> SEQUENCE: 19

Met Lys Val Glu Cys Arg Gln Ile Ile Gly Leu Thr Ile Leu Val Cys
1               5                   10                  15

Val Ala Gly Ile Asn Gly Arg Asn Val Phe Glu Leu Tyr Leu Asp Cys
                20                  25                  30

Pro His Ala Val Gln Phe Gly Glu Thr Thr Leu His Gly Ser Ile Thr
            35                  40                  45

Leu Pro Pro Ile Pro Ile Ala Asp Ala Val Ala Leu Glu Val Glu Ser
        50                  55                  60

Ser Cys Ser Met Asp Val His Ser Ser Leu Arg Ala Ser Thr Glu Leu
65                  70                  75                  80

Thr Gln Ile Thr Trp Ala Lys Lys Asn Asp His Thr Gly Ala Ala Ala
                85                  90                  95

Ala Thr Ser Phe Glu Ala Thr Ser Val Gln Lys Ser Met Lys Gly Leu
            100                 105                 110

Cys Ile Leu Thr His Lys Val Ile Glu Gln Ala Tyr Lys Ser Arg Lys
        115                 120                 125

Ser Val Ile Cys Tyr Asp Leu Ile Cys Asn Gln Thr Ala Cys Lys Pro
    130                 135                 140
```

```
Glu Leu His Tyr Met Ser Pro Ile His Ala Cys Asn Met Met Lys Ser
145                 150                 155                 160

Cys Ile Val Gly Val Gly Pro Phe Arg Val Gln Ile Ile Phe Lys Arg
                165                 170                 175

Thr Tyr Cys Thr Val Gly Ile Leu Ile Glu Gly Lys Cys Phe Arg Pro
            180                 185                 190

Asp Arg Ser Leu Ile Asn Ser Ile Lys Pro Gly Leu Leu Glu Ser Ala
        195                 200                 205

Thr Leu Asn Ile His Cys Phe Leu Ile Ala Lys Thr Asp Glu Lys Leu
    210                 215                 220

Lys Leu Val Glu Glu Ile Glu Lys Phe Lys Thr Thr Asn Gly Cys Thr
225                 230                 235                 240

Thr Asn Glu Gln Lys Phe Gln Gly Tyr Tyr Ile Cys Leu Phe Gly Gly
                245                 250                 255

Ser Ser Glu Val Phe Arg Leu Pro Asn Pro Asp Asp Ser Arg Ser Lys
            260                 265                 270

His Leu Phe Gln Ser Ile Tyr Leu Ser Pro His Gly Glu Asp His Asp
        275                 280                 285

Asn Ile Gly Glu Glu Tyr Gly Asn Val Arg Ile Ala Gly Pro Ile Glu
    290                 295                 300

Ile Lys Ile Pro His Thr Glu Ser Thr Ala Asn Val Lys Ala Ile Ala
305                 310                 315                 320

Phe Thr Gly Thr Pro Met Tyr Ser Ser Leu Ser Ala Tyr Pro Lys Asp
                325                 330                 335

Val Ser Pro Lys Tyr Ala Phe His Pro Gly Leu Ile Leu Asn Tyr Asn
            340                 345                 350

Gln Ser Glu Cys Ser Lys Lys Gly Leu Pro Ile Val Trp Thr Gly Leu
        355                 360                 365

Ile Glu Met Pro Gly Thr Tyr Glu Pro Ile Asn Lys Cys Asn Val Phe
    370                 375                 380

Cys Val Leu Ser Gly Pro Gly Ala Ser Cys Glu Ala Phe Ala Glu Gly
385                 390                 395                 400

Gly Ile Phe Asn Ile Ser Ser Pro Thr Cys Leu Val Ser Lys His Thr
                405                 410                 415

Thr Phe Lys Thr Ser Asp Gln Gln Ile Thr Phe Val Cys Gln Arg Ile
            420                 425                 430

Asp Thr Asp Ile Ile Val Tyr Cys Asn Gly Tyr Lys Lys Ile Ile Leu
        435                 440                 445

Thr Lys Thr Leu Ile Ile Gly Gln Cys Ile Tyr Thr Val Thr Ser Ile
    450                 455                 460

Phe Ser Ile Phe Ser Ser Val Ala His Ser Ile Ala Val Glu Leu Cys
465                 470                 475                 480

Val Pro Gly Phe His Gly Trp Thr Thr Met Ile Leu Ile Thr Phe
                485                 490                 495

Cys Phe Gly Trp Leu Leu Ile Pro Ile Ile Thr Trp Leu Ile Leu Ile
            500                 505                 510

Ile Leu Lys Phe Ile Ala Ser Ile Leu His Ser Gln Ser Glu Glu Asn
        515                 520                 525

Arg Phe Lys Thr Leu Leu Arg Lys Ile Lys Glu Glu Tyr Glu Arg Thr
    530                 535                 540

Lys Gly Ser Met Val Cys Asp Ile Cys Lys Val Glu Cys Glu Thr Gln
545                 550                 555                 560
```

-continued

Met Glu Tyr Lys Ala His Gly Val Ser Cys Pro Gln Asn Gln Cys Pro
                565                 570                 575

Tyr Cys Phe Ala Ala Cys Glu Pro Ser Glu Ser Ala Phe Gln Ala His
            580                 585                 590

Tyr Lys Ala Cys Gln Val Thr His Arg Phe Ser Asp Glu Leu Arg Lys
        595                 600                 605

Thr Ile Ser Met Lys Pro Lys Asn Gln Gly Cys Tyr Arg Thr Leu Asn
    610                 615                 620

Leu Phe Arg Tyr Arg Ser Arg Cys Tyr Ile Phe Thr Val Trp Ile Leu
625                 630                 635                 640

Leu Leu Thr Ile Glu Ser Ile Phe Trp Ala Val Ser Ala Glu Pro Glu
                645                 650                 655

Pro Leu Val Pro Thr Trp Asn Asp Asn Ala His Gly Ile Gly Arg Ile
            660                 665                 670

Thr Leu Asn Asn Asp Leu Glu Leu Asp Phe Ser Leu Thr Ser Ser Ser
        675                 680                 685

Lys Tyr Thr Tyr Arg Arg Leu Leu Ile Asn Pro Arg Asp Asp Asn Gln
    690                 695                 700

Arg Ala Thr Ile His Leu Glu Ile Tyr Pro Gln Val Ile Thr Ala Glu
705                 710                 715                 720

Val Gln Asn Leu Gly His Trp Phe Asp Ala Gln Leu Asn Ile Lys Thr
                725                 730                 735

Ile Phe His Cys Tyr Gly Glu Cys Ser Lys Tyr Ser Tyr Pro Trp Gln
            740                 745                 750

Thr Ala Ser Cys Lys Phe Glu Lys Asp Tyr Gln Tyr Glu Ser Gly Trp
        755                 760                 765

Gly Cys Asn Pro Ile Asp Cys Pro Gly Val Gly Thr Gly Cys Thr Ala
    770                 775                 780

Cys Gly Leu Tyr Leu Asp Lys Phe Arg Ser Val Gly Thr Ala Tyr Lys
785                 790                 795                 800

Ile Val Ser Ile Arg Tyr Thr Arg Arg Ile Cys Val Gln Phe Asn Glu
                805                 810                 815

Glu Thr Asn Cys Lys Val Leu Asp Ser Asn Asp Cys Phe Ile Thr Arg
            820                 825                 830

Asn Phe Lys Ile Cys Met Val Gly Thr Val Ser Lys Phe Thr Gln Gly
        835                 840                 845

Asp Thr Leu Leu Phe Leu Gly Pro Met Glu Gly Gly Leu Ile Leu
    850                 855                 860

Lys Gln Trp Cys Thr Thr Ser Cys Gln Tyr Gly Asp Pro Gly Asp Ile
865                 870                 875                 880

Met Lys Leu Tyr Glu Arg Gly Phe Gln Cys Pro Asp Tyr Pro Gly Thr
                885                 890                 895

Phe Trp Lys Arg Cys Met Phe Ala His Thr Pro Val Cys Glu Tyr Gln
            900                 905                 910

Gly Asn Thr Met Ser Gly Tyr Lys Lys Leu Met Ala Thr Ile Asp Ser
        915                 920                 925

Phe Gln Ser Phe Asn Thr Thr Asp Ile His Tyr Thr Lys Asn Arg Leu
    930                 935                 940

Glu Trp Ser Asp Pro Asp Gly Leu Leu Arg Asp His Ile Asn Val Leu
945                 950                 955                 960

Val Ser Arg Glu Val Glu Phe Thr Asp Leu Ser Asp Asn Pro Cys Arg
                965                 970                 975

Leu Asn Val Gln Thr Ile Asn Ile Glu Gly Ser Trp Gly Ser Gly Val

-continued

```
              980                 985                 990
Gly Phe Thr Leu Lys Cys Val Val Ser Leu Thr Glu Cys Pro Ser Phe
            995                1000               1005

Ile Thr Ser Ile Lys Ala Cys Asp Ala Ala Ile Cys Tyr Gly Ala
    1010            1015            1020

Lys Ser Val Thr Leu Ser Arg Gly Gln Asn Val Val Leu Val Val
    1025            1030            1035

Gly Lys Gly Gly His Ser Gly Ser Lys Phe Arg Cys Cys His Asp
    1040            1045            1050

Glu Val Cys Ser Ser Asp Gly Leu Leu Ala Ser Ser Pro His Leu
    1055            1060            1065

Glu Arg Val Thr Ala Val Asp Ala Ile Leu Asp Asn His Ile Tyr
    1070            1075            1080

Asp Asp Gly Ala Pro Lys Cys Arg Phe Lys Cys Trp Phe His Lys
    1085            1090            1095

Thr Gly Glu Trp Leu Trp Gly Leu Phe Gln Gly Asn Trp Met Val
    1100            1105            1110

Val Val Val Leu Val Ala Leu Leu Ile Ile Ser Leu Ile Cys Leu
    1115            1120            1125

Ser Phe Leu Cys Pro Val Arg Lys Leu Lys Arg Gly
    1130            1135            1140
```